(12) United States Patent
Minamiguchi et al.

(10) Patent No.: US 10,370,372 B2
(45) Date of Patent: *Aug. 6, 2019

(54) FUSED PYRIMIDINE COMPOUND OR SALT THEREOF

(71) Applicant: TAIHO PHARMACEUTICAL CO., LTD., Chiyoda-ku (JP)

(72) Inventors: Kazuhisa Minamiguchi, Moriya (JP); Shigeo Okajima, Kumagaya (JP); Takahiro Asai, Tsukuba (JP); Masanori Asai, Tsukuba (JP); Yoshio Ogino, Tsukuba (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/771,487

(22) PCT Filed: Nov. 25, 2016

(86) PCT No.: PCT/JP2016/084944
§ 371 (c)(1),
(2) Date: Apr. 27, 2018

(87) PCT Pub. No.: WO2017/090719
PCT Pub. Date: Jun. 1, 2017

(65) Prior Publication Data
US 2018/0312505 A1  Nov. 1, 2018

(30) Foreign Application Priority Data

Nov. 27, 2015 (JP) .................................. 2015-232273

(51) Int. Cl.
| | | |
|---|---|---|
| C07D 471/04 | (2006.01) |
| C07D 519/00 | (2006.01) |
| A61K 31/519 | (2006.01) |
| A61K 31/55 | (2006.01) |
| A61P 35/00 | (2006.01) |

(52) U.S. Cl.
CPC .......... *C07D 471/04* (2013.01); *A61K 31/519* (2013.01); *A61K 31/55* (2013.01); *A61P 35/00* (2018.01); *C07D 519/00* (2013.01)

(58) Field of Classification Search
CPC ...... C07D 471/04; A61K 31/519; A61P 35/00
USPC ........................................ 544/279; 514/264.1
See application file for complete search history.

(56) References Cited

U.S. PATENT DOCUMENTS

| | | | | |
|---|---|---|---|---|
| 9,662,333 B2 * | 5/2017 | Minamiguchi | ...... | A61K 31/519 |
| 9,889,136 B2 * | 2/2018 | Minamiguchi | ...... | A61K 31/519 |
| 2005/0215572 A1 | 9/2005 | Kelly et al. | | |
| 2005/0277643 A1 | 12/2005 | Kelly et al. | | |
| 2006/0128710 A1 | 6/2006 | Lee et al. | | |
| 2006/0160845 A1 | 7/2006 | Schlienger et al. | | |
| 2006/0173037 A1 | 8/2006 | Schlienger et al. | | |
| 2009/0270449 A1 | 10/2009 | Schlienger et al. | | |
| 2011/0152282 A1 | 6/2011 | Cheng et al. | | |
| 2013/0296333 A1 | 11/2013 | Cheng et al. | | |
| 2016/0244444 A1 | 8/2016 | Minamiguchi et al. | | |
| 2016/0310496 A1 | 10/2016 | Minamiguchi et al. | | |

FOREIGN PATENT DOCUMENTS

| | | |
|---|---|---|
| JP | 2002-88073 A | 3/2002 |
| JP | 2007-517045 A | 6/2007 |
| JP | 2008-526888 A | 7/2008 |
| JP | 2012-500853 A | 1/2012 |
| WO | WO 2005/066171 A1 | 7/2005 |
| WO | WO 2006/062981 A2 | 6/2006 |
| WO | WO 2006/118598 A1 | 11/2006 |
| WO | WO 2015/182712 A1 | 12/2015 |

OTHER PUBLICATIONS

Zhang etal., Expert Opin. Drug Discov. (2013) 8(2): 191-218.*
Liao et al., Transl Androl Urol 2013;2(3):187-196.*
Narayanan et al. Cancers 2016, 8, 108, 1-17.*
Watson et al. Nat Rev Cancer. Dec. 2015; 15(12): 701-711.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Koivisto, P., et al., "Androgen Receptor Gene Amplification: A Possible Molecular Mechanism for Androgen Deprivation Therapy Failure in Prostate Cancer," Cancer Res 57, Jan. 15, 1997, 7 pages.
Gregory, C. et al., "Androgen Receptor Stabilization in Recurrent Prostate Cancer is Associated with Hypersensitivity to Low Androgen," Cancer Res 61, Apr. 1, 2001, 8 pages.

(Continued)

*Primary Examiner* — Venkataraman Balasubramanian
(74) *Attorney, Agent, or Firm* — Oblon, McClelland, Maier & Neustadt, L.L.P.

(57) ABSTRACT

To provide a compound having an inhibitory activity for an androgen receptor. A fused pyrimidine compound represented by the following formula (I) or a pharmaceutically acceptable thereof (in the formula, X, Y, Z, $R_1$, and $R_2$ are as defined in the specification).

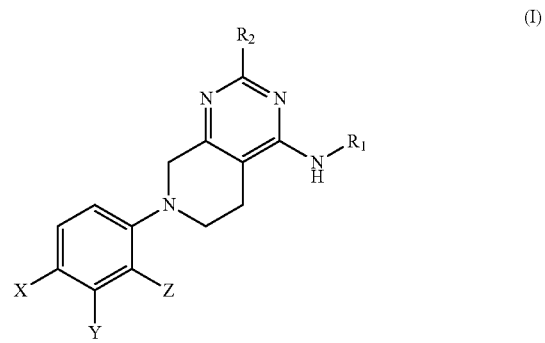

(I)

14 Claims, No Drawings

(56) References Cited

OTHER PUBLICATIONS

Taplin, M. et al., "Mutation of the Androgen-Receptor Gene in Metastatic Androgen-Independent Prostate Cancer," The New England Journal of Medicine, vol. 332, No. 21, May 25, 1995, pp. 1393-1398.

Zhao, X. et al., "Glucocorticoids can promote androgen-independent growth of prostate cancer cells through a mutated androgen receptor," Nature Medicine, vol. 6, No. 6, Jun. 2000, pp. 703-706.

Tan, J. et al., Dehydroepiandrosterone Activates Mutant Androgen Receptors Expressed in the Androgen-Dependent Human Prostate Cancer Xenograft CWR22 and LNCaP Cells, Molecular Endocrinology 11, 1997, pp. 450-459.

Chen, C. et al., "Molecular determinants of resistance to antiandrogen therapy," Nature Medicine, vol. 10, No. 1, Jan. 2004, pp. 33-39.

Hara, T. et al., "Novel Mutations of Androgen Receptor: A Possible Mechanism of Bicalutamide Withdrawal Syndrome," Cancer Res 63, Jan. 1, 2003, 6 pages.

Matsumoto, H. et al., "An evaluation of clusterin antisense inhibitor OGX-011 in combination with the second-generation antiandrogen MDV3100 in a castrate-resistant prostate cancer model," J Clin Oncol 29, 2011, 2 pages (Abstract only).

Zhang, Y. et al., "Discovery of a novel class anti-proliferative agents and potential inhibitors of EGFR tyrosine kinases based on 4-anilinotetrahydropyrido[4,3-d]pyrimidine scaffold : Design, synthesis and biological evaluations," Bioorganic & Medicinal Chemistry, vol. 23, No. 15, Jun. 6, 2015, pp. 4591-4607.

Trump, R. et al., "Design and Synthesis of an Array of Selective Androgen Receptor Modulators," Journal of Combinatorial Chemistry, vol. 9, No. 1, 2007, pp. 107-114.

International Search Report dated Feb. 14, 2017 in PCT/JP2016/084944 filed Nov. 25, 2016.

* cited by examiner

FUSED PYRIMIDINE COMPOUND OR SALT THEREOF

TECHNICAL FIELD

The present invention relates to a novel fused pyrimidine compound which is useful as a pharmaceutical agent, in particular, an anti-androgen agent, or a salt thereof, and a pharmaceutical composition containing them.

BACKGROUND ART

Prostate cancer is the cancer with the highest incidence in men in western countries, and it is the second leading cause of cancer death. In Japan, according to westernization in food preferences and human population aging, the number of prostate cancer patients also increases over the years. In general, proliferation of prostate cancer cells is stimulated by androgen. As such, for treatment of unresectable progressive prostate cancer, patients are treated with surgical or chemical castration, and/or administration of an anti-androgen agent so-called androgen deprivation therapy. According to surgical or chemical castration, level of androgen circulating in human body is lowered so that the activity of an androgen receptor (it may be referred to as AR hereinbelow) is lowered. As the anti-androgen agent is administered, the binding of androgen to AR is inhibited, yielding lower AR activity. Those therapies are very effective for early stage treatment of most patients. However, cancer recurrence occurs within several years. Such recurrent prostate cancer is referred to as castration resistant prostate cancer (CRPC).

As a cause of castration resistant prostate cancer, amplification and overexpression of the AR gene have been confirmed and reported (Non-Patent Literatures 1 and 2). As a result of overexpression of AR, castration resistant prostate cancer exhibits high sensitivity even for androgen at an ultra-low concentration, which is caused by castration treatment. Namely, according to overexpression of AR, AR is activated to cause cancer proliferation. AR mutation has been also confirmed and reported as a cause of castration resistant prostate cancer (Non-Patent Literatures 3 to 5). According to a mutation in AR, estrogen or an anti-androgen agent itself, which is currently used, can function as an AR agonist, in addition to androgen.

Bicalutamide is the most generally used anti-androgen agent, and exhibits an inhibitory effect in hormone-sensitive prostate cancer as an antagonist for AR. However, the anti-androgen agent including bicalutamide, which is used for androgen deprivation therapy, has no effectiveness against castration resistant prostate cancer. The main reason is that, as AR is overexpressed in castration resistant prostate cancer, the AR antagonist activity is not fully exhibited and the AR agonist activity is shown (Non-Patent Literatures 6 and 7). As such, for inhibition of overexpressed AR in castration resistant prostate cancer, an anti-androgen agent having a more potent AR antagonist activity than a currently used anti-androgen agent and not having an AR agonist activity is needed. Furthermore, as the anti-androgen agent also has an effect of reducing AR expression, it can be a more effective therapeutic agent for castration resistant prostate cancer (Non-Patent Literature 8).

In a related art, 5,6,7,8-tetrahydropyrido[3,4-d]pyrimidine having a fused pyrimidine structure has been reported as an inhibitor for vanilloid receptor 1 (VR1) (Patent Literatures 1 to 3). In Patent Literature 1, a bicycloheteroarylamine compound useful for treatment of pain, inflammatory hyperalgesia, overactive bladder, and urinary incontinence based on inhibition of VR1 receptor is disclosed. Furthermore, in Patent Literatures 2 and 3, a bicycloheteroarylamine compound useful for treatment of inflammatory pain, for example, is disclosed, and an experimental data for thermal hyperalgeia is described. However, a compound having cyano benzene at position 7 of the 5,6,7,8-tetrahydropyrido[3',4-d]pyrimidine has not been reported in any one of those Patent Literatures 1 to 3. In addition, there are no descriptions regarding the data relating to an anti-tumor effect, and the AR antagonist activity or the activity of reducing AR expression is not described at all.

CITATION LIST

Patent Literature

Patent Literature 1: WO 2006/062981
Patent Literature 2: WO 2005/066171
Patent Literature 3: WO 2006/118598

Non-Patent Literature

Non-Patent Literature 1: Koivisto P et al., "Androgen receptor gene amplification: a possible molecular mechanism for androgen deprivation therapy failure in prostate cancer", Cancer Res 57: 314-319, 1997
Non-Patent Literature 2: Gregory C W et al., "Androgen receptor stabilization in recurrent prostate cancer is associated with hypersensitivity to low androgen", Cancer Res 61: 2892-2898, 2001
Non-Patent Literature 3: Taplin M E et al., "Mutation of the androgen-receptor gene in metastatic androgen-independent prostate cancer", N Engl J Med 332: 1393-1398, 1995
Non-Patent Literature 4: Zhao X Y et al., "Glucocorticoids can promote androgen-independent growth of prostate cancer cells through a mutated androgen receptor", Nat Med 6: 703-706, 2000
Non-Patent Literature 5: Tan J et al., "Dehydroepiandrosterone activates mutant androgen receptors expressed in the androgen-dependent human prostate cancer xenograft CWR22 and LNCaP cells", Mol Endocrinol 11: 450-459, 1997
Non-Patent Literature 6: Charlie D Chen et al., "Molecular determinants of resistance to antiandrogen therapy", Nature Medicine 10:33-39, 2004
Non-Patent Literature 7: Takahito Hara et al., "Novel Mutations of Androgen Receptor: A Possible Mechanism of Bicalutamide Withdrawal Syndrome", Cancer Res 63: 149-153, 2003
Non-Patent Literature 8: H. Matsumoto et al., "An evaluation of clusterin antisense inhibitor OGX-011 in combination with the second-generation antiandrogen MDV3100 in a castrate-resistant prostate cancer model", J Clin Oncol 29: 2011 (suppl; abstr 4502)

SUMMARY OF THE INVENTION

Problems to be Solved by the Invention

The present invention provides a novel fused pyrimidine compound, which has a stronger antagonist activity for AR overexpressed in castration resistant prostate cancer than a currently prescribed anti-androgen agent such as bicalutamide, does not exhibit an agonistic activity for AR, and has an activity of reducing AR expression amount, or a pharmaceutically acceptable salt thereof.

Means for Solving the Problems

As a result of intensive studies, the inventors of the present invention found a novel compound group having 5,6,7,8-tetrahydropyrido[3,4-d]pyrimidine, which is a fused pyrimidine compound, as a basic structure, a group represented by —$NHR_1$ at position 4, and cyanobenzene or nitrobenzene at position 7. The compound group has an antagonist activity but no agonist activity for AR, and in addition to effectiveness for cells in which AR is expressed, it has a potent effect of inhibiting cell proliferation for cells in which AR is overexpressed. Furthermore, the compound group has, in addition to the antagonist activity for AR, an activity of reducing AR expression, and it exhibits an anti-tumor effect in a cancer-bearing mouse model with castration resistant prostate cancer. As such, the inventors of the present invention found that the compound group is effective as a pharmaceutical agent for treating cancer, and the present invention is completed accordingly.

Accordingly, in an embodiment, the present invention provides the following [1] to [14].

[1] A fused pyrimidine compound represented by the following formula (I):

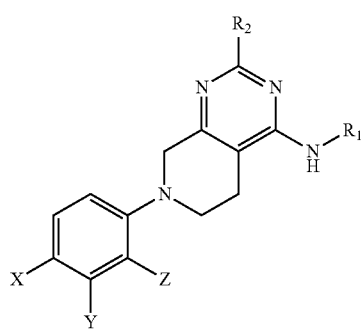

(I)

[in the formula,

X represents a cyano group or a nitro group;

Y represents a halogen atom, a halogeno-$C_{1-3}$ alkyl group, a $C_{1-3}$ alkoxy group, or a $C_{1-3}$ alkyl group;

Z represents a hydrogen atom, a halogen atom, or a $C_{1-3}$ alkyl group;

$R_1$ represents a $C_{6-14}$ aryl group which is substituted with Ra and may be substituted simultaneously with Rb or a 5- or 6-membered heteroaryl group which is substituted with Ra and may be substituted simultaneously with Rb, wherein the Ra and Rb may be bonded to each other to form a fused ring together with the $C_{6-14}$ aryl group or the heteroaryl group; and $R_2$ represents a hydrogen atom, a $C_{1-3}$ alkyl group, or a cyano group, wherein Ra represents a phenyl group, a hydroxy-$C_{1-6}$ alkyl group, a hydroxy-$C_{3-7}$ cycloalkyl group, a hydroxy-heterocycloalkyl group, a $C_{1-6}$ alkoxy group which may be substituted with Rc, an amino-$C_{1-6}$ alkyl group which may be substituted with Rf, a halogeno-$C_{1-3}$ alkoxy group, a $C_{3-7}$ cycloalkylaminosulfonyl group, a $C_{1-3}$ alkylsulfonyl group, a 3- to 7-membered monocyclic heterocycloalkylsulfonyl group, a $C_{1-3}$ alkoxycarbonylamino group which may be substituted with a halogen, a $C_{1-3}$ alkylcarbonylamino group which may be substituted with a halogen, a 3- to 7-membered monocyclic heterocycloalkanecarbonyl group substituted with a hydroxy-$C_{1-3}$ alkyl group, a bicyclic heterocycloalkyl group, or —$(CH_2)_n$—C(=O)—NRdRe;

Rb represents a hydrogen atom, a halogen atom, a $C_{1-3}$ alkyl group which may be substituted with a halogen atom, or a $C_{1-4}$ alkoxy group which may be substituted with a halogen atom;

Rc represents a pyrazolyl group, triazolyl group, or tetrazolyl group which may be substituted or a piperazinyl group which may be substituted with Rf;

Rd and Re each independently represent a hydrogen atom, a $C_{1-3}$ alkyl group, a $C_{2-6}$ alkynyl group, a $C_{1-6}$ alkoxy group, a $C_{3-7}$ cycloalkyl group, a halogeno-$C_{1-3}$ alkyl group, a hydroxy-$C_{1-6}$ alkyl group, a hydroxy-$C_{3-7}$ cycloalkyl group, a hydroxy-$C_{3-7}$ cycloalkyl-$C_{1-6}$ alkyl group, a $C_{1-4}$ alkoxy group, or a $C_{1-6}$ alkyl group substituted with Rg, or NRdRe of the —$(CH_2)_n$—C(=O)—NRdRe may form a ring;

Rf represents a $C_{1-6}$ alkyl group, a $C_{1-6}$ alkylcarbonyl group, a $C_{1-6}$ alkylsulfonyl group, a $C_{1-6}$ alkoxycarbonyl group, or a $C_{1-6}$ alkylaminocarbonyl group;

Rg represents a $C_{1-6}$ alkylpyrazolyl group, a halogeno-$C_{1-3}$ alkylthiazolyl group, an oxadiazolyl group, a halogeno-$C_{1-3}$ alkyloxadiazolyl group, or a $C_{1-6}$ alkoxycarbonylamino group; and n represents an integer of from 0 to 3 (provided that if X is a cyano group, Y is a halogen atom or a halogeno-$C_{1-3}$ alkyl group, $R_2$ is a hydrogen atom, Z is a hydrogen atom, $R_1$ is a $C_{6-14}$ aryl group which is substituted with Ra and may be substituted simultaneously with Rb or a 5- or 6-membered heteroaryl group which is substituted with Ra and may be substituted simultaneously with Rb, and Rb is a hydrogen atom, a halogen atom, or a $C_{1-3}$ alkyl group which may be substituted with a halogen atom, then Ra is a hydroxy-heterocycloalkyl group, a $C_{1-6}$ alkoxy group which may be substituted with Rc (wherein, Rc represents a piperazinyl group which may be substituted with $C_{1-3}$ alkyl, $C_{1-6}$ alkylcarbonyl, $C_{1-6}$ alkoxycarbonyl, or $C_{1-6}$ alkylaminocarbonyl), an amino-$C_{1-6}$ alkyl group which may be substituted with Rf (wherein, Rf is as described above), a halogeno-$C_{1-3}$ alkoxy group, a $C_{1-3}$ alkylsulfonyl group, a bicyclic cycloheteroalkyl group, or —$(CH_2)_n$—C(=O)—NRdRe (wherein, n, Rd, and Re are as described above, provided that if either one of Rd and Re is a halogeno-$C_{1-3}$ alkyl group, a hydroxy-$C_{1-6}$ alkyl group, a hydroxy-$C_{3-7}$ cycloalkyl group, a hydroxy-$C_{3-7}$ cycloalkyl-$C_{1-6}$ alkyl group, or a $C_{1-6}$ alkyl group substituted with $C_{1-6}$ alkylpyrazolyl, halogeno-$C_{1-3}$ alkylthiazolyl, oxadiazolyl, or halogeno-$C_{1-3}$ alkyloxadiazolyl, then the other is not a hydrogen atom))]

or a pharmaceutically acceptable salt thereof.

[2] The compound according to [1] or a pharmaceutically acceptable salt thereof, wherein Z is a hydrogen atom or a fluorine atom.

[3] The compound according to [1] or [2] or a pharmaceutically acceptable salt thereof, wherein $R_2$ is a hydrogen atom, a methyl group, or a cyano group.

[4] The compound according to any one of [1] to [3] or a pharmaceutically acceptable salt thereof, wherein Y is a chlorine atom, a bromine atom, a trifluoromethyl group, a methoxy group, an isopropoxy group, or a methyl group.

[5] The compound according to any one of [1] to [4] or a pharmaceutically acceptable salt thereof, wherein n is 0.

[6] The compound according to any one of [1] to [5] or a pharmaceutically acceptable salt thereof, wherein $R_1$ is a phenyl group substituted with the Ra and the Rb, a pyridinyl group substituted with the Ra and the Rb, or a pyridazinyl group substituted with the Ra and the Rb.

[7] The compound according to any one of [1] to [6] or a pharmaceutically acceptable salt thereof, wherein Ra represents a phenyl group, a hydroxy-ethyl group, a hydroxy-isopropyl group, a hydroxy-oxetanyl group, a methoxy group, a trifluoromethoxy group, a 2-oxa-6-azaspiro[3.3]heptyl group, —(CH$_2$)$_n$—C(=O)—NRdRe, or an n-propoxy group substituted with a piperazinyl group which may be substituted with acetyl, mesyl, tert-butoxycarbonyl, or methyl.

[8] The compound according to any one of [1] to [7] or a pharmaceutically acceptable salt thereof, wherein $R_1$ is selected from the group consisting of the following groups:

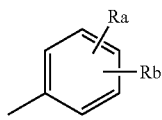

(in the formula, Ra represents a phenyl group, a $C_{1-6}$ alkoxy group which may be substituted with the Rc, an amino-$C_{1-6}$ alkyl group which may be substituted with the Rf, a halogeno-$C_{1-3}$ alkoxy group, or a bicyclic heterocycloalkyl group, and Rb represents a hydrogen atom, a halogen atom, a $C_{1-3}$ alkyl group which may be substituted with a halogen atom, or a $C_{1-4}$ alkoxy group which may be substituted with a halogen atom; or Ra is the amino-$C_{1-6}$ alkyl group which may be substituted with Rf, and Rb is a $C_{1-3}$ alkyl group, and the Ra and Rb are bonded to each other to form a fused ring together with the ring on which they are substituted);

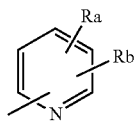

(in the formula,
Ra represents a hydroxy-$C_{1-6}$ alkyl group, a hydroxy-heterocycloalkyl group, or the —(CH$_2$)$_n$—C(=O)—NRdRe, and
Rb represents a hydrogen atom or a halogen atom); and

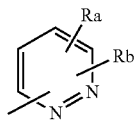

(in the formula,
Ra represents the —(CH$_2$)$_n$—C(=O)—NRdRe, and
Rb represents a hydrogen atom).

[9] The compound according to [11] or a pharmaceutically acceptable salt thereof, wherein X represents a cyano group or a nitro group;
Y represents a halogen atom, a halogeno-$C_{1-3}$ alkyl group, a $C_{1-3}$ alkoxy group, or a $C_{1-3}$ alkyl group;
Z represents a hydrogen atom or a halogen atom;
$R_1$ is a substituent selected from the group consisting of the following groups:

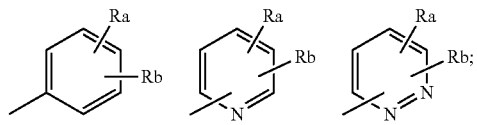

a cyano group;
Ra represents a phenyl group, a hydroxy-$C_{1-3}$ alkyl group, a hydroxy-heterocycloalkyl group, a $C_{1-6}$ alkoxy group which may be substituted with Rc, an amino-$C_{1-6}$ alkyl group which may be substituted with Rf, a halogeno-$C_{1-3}$ alkoxy group, a bicyclic heterocycloalkyl group, or —(CH$_2$)$_n$—C(=O)—NRdRe;
Rb represents a hydrogen atom, a halogen atom, a $C_{1-3}$ alkyl group which may be substituted with a halogen atom, or a $C_{1-4}$ alkoxy group which may be substituted with a halogen atom;
or Ra and Rb are bonded to each other to form a fused ring together with the ring on which they are substituted;
Rc represents a piperazinyl group which may be substituted with Rf;
Rd and Re each independently represent a hydrogen atom, a $C_{1-3}$ alkyl group, a $C_{2-6}$ alkynyl group, a $C_{1-6}$ alkoxy group, a $C_{3-7}$ cycloalkyl group, a halogeno-$C_{1-3}$ alkyl group, or a $C_{1-6}$ alkyl group substituted with Rg;
or NRdRe forms a 3- to 7-membered nitrogen-containing heterocyclic ring;
Rf represents a $C_{1-6}$ alkyl group, a $C_{1-6}$ alkylcarbonyl group, a $C_{1-6}$ alkylsulfonyl group, a $C_{1-6}$ alkoxycarbonyl group, or a $C_{1-6}$ alkylaminocarbonyl group;
Rg represents a $C_{1-6}$ alkoxycarbonylamino group; and
n represents an integer of 0 or 1.

[10] The compound according to [9] or a pharmaceutically acceptable salt thereof, wherein
X represents a cyano group or a nitro group;
Y represents a chlorine atom, a bromine atom, a trifluoromethyl group, a methoxy group, an isopropoxy group, or a methyl group;
Z represents a hydrogen atom or a fluorine atom;
$R_1$ is a substituent selected from the group consisting of the following groups:

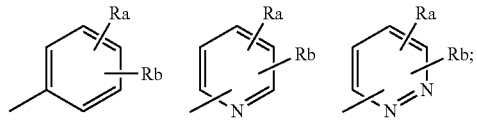

$R_2$ represents a hydrogen atom, a methyl group, or a cyano group;
Ra represents a phenyl group, a hydroxy-ethyl group, a hydroxy-isopropyl group, a hydroxy-oxetanyl group, a methoxy group, a trifluoromethoxy group, a 2-oxa-6-azaspiro[3.3]heptyl group, —(CH$_2$)$_n$—C(=O)—NRdRe, or an n-propoxy group substituted with a piperazinyl group which may be substituted with acetyl, tert-butoxycarbonyl, mesyl, or methyl;

Rb represents a hydrogen atom, a fluorine atom, a chlorine atom, a methyl group, a trifluoromethyl group, or a methoxy group;

or Ra and Rb are bonded to each other to form a substituted or unsubstituted tetrahydroisoquinolinyl group or isoindolinyl group together with the ring on which they are substituted;

either one of Rd and Re represents a methyl group, an ethyl group, a propynyl group, a cyclopropyl group, a trifluoroethyl group, a tert-butoxy group, or an ethyl group substituted with tert-butoxycarbonylamino, and the other represents a hydrogen atom or a methyl group;

or NRdRe forms azepane; and n is 0.

[11] The compound according to [1] or a pharmaceutically acceptable salt thereof, which is selected from the group consisting of the following compounds (1) to (48):

(1) 6-((7-(3-chloro-4-cyanophenyl)-5,6,7,8-tetrahydropyrido[3,4-d]pyrimidin-4-yl)amino)-N-ethyl-2-fluoronicotinamide;

(2) 6-((7-(3-chloro-4-cyanophenyl)-5,6,7,8-tetrahydropyrido[3,4-d]pyrimidin-4-yl)amino)-2-fluoro-N-methylnicotinamide;

(3) 6-((7-(4-cyano-3-(trifluoromethyl)phenyl)-5,6,7,8-tetrahydropyrido[3,4-d]pyrimidin-4-yl)amino)-2-fluoro-N-methylnicotinamide;

(4) 6-((7-(4-cyano-3-(trifluoromethyl)phenyl)-5,6,7,8-tetrahydropyrido[3,4-d]pyrimidin-4-yl)amino)-N-ethyl-2-fluoronicotinamide;

(5) 6-((7-(4-cyano-3-(trifluoromethyl)phenyl)-5,6,7,8-tetrahydropyrido[3,4-d]pyrimidin-4-yl)amino)-N-ethylnicotinamide;

(6) 4-(4-((5-(azepane-1-carbonyl)pyridin-2-yl)amino)-5,6-dihydropyrido[3,4-d]pyrimidin-7(8H)-yl)-2-(trifluoromethyl)benzonitrile;

(7) N-(tert-butoxy)-6-((7-(4-cyano-3-(trifluoromethyl)phenyl)-5,6,7,8-tetrahydropyrido[3,4-d]pyrimidin-4-yl)amino)nicotinamide;

(8) tert-butyl(2-(6-((7-(4-cyano-3-(trifluoromethyl)phenyl)-5,6,7,8-tetrahydropyrido[3,4-d]pyrimidin-4-yl)amino)pyridazine-3-carboxamido)ethyl)carbamate;

(9) 6-((7-(4-cyano-3-(trifluoromethyl)phenyl)-5,6,7,8-tetrahydropyrido[3,4-d]pyrimidin-4-yl)amino)-N-cyclopropylpyridazine-3-carboxamide;

(10) 6-((7-(4-cyano-3-(trifluoromethyl)phenyl)-5,6,7,8-tetrahydropyrido[3,4-d]pyrimidin-4-yl)amino)-N-ethylpyridazine-3-carboxamide;

(11) 6-((7-(4-cyano-3-(trifluoromethyl)phenyl)-5,6,7,8-tetrahydropyrido[3,4-d]pyrimidin-4-yl)amino)-N-(prop-2-yn-1-yl)pyridazine-3-carboxamide;

(12) N-ethyl-2-fluoro-6-((7-(4-nitro-3-(trifluoromethyl)phenyl)-5,6,7,8-tetrahydropyrido[3,4-d]pyrimidin-4-yl)amino)nicotinamide;

(13) 2-(6-((7-(3-chloro-4-nitrophenyl)-5,6,7,8-tetrahydropyrido[3,4-d]pyrimidin-4-yl)amino)pyridin-3-yl)propan-2-ol;

(14) 2-(6-((7-(4-nitro-3-(trifluoromethyl)phenyl)-5,6,7,8-tetrahydropyrido[3,4-d]pyrimidin-4-yl)amino)pyridin-3-yl)propan-2-ol;

(15) 2-(6-((7-(3-methoxy-4-nitrophenyl)-5,6,7,8-tetrahydropyrido[3,4-d]pyrimidin-4-yl)amino)pyridin-3-yl)propan-2-ol;

(16) 2-(6-((7-(3-methyl-4-nitrophenyl)-5,6,7,8-tetrahydropyrido[3,4-d]pyrimidin-4-yl)amino)pyridin-3-yl)propan-2-ol;

(17) 2-(6-((7-(3-bromo-4-nitrophenyl)-5,6,7,8-tetrahydropyrido[3,4-d]pyrimidin-4-yl)amino)pyridin-3-yl)propan-2-ol;

(18) 2-(6-((7-(3-chloro-2-fluoro-4-nitrophenyl)-5,6,7,8-tetrahydropyrido[3,4-d]pyrimidin-4-yl)amino)pyridin-3-yl)propan-2-ol;

(19) 2-(6-((7-(3-isopropoxy-4-nitrophenyl)-5,6,7,8-tetrahydropyrido[3,4-d]pyrimidin-4-yl)amino)pyridin-3-yl)propan-2-ol;

(20) 4-(4-((5-(2-hydroxypropan-2-yl)pyridin-2-yl)amino)-5,6-dihydropyrido[3,4-d]pyrimidin-7(8H)-yl)-2-methylbenzonitrile;

(21) N-(3-fluoro-4-methoxyphenyl)-7-(4-nitro-3-(trifluoromethyl)phenyl)-5,6,7,8-tetrahydropyrido[3,4-d]pyrimidin-4-amine;

(22) 7-(3-chloro-4-nitrophenyl)-N-(3-fluoro-4-methoxyphenyl)-5,6,7,8-tetrahydropyrido[3,4-d]pyrimidin-4-amine;

(23) 4-(4-((5-(2-hydroxypropan-2-yl)pyridin-2-yl)amino)-5,6-dihydropyrido[3,4-d]pyrimidin-7(8H)-yl)-2-methoxybenzonitrile;

(24) 6-((7-(4-nitro-3-(trifluoromethyl)phenyl)-5,6,7,8-tetrahydropyrido[3,4-d]pyrimidin-4-yl)amino)-N-(2,2,2-trifluoroethyl)pyridazine-3-carboxamide;

(25) N-(6-methoxypyridin-3-yl)-7-(4-nitro-3-(trifluoromethyl)phenyl)-5,6,7,8-tetrahydropyrido[3,4-d]pyrimidin-4-amine;

(26) 4-(4-((3,4-dimethoxyphenyl)amino)-5,6-dihydropyrido[3,4-d]pyrimidin-7(8H)-yl)-2-(trifluoromethyl)benzonitrile;

(27) 4-(4-((4-(trifluoromethoxy)phenyl)amino)-5,6-dihydropyrido[3,4-d]pyrimidin-7(8H)-yl)-2-(trifluoromethyl)benzonitrile;

(28) 4-(4-((4-(2-oxa-6-azaspiro[3.3]heptan-6-yl)phenyl)amino)-5,6-dihydropyrido[3,4-d]pyrimidin-7(8H)-yl)-2-chlorobenzonitrile;

(29) tert-butyl 5-((7-(3-chloro-4-cyanophenyl)-5,6,7,8-tetrahydropyrido[3,4-d]pyrimidin-4-yl)amino)isoindoline-2-carboxylate;

(30) tert-butyl 4-(3-(2-chloro-4-((7-(4-nitro-3-(trifluoromethyl)phenyl)-5,6,7,8-tetrahydropyrido[3,4-d]pyrimidin-4-yl)amino)phenoxy)propyl)piperazine-1-carboxylate;

(31) N-(3,4-dimethoxyphenyl)-7-(4-nitro-3-(trifluoromethyl)phenyl)-5,6,7,8-tetrahydropyrido[3,4-d]pyrimidin-4-amine;

(32) tert-butyl 7-((7-(4-nitro-3-(trifluoromethyl)phenyl)-5,6,7,8-tetrahydropyrido[3,4-d]pyrimidin-4-yl)amino)-3,4-dihydroisoquinoline-2(1H)-carboxylate;

(33) N-(3-methyl-4-(2-oxa-6-azaspiro[3.3]heptan-6-yl)phenyl)-7-(4-nitro-3-(trifluoromethyl)phenyl)-5,6,7,8-tetrahydropyrido[3,4-d]pyrimidin-4-amine;

(34) N-([1,1'-biphenyl]-3-yl)-7-(4-nitro-3-(trifluoromethyl)phenyl)-5,6,7,8-tetrahydropyrido[3,4-d]pyrimidin-4-amine;

(35) 2-chloro-4-(4-((6-fluoro-5-(3-hydroxyoxetan-3-yl)pyridin-2-yl)amino)-5,6-dihydropyrido[3,4-d]pyrimidin-7(8H)-yl)benzonitrile;

(36) tert-butyl 7-((7-(3-chloro-4-cyanophenyl)-5,6,7,8-tetrahydropyrido[3,4-d]pyrimidin-4-yl)amino)-3,4-dihydroisoquinolin-2(1H)-carboxylate;

(37) 2-chloro-4-(4-((1,2,3,4-tetrahydroisoquinolin-7-yl)amino)-5,6-dihydropyrido[3,4-d]pyrimidin-7(8H)-yl)benzonitrile;

(38) 2-chloro-4-(4-((4-(3-(piperazin-1-yl)propoxy)-3-(trifluoromethyl)phenyl)amino)-5,6-dihydropyrido[3,4-d]pyrimidin-7(8H)-yl)benzonitrile;

(39) 1-(4-(3-(2-chloro-4-((7-(4-nitro-3-(trifluoromethyl)phenyl)-5,6,7,8-tetrahydropyrido[3,4-d]pyrimidin-4-yl)amino) phenoxy)propyl)piperazin-1-yl)ethanone;
(40) N-(3-chloro-4-(3-(4-(methylsulfonyl)piperazin-1-yl)propoxy)phenyl)-7-(4-nitro-3-(trifluoromethyl)phenyl)-5,6,7,8-tetrahydropyrido[3,4-d]pyrimidin-4-amine;
(41) N-(3-chloro-4-(3-(4-methylpiperazin-1-yl)propoxy)phenyl)-7-(4-nitro-3-(trifluoromethyl)phenyl)-5,6,7,8-tetrahydropyrido[3,4-d]pyrimidin-4-amine;
(42) 4-(4-((4-(3-(4-acetylpiperazin-1-yl)propoxy)-3-chlorophenyl)amino)-5,6-dihydropyrido[3,4-d]pyrimidin-7(8H)-yl)-2-chlorobenzonitrile;
(43) 4-(4-((4-(3-(4-acetylpiperazin-1-yl)propoxy)-3-(trifluoromethyl)phenyl)amino)-5,6-dihydropyrido[3,4-d]pyrimidin-7(8H)-yl)-2-chlorobenzonitrile;
(44) 4-(4-((4-(3-(4-acetylpiperazin-1-yl)propoxy)-2-(trifluoromethyl)phenyl)amino)-5,6-dihydropyrido[3,4-d]pyrimidin-7(8H)-yl)-2-(trifluoromethyl)benzonitrile;
(45) 1-(4-(3-(4-((7-(4-nitro-3-(trifluoromethyl)phenyl)-5,6,7,8-tetrahydropyrido[3,4-d]pyrimidin-4-yl)amino)-2-(trifluoromethyl)phenoxy)propyl)piperazin-1-yl)ethanone;
(46) 1-(4-(3-(4-((7-(4-nitro-3-(trifluoromethyl)phenyl)-5,6,7,8-tetrahydropyrido[3,4-d]pyrimidin-4-yl)amino) phenoxy) propyl)piperazin-1-yl) ethanone;
(47) 7-(4-cyano-3-(trifluoromethyl)phenyl)-4-((4-methoxyphenyl)amino)-5,6,7,8-tetrahydropyrido[3,4-d]pyrimidine-2-carbonitrile; and
(48) 4-(4-((4-methoxyphenyl)amino)-2-methyl-5,6-dihydropyrido[3,4-d]pyrimidin-7(8H)-yl)-2-(trifluoromethyl)benzonitrile.

An [12] anti-androgen agent comprising, as an active ingredient, the fused pyrimidine compound according to any one of [1] to [11] or a pharmaceutically acceptable salt thereof.
[13] An anti-tumor agent comprising, as an active ingredient, the fused pyrimidine compound according to any one of [1] to [11] or a pharmaceutically acceptable salt thereof.
[14] A pharmaceutical composition comprising the fused pyrimidine compound according to any one of [1] to [11] or a pharmaceutically acceptable salt thereof, and a pharmaceutically acceptable carrier.

Effects of the Invention

The novel fused pyrimidine compound of the present invention or a salt thereof exhibits an antagonist activity against an androgen receptor (AR), and is effective for a disorder related with AR activation. Examples of a disorder related with AR activation include tumor, metastatic bone disease, prostatic hyperplasia, acne vulgaris, seborrhea, hypertrichosis, androgenetic alopecia, precocious puberty, and virillizing syndrome. Examples of the tumor include prostate cancer, breast cancer, ovarian cancer, bladder cancer, uterine cancer, pancreatic cancer, and hepatocellular cancer.

DESCRIPTION OF EMBODIMENTS

As described herein, examples of the "halogen atom" include a fluorine atom, a chlorine atom, a bromine atom, and an iodine atom, and it is preferably a fluorine atom, a chlorine atom, or a bromine atom.

As described herein, the "$C_{1-6}$ alkyl group" indicates a linear or branched alkyl group having 1 to 6 carbon atoms, examples thereof include a methyl group, an ethyl group, an n-propyl group, an isopropyl group, an n-butyl group, a 2-methylpropyl group, a sec-butyl group, a tert-butyl group, an n-pentyl group, an isopentyl group, a tert-pentyl group, a neopentyl group, an n-hexyl group, and a thexyl group, and it is preferably a linear or branched alkyl group having 1 to 4 carbon atoms, more preferably a methyl group, an ethyl group, an n-propyl group, an isopropyl group, an n-butyl group, a 2-methylpropyl group, a sec-butyl group, or a tert-butyl group. Furthermore, as described herein, the "$C_{1-4}$ alkyl group" and "$C_{1-3}$ alkyl group" each indicates an alkyl group having 1 to 4 carbon atoms and an alkyl group having 1 to 3 carbon atoms among the aforementioned "$C_{1-6}$ alkyl group".

As described herein, the "$C_{2-6}$ alkynyl group" indicates an alkynyl group having 2 to 6 carbon atoms, examples thereof include an ethynyl group and a propynyl group, and it is preferably an alkynyl group having 2 to 4 carbon atoms, more preferably a propynyl group. The "$C_{2-4}$ alkynyl group" as described herein indicates an alkynyl group having 2 to 4 carbon atoms among the aforementioned "$C_{1-6}$ alkynyl groups".

As described herein, the "halogeno-$C_{1-3}$ alkyl group" indicates the aforementioned $C_{1-3}$ alkyl group which is substituted with 1 to 7 halogen atoms that are described above. Examples of the "halogeno-$C_{1-3}$ alkyl group" include a fluoro-$C_{1-3}$ alkyl group or a chloro-$C_{1-3}$ alkyl group, such as a fluoromethyl group, a difluoromethyl group, a trifluoromethyl group, a trichloromethyl group, a 2-fluoroethyl group, a 2,2-difluoroethyl group, a 2,2,2-trifluoroethyl group, a 2,2,2-trichloroethyl group, a monofluoro-n-propyl group, a perfluoro-n-propyl group, and a perfluoroisopropyl group, and it is preferably a $C_{1-3}$ alkyl group substituted with 1 to 3 halogen atoms, more preferably $C_{1-3}$ alkyl group substituted with 1 to 3 fluorine atoms.

As described herein, the "$C_{G-14}$ aryl group" indicates an aryl group having 6 to 14 carbon atoms, examples thereof include a phenyl group, a naphthyl group, an anthracenyl group, a phenanthryl group, and a fluorenyl group, and it is preferably an aryl group having 6 to 10 carbon atoms and more preferably a phenyl group.

As described herein, the "heteroaryl group" indicates an aromatic monocyclic or polycyclic group having 1 to 4 hetero atoms independently selected from any one of oxygen, nitrogen, and sulfur. Examples of the heteroaryl group include a furyl group, a thienyl group, a pyrrolyl group, an imidazolyl group, a pyrazolyl group, a triazolyl group, a tetrazolyl group, an oxazolyl group, an oxadiazolyl group, a triazinyl group, a thiazolyl group, a thiadiazolyl group, an isoxazolyl group, an isothiazolyl group, a pyridinyl group, a pyrazinyl group, a pyrimidinyl group, a pyridazinyl group, an indolinyl group, a quinolinyl group, an isoquinolinyl group, a benzo[b]thienyl group, a benzimidazolyl group, a benzothiazolyl group, and a benzoxazolyl group. The heteroaryl group is preferably an aromatic monocyclic group having 1 to 4 hetero atoms independently selected from oxygen, nitrogen, and sulfur; more preferably an aromatic monocyclic group having 1 to 3 nitrogen atoms; and even more preferably a pyridinyl group, a pyridazinyl group, or a pyrimidinyl group.

As described herein, the "hydroxy-$C_{1-6}$ alkyl group" indicates the aforementioned $C_{1-6}$ alkyl group which is substituted with 1 to 3 hydroxyl groups. Examples of the "hydroxy-$C_{1-6}$ alkyl group" include a hydroxymethyl group, a 1-hydroxy-ethyl group, a 1,2-dihydroxy-ethyl group, a 1-hydroxypropyl group, a 1,2-dihydroxypropyl group, a 1,2,3-trihydroxypropyl group, a 1-hydroxybutyl group, a 2-hydroxypropan-2-yl group, and a 2-hydroxy-2-methylpropyl group. The hydroxy-$C_{1-3}$ alkyl group is preferably $C_{1-6}$ alkyl group substituted with one hydroxyl group.

As described herein, the "amino-$C_{1-6}$ alkyl group" is the aforementioned $C_{1-6}$ alkyl group substituted with 1 to 3 amino groups, preferably the aforementioned $C_{1-3}$ alkyl group substituted with 1 to 3 amino groups. Examples of the "amino-$C_{1-6}$ alkyl group" include an aminomethyl group, a 1-aminoethyl group, a 2-aminoethyl group, and a 1-aminopropyl group, and it is preferably a $C_{1-6}$ alkyl group substituted with one amino group, more preferably a $C_{1-3}$ alkyl group substituted with one amino group.

As described herein, the "$C_{3-7}$ cycloalkyl group" indicates a cyclic alkyl group having 3 to 7 carbon atoms, examples thereof include a cyclopropyl group, a cyclobutyl group, a cyclopentyl group, a cyclohexyl group, and a cycloheptyl group, and it is preferably a cyclopropyl group.

As described herein, the "hydroxy-$C_{3-7}$ cycloalkyl group" indicates the aforementioned $C_{3-7}$ cycloalkyl group which is substituted with 1 to 3 hydroxyl groups. Examples of the "hydroxy-$C_{3-7}$ cycloalkyl group" include a 1-hydroxycyclopropyl group, a 2-hydroxycyclopropyl group, a 1,2-dihydroxycyclopropyl group, a 1,2,3-trihydroxycyclopropyl group, a 1-hydroxycyclobutyl group, a 1-hydroxycyclopentyl group, a 1-hydroxycyclohexyl group, or a 4-hydroxycyclohexyl group, and it is preferably a $C_{3-7}$ cycloalkyl group substituted with one hydroxyl group.

As described herein, the "heterocycloalkyl group" indicates a 3- to 7-membered monocyclic or bicyclic alkyl group having, instead of carbon, 1 to 3 hetero atoms independently selected from oxygen, nitrogen, and sulfur, among the cyclic alkyl groups. Examples of the "heterocycloalkyl group" include an aziridinyl group, an azetidinyl group, a pyrrolidinyl group, an oxazolidinyl group, a thiazolidinyl group, an oxetanyl group, a tetrahydrofuranyl group, a tetrahydrothiophenyl group, a piperidinyl group, a piperazinyl group, a morpholino group, a thiomorpholino group, an azepanyl group, a diazepanyl group, an oxazepanyl group, and a 2-oxa-6-azaspiro[3.3]heptyl group, and it is preferably a 3- to 7-membered monocyclic or bicyclic alkyl group having, instead of carbon, 1 to 3 hetero atoms independently selected from oxygen and nitrogen.

As described herein, the "hydroxy-heterocycloalkyl group" indicates the aforementioned heterocycloalkyl group substituted with 1 to 3 hydroxyl groups. Examples of the "hydroxy-heterocycloalkyl group" include an oxetanyl group substituted with 1 to 3 hydroxyl groups, a tetrahydrofuranyl group substituted with 1 to 3 hydroxyl groups, and a piperidinyl group substituted with 1 to 3 hydroxyl groups, and preferably an oxetanyl group substituted with 1 to 3 hydroxyl groups (hydroxy-oxetanyl group), such as a 3-hydroxyoxetan-3-yl group, and it is preferably a 3- to 7-membered monocyclic alkyl group having, instead of carbon, 1 to 3 hetero atoms independently selected from oxygen and nitrogen, which is substituted with one hydroxyl group.

As described herein, the "$C_{1-6}$ alkylcarbonyl group" indicates a carbonyl group substituted with a linear or branched alkyl group having 1 to 6 carbon atoms, such as a methylcarbonyl (acetyl) group, an ethylcarbonyl group, an n-propylcarbonyl group, an isopropylcarbonyl group, an n-butylcarbonyl group, and a tert-butylcarbonyl group, and preferably a methylcarbonyl (acetyl) group. The "$C_{1-3}$ alkylcarbonyl group" as described herein indicates a carbonyl group substituted with an alkyl group having 1 to 3 carbon atoms among the aforementioned "$C_{1-6}$ alkylcarbonyl groups".

As described herein, the "$C_{1-6}$ alkylaminocarbonyl group" indicates a carbonyl group having an amino group substituted with a linear or branched alkyl group having 1 to 6 carbon atoms. Examples of the "$C_{1-6}$ alkylaminocarbonyl group" include a methylaminocarbonyl group, an ethylaminocarbonyl group, an n-propylaminocarbonyl group, an isopropylaminocarbonyl group, an n-butylaminocarbonyl group, and a tert-butylaminocarbonyl group, and it is preferably a carbonyl group having an amino group substituted with a linear or branched alkyl group having 1 to 3 carbon atoms.

As described herein, the "$C_1$-6 alkylsulfonyl group" indicates a sulfonyl group substituted with a linear or branched alkyl group having 1 to 6 carbon atoms, examples thereof include a methylsulfonyl (mesyl) group, an ethylsulfonyl group, an n-propylsulfonyl group, an isopropylsulfonyl group, an n-butylsulfonyl group, and a tert-butylsulfonyl group, and it is preferably a methylsulfonyl (mesyl) group. The "$C_{1-3}$ alkylsulfonyl group" as described herein indicates a sulfonyl group substituted with an alkyl group having 1 to 3 carbon atoms among the aforementioned "$C_{1-6}$ alkylsulfonyl groups".

As described herein, the "$C_{3-7}$ cycloalkylaminosulfonyl group" indicates a sulfonyl group having an amino group substituted with one of the aforementioned $C_{3-7}$ cycloalkyl groups. Examples of the "$C_{3-7}$ cycloalkylaminosulfonyl group" include a cyclopropylaminosulfonyl group, a cyclobutylaminosulfonyl group, or a cyclopentylaminosulfonyl group, and it is preferably a cyclopropylaminosulfonyl group.

As described herein, the "heterocycloalkylsulfonyl group" is a sulfonyl group substituted with the aforementioned heterocycloalkyl group. Examples of the "heterocycloalkylsulfonyl group" include a piperidin-1-ylsulfonyl group, a morpholinosulfonyl group, a 1,4-thioazepan-4-ylsulfonyl group, and a 1,4-oxazepanylsulfonyl group, and it is preferably a sulfonyl group substituted with a 3- to 7-membered monocyclic alkyl group having, instead of carbon, 1 to 3 hetero atoms independently selected from oxygen, nitrogen, and sulfur.

As described herein, the "$C_{1-6}$ alkoxy group" indicates a linear or branched alkoxy group having 1 to 6 carbon atoms, examples thereof include a methoxy group, an ethoxy group, an n-propoxy group, an isopropoxy group, an n-butoxy group, a 2-methylpropoxy group (isobutoxy group), a sec-butoxy group, a tert-butoxy group, an n-pentyloxy group, an isopentyloxy group, a tert-pentyloxy group, a neopentyloxy group, an n-hexyloxy group, and a thexyloxy group, and it is preferably a linear or branched alkoxy group having 1 to 4 carbon atoms. Furthermore, as described herein, the "$C_{1-4}$ alkoxy group" and "$C_{1-3}$ alkoxy group" each indicates an alkoxy group having 1 to 4 carbon atoms and an alkoxy group having 1 to 3 carbon atoms among the aforementioned "$C_{1-6}$ alkoxy group".

As described herein, the "$C_{1-6}$ alkoxycarbonyl group" indicates a carbonyl group substituted with a linear or branched alkoxy group having 1 to 6 carbon atoms, examples thereof include a methoxycarbonyl group, an ethoxycarbonyl group, an n-propoxycarbonyl group, an isopropoxycarbonyl group, an n-butoxycarbonyl group, and a tert-butoxycarbonyl group, and it is preferably a tert-butoxycarbonyl group. The "$C_{1-3}$ alkoxycarbonyl group" as described herein indicates a carbonyl group substituted with an alkoxy group having 1 to 3 carbon atoms among the aforementioned "$C_{1-6}$ alkoxycarbonyl groups".

As described herein, the "halogeno-$C_{1-3}$ alkoxy group" indicates the aforementioned $C_{1-3}$ alkoxy group which is substituted with 1 to 7 halogen atoms that are described above. Examples of the "halogeno-$C_{1-3}$ alkoxy group" include a fluoro-$C_{1-3}$ alkoxy group or a chloro-$C_{1-3}$ alkoxy group, such as a fluoromethoxy group, a difluoromethoxy group, a trifluoromethoxy group, a trichloromethoxy group, a 2-fluoroethoxy group, a 2,2-difluoroethoxy group, a 2,2,2-trifluoroethoxy group, a 2,2,2-trichloroethoxy group, a monofluoro-n-propoxy group, a perfluoro-n-propoxy group, and a perfluoroisopropoxy group, and it is preferably a $C_{1-3}$ alkoxy group substituted with 1 to 3 of the aforementioned halogen atoms, more preferably a $C_{1-3}$ alkoxy group substituted with 1 to 3 fluorine atoms.

As described herein, the "$C_{1-3}$ alkylcarbonylamino group" indicates an amino group substituted with one of the aforementioned $C_{1-3}$ alkylcarbonyl groups, and the "$C_{1-3}$ alkylcarbonyl group" indicates a carbonyl group substituted with the aforementioned $C_{1-3}$ alkyl group. Examples of the "$C_{1-3}$ alkylcarbonylamino group" include a methylcarbonylamino group and an ethylcarbonylamino group, and is preferably a methylcarbonylamino group.

As described herein, the "$C_{1-6}$ alkoxycarbonylamino group" indicates an amino group substituted with one of the aforementioned $C_{1-6}$ alkoxycarbonyl groups, examples thereof include a methoxycarbonylamino group, an ethoxycarbonylamino group, an n-propoxycarbonylamino group, an isopropoxycarbonylamino group, an n-butoxycarbonylamino group, and a tert-butoxycarbonylamino group, and it is preferably a tert-butoxycarbonylamino group. As described herein, the "$C_{1-3}$ alkoxycarbonylamino group" indicates an amino group substituted with one of the aforementioned $C_{1-3}$ alkoxycarbonyl groups.

As described herein, the "halogeno-$C_{1-3}$ alkoxycarbonylamino group" indicates an amino group which is substituted with one halogeno-$C_{1-3}$ alkoxycarbonyl group, and the "halogeno-$C_{1-3}$ alkoxycarbonyl group" indicates a carbonyl group which is substituted with the aforementioned halogeno-$C_{1-3}$ alkoxy group. Examples of the "halogeno-$C_{1-3}$ alkoxycarbonylamino group" include a trifluoromethoxycarbonylamino group, a trichloromethoxycarbonylamino group, a 2-fluoroethoxycarbonylamino group, a 2,2-difluoroethoxycarbonylamino group, or a 2,2,2-trifluoroethoxycarbonylamino group, and it is preferably a $C_{1-3}$ alkoxycarbonylamino group substituted with 1 to 3 halogen atoms, more preferably a $C_{1-3}$ alkoxycarbonylamino group substituted with 1 to 3 fluorine atoms.

As described herein, the "halogeno-$C_{1-3}$ alkylcarbonylamino group" indicates an amino group which is substituted with one halogeno-$C_{1-3}$ alkylcarbonyl group, and the "halogeno-$C_{1-3}$ alkylcarbonyl group" indicates a carbonyl group which is substituted with the aforementioned halogeno-$C_{1-3}$ alkyl group. Examples of the "halogeno-$C_{1-3}$ alkylcarbonylamino group" include a trifluoromethylcarbonylamino group, a trichloromethylcarbonylamino group, a 2-fluoroethylcarbonylamino group, a 2,2-difluoroethylcarbonylamino group, or a 2,2,2-trifluoroethylcarbonylamino group, and it is preferably a $C_{1-3}$ alkylcarbonylamino group substituted with 1 to 3 halogen atoms, more preferably a $C_{1-3}$ alkylcarbonylamino group substituted with 1 to 3 fluorine atoms.

As described herein, the "heterocycloalkanecarbonyl group" indicates a carbonyl group which is substituted with the aforementioned heterocycloalkyl group. Examples of the "heterocycloalkanecarbonyl group" include a piperidine-1-carbonyl group, a piperazine-1-carbonyl group, an azetidine-1-carbonyl group, or a morpholine-4-carbonyl group, and it is preferably a carbonyl group substituted with a 3- to 7-membered monocyclic alkyl group having, instead of carbon, 1 to 3 hetero atoms independently selected from oxygen, nitrogen, and sulfur.

As described herein, the "$C_{1-6}$ alkylpyrazolyl group" indicates a pyrazolyl group which is substituted with one $C_{1-6}$ alkyl group described above. Examples of the "$C_{1-6}$ alkylpyrazolyl group" include a 1-methyl-1H-pyrazol-5-yl group, a 1-ethyl-1H-pyrazol-5-yl group, a 1-propyl-1H-pyrazol-5-yl group, a 1-methyl-1H-pyrazol-3-yl group, and a 1-methyl-1H-pyrazol-4-yl group, and it is preferably a pyrazolyl group substituted with one methyl group.

As described herein, the "hydroxy-$C_{3-7}$ cycloalkyl-$C_{1-6}$ alkyl group" indicates the aforementioned $C_{1-6}$ alkyl group which is substituted with one hydroxy-$C_{3-7}$ cycloalkyl group described above. Examples of the "hydroxy-$C_{3-7}$ cycloalkyl-$C_{1-6}$ alkyl group" include a (1-hydroxycyclopropyl)methyl group, a (1-hydroxycyclobutyl)methyl group, a 2-(1-hydroxycyclopropyl)ethyl group, a (1,2-dihydroxycyclopropyl)methyl group, and a (1,2,3-trihydroxycyclopropyl)methyl group, and it is preferably a (1-hydroxycyclopropyl)methyl group.

As described herein, the "halogeno-$C_{1-3}$ alkylthiazolyl group" indicates a thiazolyl group substituted with one of the aforementioned halogeno-$C_{1-3}$ alkyl groups, examples thereof include a 4-(trifluoromethyl)thiazol-2-yl group, a 5-(trifluoromethyl)thiazol-2-yl group, a 4-(trichloromethyl)thiazol-2-yl group, and a 4-(2,2,2-trifluoroethyl)thiazol-2-yl group, and it is preferably a thiazolyl group substituted with one $C_{1-3}$ alkyl group which is substituted with 1 to 3 halogen atoms, and is more preferably a thiazolyl group substituted with one $C_{1-3}$ alkyl group which is substituted with 1 to 3 fluorine atoms.

As described herein, the "halogeno-$C_{1-3}$ alkyloxadiazolyl group" indicates an oxadiazolyl group substituted with one of the aforementioned halogeno-$C_{1-3}$ alkyl groups, examples thereof include a 5-(trifluoromethyl)-1,3,4-oxadiazol-2-yl group, a 5-(2,2,2-trifluoroethyl)-1,3,4-oxadiazol-2-yl group, a 5-(2-fluoroethyl)-1,3,4-oxadiazol-2-yl group, and a 4-(trifluoromethyl)-1,2,3-oxadiazol-5-yl group, and it is preferably an oxadiazolyl group substituted with one $C_{1-3}$ alkyl group which is substituted with 1 to 3 halogen atoms, more preferably an oxadiazolyl group substituted with one $C_{1-3}$ alkyl group which is substituted with 1 to 3 fluorine atoms.

As described herein, "its salt" or "pharmaceutically acceptable salt" may be any salt in a pharmaceutically acceptable form, and examples thereof include mineral acid salts, such as a hydrochloric acid salt, a hydrobromic acid salt, a sulfuric acid salt, a nitric acid salt, and a phosphoric acid salt; and organic acid salts, such as an acetic acid salt, a propionic acid salt, a tartaric acid salt, a fumaric acid salt, a maleic acid salt, a succinic acid salt, a malic acid salt, a citric acid salt, a methanesulfonic acid salt, a p-toluenesulfonic acid salt, and a trifuloroacetic acid salt.

As described herein, a group "may be substituted" with a substituent group means a state in which the group is substituted with the substituent group or the group is not substituted with the substituent group.

The fused pyrimidine compound or its salt of the present invention is characterized in that it has a 5,6,7,8-tetrahydropyrido[3,4-d]pyrimidine skeleton and has a group represented by —$NHR_1$ ($R_1$ is as defined as below) on position 4 and benzene substituted with a specific substituent on position 7 of the skeleton, wherein the benzene has a cyano group or a nitro group on position 4 and a specific substituent Y (Y is as defined as below) on position 3. The fused pyrimidine compound of the present invention or a salt thereof has an antagonist activity for an androgen receptor (AR) and exhibits an anti-tumor effect. Meanwhile, a compound having, instead of the 5,6,7,8-tetrahydropyrido[3,4-d]pyrimidine skeleton, 5,6,7,8-tetrahydropyrido[4,3-d]pyrimidine or 5,6,7,8-tetrahydro[1,2,4]triazolo[4,3-a]pyrazine skeleton does not exhibit either the AR antagonist activity or anti-tumor effect. Incidentally, a compound wherein the benzene having a cyano group or a nitro group on position 4 and a substituent Y on position 3 is replaced by another cyano- or nitro-benzene does not exhibit the aforementioned effects.

In the aforementioned Patent Literatures 1 to 3, a compound having 5,6,7,8-tetrahydropyrido[3,4-d]pyrimidine skeleton is disclosed. However, in none of the Patent Literatures 1 to 3, the compound having a group represented by —NHR$_1$ (R$_1$ is as defined below) on position 4 and cyanobenzene or nitrobenzene on position 7 of the 5,6,7,8-tetrahydropyrido[3,4-d]pyrimidine is disclosed. Furthermore, the usefulness of the 5,6,7,8-tetrahydropyrido[3,4-d] pyrimidine compound as an anti-tumor agent is not disclosed at all in Patent Literatures 1 to 3, and the effect of the compound against AR is not suggested.

The fused pyrimidine compound of the present invention is represented by the following formula (I).

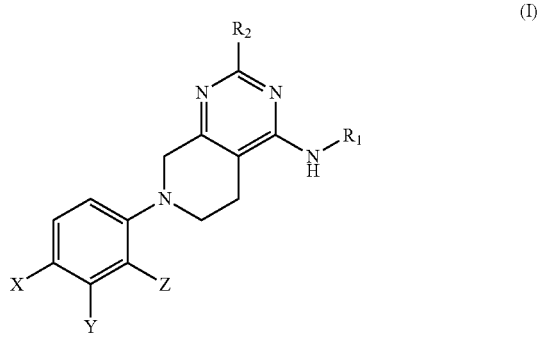

In the formula (I), X represents a cyano group or a nitro group.

In the formula (I), Y represents a halogen atom, a halogeno-C$_{1-3}$ alkyl group, a C$_{1-3}$ alkoxy group, or a C$_{1-3}$ alkyl group. Examples of the "halogen atom" represented by Y include the aforementioned halogen atom, and it is preferably a chlorine atom or a bromine atom. Examples of the "halogeno-C$_{1-3}$ alkyl group" represented by Y include the aforementioned halogeno-C$_{1-3}$ alkyl group, and it is preferably a trifluoromethyl group. The "C$_{1-3}$ alkoxy group" represented by Y is, for example, the aforementioned C$_{1-3}$ alkoxy group, and is preferably a methoxy group or an isopropoxy group. The "C$_{1-3}$ alkyl group" represented by Y is, for example, the aforementioned C$_{1-3}$ alkyl group, and is preferably a methyl group. In the formula (I), Y is preferably a chlorine atom, a bromine atom, a trifluoromethyl group, a methoxy group, an isopropoxy group, or a methyl group.

In the formula (I), Z represents a hydrogen atom, a halogen atom, or a C$_{1-3}$ alkyl group. The "halogen atom" represented by Z is, for example, the aforementioned halogen atom, and is preferably a fluorine atom. The "C$_{1-3}$ alkyl group" represented by Z is, for example, the aforementioned C$_{1-3}$ alkyl group. In the formula (I), Z is preferably a hydrogen atom or a fluorine atom.

In the formula (I), R$_2$ represents a hydrogen atom, a C$_{1-3}$ alkyl group, or a cyano group. The "C$_{1-3}$ alkyl group" represented by R$_2$ is, for example, the aforementioned C$_{1-3}$ alkyl group, and is preferably a methyl group. In the formula (I), R$_2$ is preferably a hydrogen atom, a methyl group, or a cyano group.

In the formula (I), R$_1$ represents a C$_{6-14}$ aryl group which is substituted with Ra and may be substituted simultaneously with Rb, or a 5- or 6-membered heteroaryl group which is substituted with Ra and may be substituted simultaneously with Rb.

The "C$_{6-14}$ aryl group" of "C$_{6-14}$ aryl group which is substituted with Ra and may be substituted simultaneously with Rb" regarding R$_1$ is the aforementioned C$_{6-14}$ aryl group, and it is preferably a phenyl group. The number of Ra substituted on the "C$_{6-14}$ aryl group" is 1, and the number of Rb is 0, 1 or 2.

Regarding R$_1$, the "5- or 6-membered heteroaryl group" of the "5- or 6-membered heteroaryl group which is substituted with Ra and may be substituted simultaneously with Rb" is selected from 5- or 6-membered monocyclic heteroaryl groups among the aforementioned heteroaryl groups. The "5- or 6-membered heteroaryl group" is preferably a 5- or 6-membered monocyclic heteroaryl group having 1 to 3 hetero atoms independently selected from oxygen, nitrogen, and sulfur and is more preferably a pyridinyl group, a pyrazinyl group, a pyrimidinyl group, a pyridazinyl group, a triazinyl group, a thiazolyl group, a thiadiazolyl group, an oxazolyl group, or an oxadiazolyl group, more preferably a pyridinyl group, a pyrimidinyl group, a pyridazinyl group, a thiazolyl group, an oxazolyl group, or a thiadiazolyl group, and even more preferably a pyridinyl group or a pyridazinyl group. The number of Ra substituted on the "5- or 6-membered heteroaryl group" is one, and the number of Rb is 0, 1, or 2.

In the formula (I), R$_1$ is preferably a group selected from the group consisting of the followings:

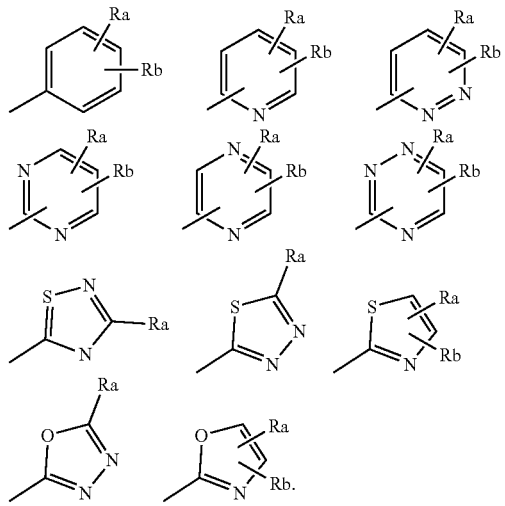

R$_1$ is more preferably a phenyl group, pyridinyl group, or pyridazinyl group substituted with Ra and Rb, selected from the group consisting of the followings:

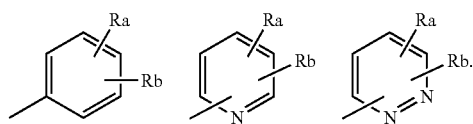

R$_1$ is even more preferably a phenyl group, pyridinyl group, or pyridazinyl group substituted with Ra and Rb, selected from the group consisting of the followings:

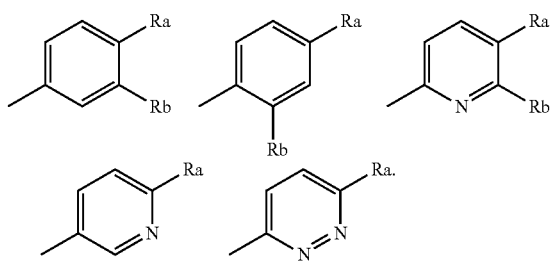

Ra substituted on R₁ in the formula (I) represents a phenyl group, a hydroxy-$C_{1-6}$ alkyl group, a hydroxy-$C_{3-7}$ cycloalkyl group, a hydroxy-heterocycloalkyl group, a $C_{1-6}$ alkoxy group which may be substituted with Rc, an amino-$C_{1-6}$ alkyl group which may be substituted with Rf, a halogeno-$C_{1-3}$ alkoxy group, a $C_{3-7}$ cycloalkylaminosulfonyl group, a $C_{1-3}$ alkylsulfonyl group, a 3- to 7-membered monocyclic heterocycloalkylsulfonyl group, a $C_{1-3}$ alkoxycarbonylamino group which may be substituted with a halogen, a $C_{1-3}$ alkylcarbonylamino group which may be substituted with a halogen, a 3- to 7-membered monocyclic heterocycloalkanecarbonyl group substituted with a hydroxy-$C_{1-6}$ alkyl group, a bicyclic heterocycloalkyl group, or —(CH₂)ₙ—C(=O)—NRdRe.

The "hydroxy-$C_{1-6}$ alkyl group" represented by Ra is the aforementioned hydroxy-$C_{1-6}$ alkyl group, preferably a $C_{1-4}$ alkyl group substituted with 1 to 3 hydroxyl groups, and more preferably an ethyl group substituted with 1 to 3 hydroxyl groups (hydroxy-ethyl group) or an isopropyl group substituted with 1 to 3 hydroxyl groups (hydroxy-isopropyl group). The number of the hydroxyl group is preferably 1. More preferably, the "hydroxy-$C_{1-6}$ alkyl group" is a 2-hydroxypropan-2-yl group.

The "hydroxy-$C_{3-7}$ cycloalkyl group" represented by Ra is the aforementioned hydroxy-$C_{3-7}$ cycloalkyl group.

The "hydroxy-heterocycloalkyl group" represented by Ra is the aforementioned hydroxy-heterocycloalkyl group and is preferably a heterocycloalkyl group substituted with 1 to 3 hydroxyl groups. The "hydroxy-heterocycloalkyl group" is more preferably a monocyclic heterocycloalkyl group substituted with 1 to 3 hydroxyl groups and even more preferably an oxetanyl group substituted with 1 to 3 hydroxyl groups (hydroxy-oxetanyl group) and even more preferably a 3-hydroxyoxetan-3-yl group.

The "$C_{1-6}$ alkoxy group which may be substituted with Rc" represented by Ra is the aforementioned $C_{1-6}$ alkoxy group which is substituted with 0 to 3 Rcs, and it is preferably the aforementioned $C_{1-4}$ alkoxy group which is substituted with 0 to 3 Res. The number of Rc is preferably 0 or 1.

Rc represents a pyrazolyl group, triazolyl group, or tetrazolyl group which may be substituted or a piperazinyl group which may be substituted with Rf.

The "pyrazolyl group, triazolyl group, or tetrazolyl group which may be substituted" represented by Rc is preferably a pyrazolyl group, triazolyl group, or tetrazolyl group substituted with a $C_{1-3}$ alkyl group or a halogeno-$C_{1-3}$ alkyl group or an unsubstituted pyrazolyl group, triazolyl group, or tetrazolyl group.

The "piperazinyl group which may be substituted with Rf" represented by Rc is a piperazinyl group unsubstituted or substituted with one Rf. Rf in the "piperazinyl group which may be substituted with Rf" represented by Rc represents $C_{1-6}$ alkyl, $C_{1-6}$ alkylcarbonyl, $C_{1-6}$ alkylsulfonyl, $C_{1-6}$ alkoxycarbonyl, or $C_{1-6}$ alkylaminocarbonyl. The "$C_{1-6}$ alkyl" represents the aforementioned $C_{1-6}$ alkyl and is preferably a methyl group. The "$C_{1-6}$ alkylcarbonyl" represents the aforementioned $C_{1-6}$ alkylcarbonyl and is preferably methylcarbonyl (acetyl). The "$C_{1-6}$ alkylsulfonyl" represents the aforementioned $C_{1-6}$ alkylsulfonyl and is preferably methylsulfonyl (mesyl). The "$C_{1-6}$ alkoxycarbonyl" represents the aforementioned $C_{1-6}$ alkoxycarbonyl and is preferably tert-butoxycarbonyl. The "$C_{1-6}$ alkylaminocarbonyl" represents the aforementioned $C_{1-6}$ alkylaminocarbonyl. The number of Rf is 0 or 1.

The "$C_{1-6}$ alkoxy group which may be substituted with Rc" is preferably a $C_{1-6}$ alkoxy group or a $C_{1-6}$ alkoxy group substituted with a piperazinyl group which may be substituted with Rf and more preferably a $C_{1-6}$ alkoxy group, a $C_{1-6}$ alkoxy group substituted with an unsubstituted piperazinyl group, or a $C_{1-6}$ alkoxy group substituted with a piperazinyl group which is substituted with acetyl, mesyl, tert-butoxycarbonyl, or methyl, more preferably a methoxy group, an n-propoxy group substituted with an unsubstituted piperazinyl group, or an n-propoxy group substituted with a piperazinyl group which is substituted with acetyl, mesyl, tert-butoxycarbonyl, or methyl.

The "amino-$C_{1-6}$ alkyl group which may be substituted with Rf" represented by Ra is the aforementioned amino-$C_{1-6}$ alkyl group substituted with 0 to 3 Rfs, and is preferably an amino-$C_{1-6}$ alkyl group unsubstituted or N-substituted with one Rf. The amino-$C_{1-6}$ alkyl group is preferably an amino-$C_{1-3}$ alkyl group. Rf in the "amino-$C_{1-6}$ alkyl group which may be substituted with Rf" is the same as Rf in the aforementioned "piperazinyl group which may be substituted with Rf", and is preferably a $C_{1-6}$ alkoxycarbonyl. The "amino-$C_{1-6}$ alkyl group which may be substituted with Rf" is preferably an amino-$C_{1-6}$ alkyl group unsubstituted or substituted with $C_{1-6}$ alkoxycarbonyl.

The "halogeno-$C_{1-3}$ alkoxy group" represented by Ra is the aforementioned halogeno-$C_{1-3}$ alkoxy group and is preferably a trifluoromethoxy group.

The "$C_{3-7}$ cycloalkylaminosulfonyl group" represented by Ra is the aforementioned $C_{3-7}$ cycloalkylaminosulfonyl group.

The "$C_{1-3}$ alkylsulfonyl group" represented by Ra is the aforementioned $C_{1-3}$ alkylsulfonyl group.

The "3- to 7-membered monocyclic heterocycloalkylsulfonyl group" represented by Ra is a sulfonyl group substituted with the aforementioned 3- to 7-membered monocyclic heterocycloalkyl group.

The "$C_{1-3}$ alkoxycarbonylamino group which may be substituted with a halogen" represented by Ra is the aforementioned $C_{1-3}$ alkoxycarbonylamino group substituted with 0 to 7 halogen atoms and is preferably the aforementioned halogeno-$C_{1-3}$ alkoxycarbonylamino group.

The "$C_{1-3}$ alkylcarbonylamino group which may be substituted with a halogen" represented by Ra is the aforementioned $C_{1-3}$ alkylcarbonylamino group substituted with 0 to 7 halogen atoms and is preferably the aforementioned halogeno-$C_{1-3}$ alkylcarbonylamino group.

The "3- to 7-membered monocyclic heterocycloalkanecarbonyl group substituted with a hydroxy-$C_{1-6}$ alkyl group" represented by Ra is a carbonyl group substituted with the aforementioned 3- to 7-membered monocyclic heterocycloalkyl group which is substituted with one of the aforementioned hydroxy-$C_{1-6}$ alkyl groups.

The "bicyclic heterocycloalkyl group" represented by Ra indicates a bicyclic group among the aforementioned heterocycloalkyl groups and is preferably a 2-oxa-6-azaspiro [3.3]heptyl group.

In the group represented by "—(CH$_2$)$_n$—C(=O)—NRdRe" regarding Ra, Rd and Re each independently represent a hydrogen atom, a C$_{1-3}$ alkyl group, a C$_{2-6}$ alkynyl group, a C$_{1-6}$ alkoxy group, a C$_{3-7}$ cycloalkyl group, a halogeno-C$_{1-3}$ alkyl group, a hydroxy-C$_{1-6}$ alkyl group, a hydroxy-C$_{3-7}$ cycloalkyl group, a hydroxy-C$_{3-7}$ cycloalkyl-C$_{1-6}$ alkyl group, a C$_{1-4}$ alkoxy group, or a C$_{1-6}$ alkyl group substituted with Rg. Alternatively, NRdRe may form a ring.

In the group represented by "—(CH$_2$)$_n$—C(=O)—NRdRe" regarding Ra, n can be an integer of from 0 to 3 and is preferably 0 or 1, more preferably 0.

The "C$_{1-3}$ alkyl group" represented by Rd or Re is the aforementioned C$_{1-3}$ alkyl group and is preferably a methyl group or an ethyl group.

The "C$_{2-6}$ alkynyl group" represented by Rd or Re is the aforementioned C$_{2-6}$ alkynyl group and is preferably a propynyl group.

The "C$_{1-6}$ alkoxy group" represented by Rd or Re is the aforementioned C$_{1-4}$ alkoxy group and is preferably a tert-butoxy group.

The "C$_{3-7}$ cycloalkyl group" represented by Rd or Re is the aforementioned "C$_{3-7}$ cycloalkyl group" and is preferably a cyclopropyl group.

The "halogeno-C$_{1-3}$ alkyl group" represented by Rd or Re is the aforementioned halogeno-C$_{1-3}$ alkyl group and is preferably a trifluoroethyl group, more preferably a 2,2,2-trifluoroethyl group.

The "hydroxy-C$_{1-6}$ alkyl group" represented by Rd or Re is the aforementioned hydroxy-C$_{1-6}$ alkyl group.

The "hydroxy-C$_{3-7}$ cycloalkyl group" represented by Rd or Re is the aforementioned hydroxy-C$_{3-7}$ cycloalkyl group.

The "hydroxy-C$_{3-7}$ cycloalkyl-C$_{1-6}$ alkyl group" represented by Rd or Re is the aforementioned hydroxy-C$_{3-7}$ cycloalkyl-C$_{1-6}$ alkyl group.

The "C$_{1-6}$ alkyl group substituted with Rg" represented by Rd or Re is the aforementioned C$_{1-6}$ alkyl group substituted with 1 to 3 Rgs and is preferably the aforementioned C$_{1-4}$ alkyl group substituted with one Rg.

Rg represents a C$_{1-6}$ alkylpyrazolyl group, a halogeno-C$_{1-3}$ alkylthiazolyl group, an oxadiazolyl group, a halogeno-C$_{1-3}$ alkyloxadiazolyl group, or a C$_{1-6}$ alkoxycarbonylamino group. The "C$_{1-6}$ alkylpyrazolyl group" represented by Rg is the aforementioned C$_{1-6}$ alkylpyrazolyl group. The "halogeno-C$_{1-3}$ alkylthiazolyl group" represented by Rg is the aforementioned halogeno-C$_{1-3}$ alkylthiazolyl group. The "halogeno-C$_{1-3}$ alkyloxadiazolyl group" represented by Rg is the aforementioned halogeno-C$_{1-3}$ alkyloxadiazolyl group. The "C$_{1-6}$ alkoxycarbonylamino group" represented by Rg is the aforementioned C$_{1-6}$ alkoxycarbonylamino group and is preferably a tert-butoxycarbonylamino group.

The "C$_{1-6}$ alkyl group substituted with Rg" is preferably a C$_{1-6}$ alkyl group substituted with a tert-butoxycarbonylamino group and more preferably an ethyl group substituted with a tert-butoxycarbonylamino group.

Alternatively, NRdRe may form a ring. If NRdRe forms a ring, then a 3- to 7-membered nitrogen-containing heterocyclic ring is formed. The 3- to 7-membered nitrogen-containing heterocyclic ring includes aziridine, azetidine, pyrrolidine, piperidine, or azepane, and is preferably azepane.

In Rd and Re represented in "—(CH$_2$)$_n$—C(=O)—NRdRe" regarding Ra, preferably, either one of Rd and Re is a C$_{1-3}$ alkyl group, a C$_{2-6}$ alkynyl group, a C$_1$-3 alkoxy group, a C$_{3-7}$ cycloalkyl group, a halogeno-C$_{1-3}$ alkyl group, or a C$_{1-6}$ alkyl group substituted with Rg, and the other is a hydrogen atom or a C$_{1-3}$ alkyl group; or NRdRe is a 3- to 7-membered nitrogen-containing heterocyclic ring containing one nitrogen atom. More preferably, either one of Rd and Re is a methyl group, an ethyl group, a propynyl group, a tert-butoxy group, a trifluoroethyl group, or an ethyl group substituted with tert-butoxycarbonylamino, and the other is a hydrogen atom or a methyl group; or NRdRe is azepane.

Preferably, in the formula (I):
Ra represents a phenyl group, a hydroxy-C$_{1-3}$ alkyl group, a hydroxy-heterocycloalkyl group, a C$_{1-6}$ alkoxy group which may be substituted with Rc, an amino-C$_{1-6}$ alkyl group which may be substituted with Rf, a halogeno-C$_{1-3}$ alkoxy group, a bicyclic heterocycloalkyl group, or —(CH$_2$)$_n$—C(=O)—NRdRe.

More preferably, in the formula (I):
Ra represents a phenyl group, a hydroxy-ethyl group, a hydroxy-isopropyl group, a hydroxy-oxetanyl group, a methoxy group, a trifluoromethoxy group, a 2-oxa-6-azaspiro[3.3]heptyl group, —(CH$_2$)$_n$—C(=O)—NRdRe, or an n-propoxy group substituted with a piperazinyl group which may be substituted with acetyl, tert-butoxycarbonyl, mesyl, or methyl.

In the formula (I), Rb represents a hydrogen atom, a halogen atom, a C$_{1-3}$ alkyl group which may be substituted with a halogen atom, or a C$_{1-4}$ alkoxy group which may be substituted with a halogen atom. The "halogen atom" is, for example, the aforementioned halogen atom, and is preferably a fluorine atom or a chlorine atom. The "C$_{1-3}$ alkyl group which may be substituted with a halogen atom" include the aforementioned C$_{1-3}$ alkyl group or a halogeno-C$_{1-3}$ alkyl group, and is preferably a methyl group or a trifluoromethyl group. The "C$_{1-4}$ alkoxy group which may be substituted with a halogen atom" include the aforementioned C$_{1-4}$ alkoxy group or a halogeno-C$_{1-4}$ alkoxy group, and is preferably a trifluoromethoxy group or methoxy group. Rb is preferably a hydrogen atom, a fluorine atom, a chlorine atom, a methyl group, a trifluoromethyl group, a trifluoromethoxy group, or a methoxy group.

Regarding R$_1$ in the formula (I), Ra and Rb substituted on the C$_{6-14}$ aryl group or the 5- or 6-membered heteroaryl group may be bonded to each other to form a fused ring together with the C$_{6-14}$ aryl or heteroaryl group. If the fused ring is formed, then preferably, Ra is an amino-C$_{1-6}$ alkyl group which may be substituted with Rf, and Rb is a C$_{1-3}$ alkyl group; and more preferably, Ra is a methyl group or ethyl group which may be substituted with Rf, and Rb is a methyl group. In addition, the ring to which the Ra and Rb are bonded is preferably C$_{6-14}$ aryl. Examples of the thus-formed fused ring group represented by R$_1$ include a substituted or unsubstituted tetrahydroisoquinolinyl group and a substituted or unsubstituted isoindolinyl group.

In a preferred embodiment, R$_1$ in the formula (I) is selected from the group consisting of the followings:

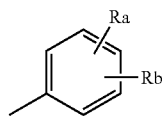

(in the formula,
Ra represents a phenyl group, a C$_{1-6}$ alkoxy group which may be substituted with Rc, an amino-C$_{1-6}$ alkyl group which may be substituted with Rf, a halogeno-C$_{1-3}$ alkoxy group, or a bicyclic heterocycloalkyl group; and
Rb represents a hydrogen atom, a halogen atom, a C$_{1-3}$ alkyl group which may be substituted with a halogen atom, or a $C_{1-4}$ alkoxy group which may be substituted with a halogen atom, or Ra is an amino-$C_{1-6}$ alkyl group which may be substituted with Rf, Rb is a $C_{1-3}$ alkyl group, and the Ra and Rb are bonded to each other to form a fused ring together with the ring on which they are substituted);

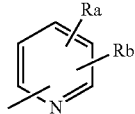

(in the formula,
Ra represents a hydroxy-$C_{1-6}$ alkyl group, a hydroxy-heterocycloalkyl group, or —(CH$_2$)$_n$—C(=O)—NRdRe; and
Rb represents a hydrogen atom or a halogen atom); and

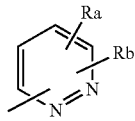

(in the formula,
Ra represents —(CH$_2$)$_n$—C(=O)—NRdRe; and
Rb represents a hydrogen atom).

In more preferred embodiment, $R_1$ in the formula (I) is selected from the group consisting of the followings:

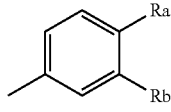

(in the formula,
Ra represents a methoxy group, a trifluoromethoxy group, an n-propoxy group substituted with an unsubstituted piperazinyl group, an n-propoxy group substituted with a piperazinyl group which is substituted with acetyl, mesyl, or methyl, or a 2-oxa-6-azaspiro[3.3]heptyl group; and Rb represents a hydrogen atom, a fluorine atom, a chlorine atom, a methyl group which may be substituted with a fluorine atom, or a methoxy group, or Ra is an amino-ethyl group which may be substituted with a tert-butoxycarbonyl group, Rb is a methyl group, and the Ra and Rb are bonded to each other to form a substituted or unsubstituted isoquinoline ring or isoindoline ring together with the benzene ring);

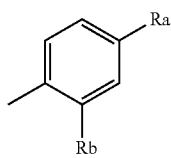

(in the formula,
Ra represents an n-propoxy group substituted with a piperazinyl group which is substituted with an acetyl group, and Rb represents a methyl group which may be substituted with a fluorine atom);

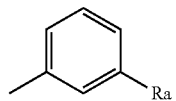

(in the formula,
Ra represents a phenyl group);

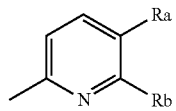

(in the formula,
Ra represents a hydroxy-isopropyl group, a hydroxy-oxetanyl group, or —(CH$_2$)$_n$—C(=O)—NRdRe;
Rb represents a hydrogen atom or a fluorine atom; and
Rd represents a methyl group, an ethyl group, a propynyl group, or a tert-butoxy group, and Re represents a hydrogen atom; or NRdRe forms azepane);

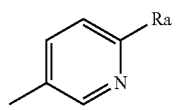

(in the formula,
Ra represents a methoxy group); and

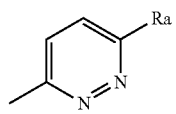

(in the formula,
Ra represents —(CH$_2$)$_n$—C(=O)—NRdRe; and
Rd represents an ethyl group, a cyclopropyl group, a propynyl group, a trifluoroethyl group, or an ethyl group substituted with a tert-butoxycarbonylamino group, and Re represents a hydrogen atom).

In another embodiment, in the formula (I),
x is a cyano group, Y is a halogen atom or a halogeno-$C_{1-3}$ alkyl group, $R_2$ is a hydrogen atom, and Z is a hydrogen atom;
$R_1$ is a $C_{6-14}$ aryl group which is substituted with Ra and may be substituted simultaneously with Rb or a 5- or 6-membered heteroaryl group which is substituted with Ra and may be substituted simultaneously with Rb; and
if Rb is a hydrogen atom, a halogen atom, or a $C_{1-3}$ alkyl group which may be substituted with a halogen atom, then Ra is selected from the following (a) to (g), preferably from the following (a), (b), (d), (f), and (g):
(a) a hydroxy-heterocycloalkyl group,
preferably a heterocycloalkyl group substituted with 1 to 3 hydroxyl groups,
more preferably an oxetanyl group substituted with 1 to 3 hydroxyl groups, and
even more preferably a 3-hydroxyoxetan-3-yl group;

(b) a $C_{1-6}$ alkoxy group which may be substituted with Rc (wherein, Rc represents a piperazinyl group which may be substituted with $C_{1-5}$ alkyl, $C_{1-6}$ alkylcarbonyl, $C_{1-6}$ alkoxycarbonyl, or $C_{1-6}$ alkylaminocarbonyl),
preferably a $C_{1-6}$ alkoxy group or a $C_{1-6}$ alkoxy group substituted with a piperazinyl group which may be substituted with acetyl, and
more preferably a methoxy group or an n-propoxy group substituted with a piperazinyl group which may be substituted with an acetyl group;
(c) an amino-$C_{1-6}$ alkyl group which may be substituted with Rf,
preferably the group and Rb are bonded to each other to form a fused ring together with the $C_{6-14}$ aryl or the heteroaryl group;
(d) a halogeno-$C_{1-3}$ alkoxy group, preferably a trifluoromethoxy group;
(e) a $C_{1-3}$ alkylsulfonyl group;
(f) a bicyclic cycloheteroalkyl group, preferably a 2-oxa-6-azaspiro[3.3]heptyl group; and
(g) —(CH$_2$)$_n$—C(=O)—NRdRe
(wherein, n is an integer of from 0 to 3, preferably 0;
Rd and Re are as described above,
preferably Rd and Re are each independently a hydrogen atom, a $C_{1-6}$ alkyl group, a $C_{2-6}$ alkynyl group, a $C_{1-6}$ alkoxy group, a $C_{3-6}$ cycloalkyl group, a halogeno-$C_{1-3}$ alkyl group, or a $C_{1-6}$ alkyl substituted with Rg, or NRdRe forms a ring,
more preferably either one of Rd and Re is a $C_{1-3}$ alkyl group, a $C_{2-6}$ alkynyl group, a $C_{1-3}$ alkoxy, a $C_{3-7}$ cycloalkyl group, or a $C_{1-6}$ alkyl group substituted with Rg, and the other is a hydrogen atom or a $C_{1-3}$ alkyl group, and Rg is as described above; or Rd and Re form a 3- to 7-membered nitrogen-containing heterocyclic ring containing one nitrogen atom,
even more preferably either one of Rd and Re is a methyl group, an ethyl group, a propynyl group, a tert-butoxy group, or an ethyl group substituted with a tert-butoxycarbonylamino group, and the other is a hydrogen atom or a methyl group; or NRdRe is azepane,
provided that if either one of Rd and Re is a halogeno-$C_{1-3}$ alkyl group, a hydroxy-$C_{1-G}$ alkyl group, a hydroxy-$C_{3-7}$ cycloalkyl group, a hydroxy-$C_{3-7}$ cycloalkyl-$C_{1-6}$ alkyl group, or a $C_{1-6}$ alkyl group substituted with $C_1$ alkylpyrazolyl, halogeno-$C_{1-3}$ alkylthiazolyl, oxadiazolyl, or halogeno-$C_{1-3}$ alkyloxadiazolyl, then the other is not a hydrogen atom).
In another preferred embodiment, in the formula (I),
X is a cyano group, Y is a halogen atom or a halogeno-$C_{1-3}$ alkyl group, $R_2$ is a hydrogen atom, and Z is a hydrogen atom; and
if Rb is a hydrogen atom, a halogen atom, or a $C_{1-3}$ alkyl group which may be substituted with a halogen atom, then $R_1$ is selected from the group consisting of the followings:

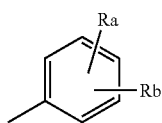

(in the formula,
Ra represents an amino-$C_{1-6}$ alkyl group which may be substituted with Rf, a halogeno-$C_{1-3}$ alkoxy group, a bicyclic heterocycloalkyl group, or a $C_{1-6}$ alkoxy group which may be substituted with Rc (wherein, Rc represents a piperazinyl group which may be substituted with $C_{1-6}$ alkyl, $C_{1-6}$ alkylcarbonyl, $C_{1-6}$ alkoxycarbonyl group, or $C_{1-6}$ alkylaminocarbonyl), and Rb represents a hydrogen atom, a halogen atom, a $C_{1-3}$ alkyl group which may be substituted with a halogen atom, or a $C_{1-4}$ alkoxy group which may be substituted with a halogen atom; or
Ra is an amino-$C_{1-6}$ alkyl group which may be substituted with Rf, Rb is a $C_{1-3}$ alkyl group, and the Ra and Rb are bonded to each other to form a fused ring together with the ring on which they are substituted);

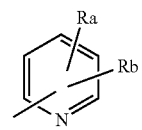

(in the formula, Ra represents a hydroxy-heterocycloalkyl group or —(CH$_2$)$_n$—C(=O)—NRdRe (wherein, the —(CH$_2$)$_n$—C(=O)—NRdRe is as shown in the (g) above);
Rb represents a hydrogen atom or a halogen atom); and

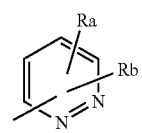

(in the formula,
Ra represents —(CH$_2$)$_n$—C(=O)—NRdRe (wherein, the —(CH$_2$)$_n$—C(=O)—NRdRe is as shown in the (g) above);
Rb represents a hydrogen atom).
In more preferred embodiment, in the formula (I),
X is a cyano group, Y is a halogen atom or a halogeno-$C_{1-3}$ alkyl group, $R_2$ is a hydrogen atom, and Z is a hydrogen atom, and
if Rb is a hydrogen atom, a halogen atom, or a $C_{1-3}$ alkyl group which may be substituted with a halogen atom, then $R_1$ is selected from the group consisting of the followings:

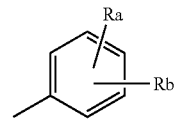

(in the formula,
Ra represents a methoxy group, an n-propoxy group substituted with a piperazinyl group which may be substituted with an acetyl group, a trifluoromethoxy group, or a 2-oxa-6-azaspiro[3.3]heptyl group, and Rb represents a hydrogen atom, a fluorine atom, a chlorine atom, or a methyl group which may be substituted with a fluorine atom,
or
Ra is an amino-ethyl group which may be substituted with a tert-butoxycarbonyl group, Rb is a methyl group, and the Ra and Rb are bonded to each other to form a fused ring with the benzene ring);

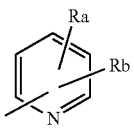

(in the formula,
Ra is a hydroxy-oxetanyl group or —(CH$_2$)$_n$—C(=O)—NRdRe (wherein, the —(CH$_2$)$_n$—C(=O)—NRdRe is as shown in the (g) above);
Rb represents a hydrogen atom or a fluorine atom); and

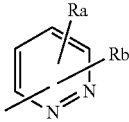

(in the formula,
Ra represents —(CH$_2$)$_n$—C(=O)—NRdRe (wherein, the —(CH$_2$)$_n$—C(=O)—NRdRe is as shown in the (g) above); and
Rb represents a hydrogen atom).

Accordingly, in a preferred embodiment, the fused pyrimidine compound of the present invention is represented by the following formula (I):

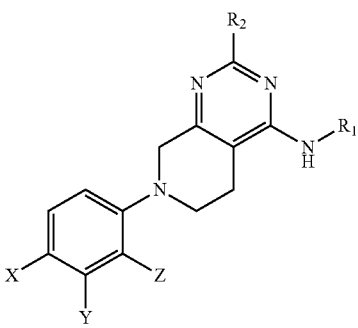

(I)

[in the formula,
X represents a cyano group or a nitro group;
Y represents a halogen atom, a halogeno-C$_{1-3}$ alkyl group, a C$_{1-3}$ alkoxy group, or a C$_{1-3}$ alkyl group;
Z represents a hydrogen atom, a halogen atom, or a C$_{1-3}$ alkyl group;
R$_1$ represents a C$_{6-14}$ aryl group which is substituted with Ra and may be substituted simultaneously with Rb or a 5- or 6-membered heteroaryl group which is substituted with Ra and may be substituted simultaneously with Rb, wherein the Ra and Rb may be bonded to each other to form a fused ring together with the C$_{6-14}$ aryl or heteroaryl group; and
R$_2$ represents a hydrogen atom, a C$_{1-3}$ alkyl group, or a cyano group, wherein
Ra represents a phenyl group, a hydroxy-C$_{1-6}$ alkyl group, a hydroxy-C$_{3-7}$ cycloalkyl group, a hydroxy-heterocycloalkyl group, a C$_{1-6}$ alkoxy group which may be substituted with Rc, an amino-C$_{1-6}$ alkyl group which may be substituted with Rf, a halogeno-C$_{1-3}$ alkoxy group, a C$_{3-7}$ cycloalkylaminosulfonyl group, a C$_{1-3}$ alkylsulfonyl group, a 3- to 7-membered monocyclic heterocycloalkylsulfonyl group, a C$_{1-3}$ alkoxycarbonylamino group which may be substituted with a halogen, a C$_{1-3}$ alkylcarbonylamino group which may be substituted with a halogen, a 3- to 7-membered monocyclic heterocycloalkanecarbonyl group substituted with a hydroxy-C$_{1-6}$ alkyl group, a bicyclic heterocycloalkyl group, or —(CH$_2$)$_n$—C(=O)—NRdRe;
Rb represents a hydrogen atom, a halogen atom, a C$_{1-3}$ alkyl group which may be substituted with a halogen atom, or a C$_{1-4}$ alkoxy group which may be substituted with a halogen atom;
Rc represents a pyrazolyl group, triazolyl group, or tetrazolyl group which each may be substituted or a piperazinyl group which may be substituted with Rf;
Rd and Re each independently represent a hydrogen atom, a C$_{1-3}$ alkyl group, a C$_{2-6}$ alkynyl group, a C$_{1-6}$ alkoxy group, a C$_{3-7}$ cycloalkyl group, a halogeno-C$_{1-3}$ alkyl group, a hydroxy-C$_{1-6}$ alkyl group, a hydroxy-C$_{3-7}$ cycloalkyl group, a hydroxy-C$_{3-7}$ cycloalkyl-C$_{1-6}$ alkyl group, a C$_{1-4}$ alkoxy group, or a C$_{1-6}$ alkyl group substituted with Rg, or NRdRe may form a ring;
Rf represents C$_{1-6}$ alkyl, C$_{1-6}$ alkylcarbonyl, C$_{1-6}$ alkylsulfonyl, a C$_{1-6}$ alkoxycarbonyl group, or C$_{1-6}$ alkylaminocarbonyl;
Rg represents a C$_{1-6}$ alkylpyrazolyl group, a halogeno-C$_{1-3}$ alkylthiazolyl group, an oxadiazolyl group, a halogeno-C$_{1-3}$ alkyloxadiazolyl group, or a C$_{3-6}$ alkoxycarbonylamino group; and
n represents an integer of from 0 to 3 (provided that if X is a cyano group, Y is a halogen atom or a halogeno-C$_{1-3}$ alkyl group, R$_2$ is a hydrogen atom, Z is a hydrogen atom,
R$_1$ is a C$_{6-14}$ aryl group which is substituted with Ra and may be substituted simultaneously with Rb or a 5- or 6-membered heteroaryl group which is substituted with Ra and may be substituted simultaneously with Rb, and
Rb is a hydrogen atom, a halogen atom, or a C$_{1-3}$ alkyl group which may be substituted with a halogen atom;
then Ra is
a hydroxy-heterocycloalkyl group,
a C$_{1-6}$ alkoxy group which may be substituted with Rc (wherein, Rc represents a piperazinyl group which may be substituted with C$_{1-6}$ alkyl, C$_{1-6}$ alkylcarbonyl, C$_{1-6}$, alkoxycarbonyl, or C$_{1-6}$ alkylaminocarbonyl),
an amino-C$_{1-6}$ alkyl group which may be substituted with Rf (wherein, Rf is as described above),
a halogeno-C$_{1-3}$ alkoxy group,
a C$_{1-3}$ alkylsulfonyl group,
a bicyclic cycloheteroalkyl group, or
—(CH$_2$)$_n$—C(=O)—NRdRe (wherein, n, Rd, and Re are as described above, provided that if either one of Rd and Re is a halogeno-C$_{1-3}$ alkyl group, a hydroxy-C$_{1-6}$ alkyl group, a hydroxy-C$_{3-7}$ cycloalkyl group, a hydroxy-C$_{3-7}$ cycloalkyl-C$_{1-6}$ alkyl group, or a C$_{1-6}$ alkyl group substituted with C$_{1-6}$ alkylpyrazolyl, halogeno-C$_{1-3}$ alkylthiazolyl, oxadiazolyl, or halogeno-C$_{1-3}$ alkyloxadiazolyl, then the other is not a hydrogen atom))].

In a more preferred embodiment of the fused pyrimidine compound of the present invention, in the formula (I),
X represents a cyano group or a nitro group;
Y represents a halogen atom, a halogeno-C$_{1-3}$ alkyl group, a C$_{1-3}$ alkoxy group, or a C$_{1-3}$ alkyl group;
Z represents a hydrogen atom or a halogen atom;
R$_1$ is a substituent selected from the group consisting of the followings:

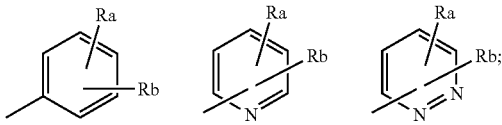 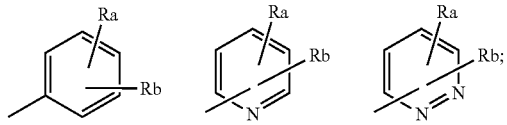

R₂ represents a hydrogen atom, a $C_{1-3}$ alkyl group, or a cyano group;

Ra represents a phenyl group, a hydroxy-$C_{1-6}$ alkyl group, a hydroxy-heterocycloalkyl group, a $C_{1-6}$ alkoxy group which may be substituted with Rc, an amino-$C_{1-6}$ alkyl group which may be substituted with Rf, a halogeno-$C_{1-3}$ alkoxy group, a bicyclic heterocycloalkyl group, or —$(CH_2)_n$—C(=O)—NRdRe;

Rb represents a hydrogen atom, a halogen atom, a $C_{1-3}$ alkyl group which may be substituted with a halogen atom, or a $C_{1-4}$ alkoxy group which may be substituted with a halogen atom;

or Ra and Rb are bonded to each other to form a fused ring together with the ring on which they are substituted;

Rc represents a piperazinyl group which may be substituted with Rf;

Rd and Re each independently represent a hydrogen atom, a $C_1$-3 alkyl group, a $C_{2-6}$ alkynyl group, a $C_{1-6}$ alkoxy group, a $C_{3-7}$ cycloalkyl group, a halogeno-$C_{1-3}$ alkyl group, or a $C_{1-6}$ alkyl group substituted with Rg;

or NRdRe forms a 3- to 7-membered nitrogen-containing heterocyclic ring;

Rf represents a $C_{1-6}$ alkyl group, a $C_{1-6}$ alkylcarbonyl group, a $C_{1-6}$ alkylsulfonyl group, a $C_{1-6}$ alkoxycarbonyl group, or a $C_{1-6}$ alkylaminocarbonyl group;

Rg represents a $C_{1-6}$ alkoxycarbonylamino group; and n represents an integer of 0 or 1

(provided that if X is a cyano group, Y is a halogen atom or a halogeno-$C_{1-3}$ alkyl group, R₂ is a hydrogen atom, Z is a hydrogen atom, R₁ is as described above in this paragraph, and Rb is a hydrogen atom, a halogen atom, or a $C_{1-3}$ alkyl group which may be substituted with a halogen atom;

then Ra is a hydroxy-heterocycloalkyl group, a $C_{1-6}$ alkoxy group which may be substituted with Rc (wherein, Rc represents a piperazinyl group which may be substituted with $C_{1-6}$ alkyl, $C_1$-6 alkylcarbonyl, $C_{1-6}$ alkoxycarbonyl, or $C_{1-6}$ alkylaminocarbonyl), an amino-$C_{1-6}$ alkyl group which may be substituted with Rf (wherein, Rf is as defined above in this paragraph), a halogeno-$C_{1-3}$ alkoxy group, a bicyclic cycloheteroalkyl group, or —$(CH_2)_n$—C(=O)—NRdRe (wherein, n, Rd, and Re are as defined above in this paragraph, provided that if Rd is a halogeno-$C_{1-3}$ alkyl group, then Re is not a hydrogen atom)).

In even more preferred embodiment of the fused pyrimidine compound of the present invention, in the formula (I), X represents a cyano group or a nitro group, Y represents a chlorine atom, a bromine atom, a trifluoromethyl group, a methoxy group, an isopropoxy group, or a methyl group;

Z represents a hydrogen atom or a fluorine atom;

R₁ is a substituent selected from the group consisting of the followings:

R₂ represents a hydrogen atom, a methyl group, or a cyano group;

Ra represents a phenyl group, a hydroxy-ethyl group, a hydroxy-isopropyl group, a hydroxy-oxetanyl group, a methoxy group, a trifluoromethoxy group, a 2-oxa-6-azaspiro[3.3]heptyl group, —$(CH_2)_n$—C(=O)—NRdRe, or an n-propoxy group substituted with a piperazinyl group which may be substituted with acetyl, tert-butoxycarbonyl, mesyl, or methyl;

Rb represents a hydrogen atom, a fluorine atom, a chlorine atom, a methyl group, a trifluoromethyl group, or a methoxy group;

or Ra and Rb are bonded to each other to form a substituted or unsubstituted tetrahydroisoquinolinyl group or isoindolinyl group together with the ring on which they are substituted;

either one of Rd and Re represents a methyl group, an ethyl group, a propynyl group, a cyclopropyl group, a trifluoroethyl group, a tert-butoxy group, or an ethyl group substituted with a tert-butoxycarbonylamino, and the other represents a hydrogen atom or a methyl group;

or NRdRe forms azepane; and n is 0

(provided that if X is a cyano group, Y is a chlorine atom, a bromine atom, or a trifluoromethyl group, R₂ is a hydrogen atom, Z is a hydrogen atom, R₁ is as described in this paragraph, and Rb is a hydrogen atom, a fluorine atom, or a trifluoromethyl group;

then Ra is a hydroxy-oxetanyl group, a trifluoromethoxy group, a 2-oxa-6-azaspiro[3.3]heptyl group, an n-propoxy group substituted with a piperazinyl group which may be substituted with acetyl, tert-butoxycarbonyl, mesyl, or methyl, or —$(CH_2)_n$—C(=O)—NRdRe (wherein, n, Rd, and Re are as defined above in this paragraph, provided that if either one of Rd and Re is a trifluoroethyl group, then the other is not a hydrogen atom)).

Specific examples of the preferred fused pyrimidine compound in the present invention include the compounds shown in the following (1) to (48):

(1) 6-((7-(3-chloro-4-cyanophenyl)-5,6,7,8-tetrahydropyrido[3,4-d]pyrimidin-4-yl)amino)-N-ethyl-2-fluoronicotinamide (2) 6-((7-(3-chloro-4-cyanophenyl)-5,6,7,8-tetrahydropyrido[3,4-d]pyrimidin-4-yl)amino)-2-fluoro-N-methylnicotinamide (3) 6-((7-(4-cyano-3-(trifluoromethyl)phenyl)-5,6,7,8-tetrahydropyrido[3,4-d]pyrimidin-4-yl)amino)-2-fluoro-N-methylnicotinamide (4) 6-((7-(4-cyano-3-(trifluoromethyl)phenyl)-5,6,7,8-tetrahydropyrido[3,4-d]pyrimidin-4-yl)amino)-N-ethyl-2-fluoronicotinamide (5) 6-((7-(4-cyano-3-(trifluoromethyl)phenyl)-5,6,7,8-tetrahydropyrido[3,4-d]pyrimidin-4-yl)amino)-N-ethylnicotinamide (6) 4-(4-((5-(azepane-1-carbonyl)pyridin-2-yl)amino)-5,6-dihydropyrido[3,4-d]pyrimidin-7(8H)-yl)-2-(trifluoromethyl)benzonitrile (7) N-(tert-butoxy)-6-((7-(4-cyano-3-(trifluoromethyl)phenyl)-5,6,7,8-tetrahydropyrido[3,4-d]pyrimidin-4-yl)amino)nicotinamide (8) tert-butyl (2-(6-((7-(4-cyano-3-(trifluoromethyl)phenyl)-5,6,7,8-tetrahydropyrido[3,4-d]pyrimidin-4-yl)amino)pyridazine-3-carboxamido)ethyl)carbamate (9) 6-((7-(4-cyano-3-(trifluoromethyl)phenyl)-5,6,7,8-tetrahydropyrido[3,4-d]pyrimidin-4-yl)amino)-N-cyclopropylpyridazine-3-carboxamide

(10) 6-((7-(4-cyano-3-(trifluoromethyl)phenyl)-5,6,7,8-tetrahydropyrido[3,4-d]pyrimidin-4-yl)amino)-N-ethylpyridazine-3-carboxamide

(11) 6-((7-(4-cyano-3-(trifluoromethyl)phenyl)-5,6,7,8-tetrahydropyrido[3,4-d]pyrimidin-4-yl)amino)-N-(prop-2-yn-1-yl)pyridazine-3-carboxamide

(12) N-ethyl-2-fluoro-6-((7-(4-nitro-3-(trifluoromethyl)phenyl)-5,6,7,8-tetrahydropyrido[3,4-d]pyrimidin-4-yl)amino)nicotinamide

(13) 2-(6-((7-(3-chloro-4-nitrophenyl)-5,6,7,8-tetrahydropyrido[3,4-d]pyrimidin-4-yl)amino)pyridin-3-yl)propan-2-ol

(14) 2-(6-((7-(4-nitro-3-(trifluoromethyl)phenyl)-5,6,7,8-tetrahydropyrido[3,4-d]pyrimidin-4-yl)amino)pyridin-3-yl)propan-2-ol

(15) 2-(6-((7-(3-methoxy-4-nitrophenyl)-5,6,7,8-tetrahydropyrido[3,4-d]pyrimidin-4-yl)amino)pyridin-3-yl)propan-2-ol.

(16) 2-(6-((7-(3-methyl-4-nitrophenyl)-5,6,7,8-tetrahydropyrido[3,4-d]pyrimidin-4-yl)amino)pyridin-3-yl)propan-2-ol

(17) 2-(6-((7-(3-bromo-4-nitrophenyl)-5,6,7,8-tetrahydropyrido[3,4-d]pyrimidin-4-yl)amino)pyridin-3-yl)propan-2-ol

(18) 2-(6-((7-(3-chloro-2-fluoro-4-nitrophenyl)-5,6,7,8-tetrahydropyrido[3,4-d]pyrimidin-4-yl)amino)pyridin-3-yl)propan-2-ol

(19) 2-(6-((7-(3-isopropoxy-4-nitrophenyl)-5,6,7,8-tetrahydropyrido[3,4-d]pyrimidin-4-yl)amino)pyridin-3-yl)propan-2-ol

(20) 4-(4-((5-(2-hydroxypropan-2-yl)pyridin-2-yl)amino)-5,6-dihydropyrido[3,4-d]pyrimidin-7(8H)-yl)-2-methylbenzonitrile

(21) N-(3-fluoro-4-methoxyphenyl)-7-(4-nitro-3-(trifluoromethyl)phenyl)-5,6,7,8-tetrahydropyrido[3,4-d]pyrimidin-4-amine

(22) 7-(3-chloro-4-nitrophenyl)-N-(3-fluoro-4-methoxyphenyl)-5,6,7,8-tetrahydropyrido[3,4-d]pyrimidin-4-amine

(23) 4-(4-((5-(2-hydroxypropan-2-yl)pyridin-2-yl)amino)-5,6-dihydropyrido[3,4-d]pyrimidin-7(8H)-yl)-2-methoxybenzonitrile

(24) 6-((7-(4-nitro-3-(trifluoromethyl)phenyl)-5,6,7,8-tetrahydropyrido[3,4-d]pyrimidin-4-yl)amino)-N-(2,2,2-trifluoroethyl)pyridazine-3-carboxamide

(25) N-(6-methoxypyridin-3-yl)-7-(4-nitro-3-(trifluoromethyl)phenyl)-5,6,7,8-tetrahydropyrido[3,4-d]pyrimidin-4-amine

(26) 4-(4-((3,4-dimethoxyphenyl)amino)-5,6-dihydropyrido[3,4-d]pyrimidin-7(8H)-yl)-2-(trifluoromethyl)benzonitrile

(27) 4-(4-((4-(trifluoromethoxy)phenyl)amino)-5,6-dihydropyrido[3,4-d]pyrimidin-7(8H)-yl)-2-(trifluoromethyl)benzonitrile

(28) 4-(4-((4-(2-oxa-6-azaspiro[3.3]heptan-6-yl)phenyl)amino)-5,6-dihydropyrido[3,4-d]pyrimidin-7(8H)-yl)-2-chlorobenzonitrile

(29) tert-butyl 5-((7-(3-chloro-4-cyanophenyl)-5,6,7,8-tetrahydropyrido[3,4-d]pyrimidin-4-yl)amino)isoindoline-2-carboxylate

(30) tert-butyl 4-(3-(2-chloro-4-((7-(4-nitro-3-(trifluoromethyl)phenyl)-5,6,7,8-tetrahydropyrido[3,4-d]pyrimidin-4-yl)amino)phenoxy)propyl)piperazine-1-carboxylate

(31) N-(3,4-dimethoxyphenyl)-7-(4-nitro-3-(trifluoromethyl)phenyl)-5,6,7,8-tetrahydropyrido[3,4-d]pyrimidin-4-amine

(32) tert-butyl 7-((7-(4-nitro-3-(trifluoromethyl)phenyl)-5,6,7,8-tetrahydropyrido[3,4-d]pyrimidin-4-yl)amino)-3,4-dihydroisoquinoline-2(1H)-carboxylate

(33) N-(3-methyl-4-(2-oxa-6-azaspiro[3.3]heptan-6-yl)phenyl)-7-(4-nitro-3-(trifluoromethyl)phenyl)-5,6,7,8-tetrahydropyrido[3,4-d]pyrimidin-4-amine

(34) N-([1,1'-biphenyl]-3-yl)-7-(4-nitro-3-(trifluoromethyl)phenyl)-5,6,7,8-tetrahydropyrido[3,4-d]pyrimidin-4-amine

(35) 2-chloro-4-(4-((6-fluoro-5-(3-hydroxyoxetan-3-yl)pyridin-2-yl)amino)-5,6-dihydropyrido[3,4-d]pyrimidin-7(8H)-yl)benzonitrile

(36) tert-butyl 7-((7-(3-chloro-4-cyanophenyl)-5,6,7,8-tetrahydropyrido[3,4-d]pyrimidin-4-yl)amino)-3,4-dihydroisoquinolin-2(1H)-carboxylate

(37) 2-chloro-4-(4-(((1,2,3,4-tetrahydroisoquinolin-7-yl)amino)-5,6-dihydropyrido[3,4-d]pyrimidin-7(8H)-yl)benzonitrile

(38) 2-chloro-4-(4-((4-(3-(piperazin-1-yl)propoxy)-3-(trifluoromethyl)phenyl)amino)-5,6-dihydropyrido[3,4-d]pyrimidin-7(8H)-yl)benzonitrile

(39) 1-(4-(3-(2-chloro-4-((7-(4-nitro-3-(trifluoromethyl)phenyl)-5,6,7,8-tetrahydropyrido[3,4-d]pyrimidin-4-yl)amino)phenoxy)propyl)piperazin-1-yl)ethanone

(40) N-(3-chloro-4-(3-(4-(methylsulfonyl)piperazin-1-yl)propoxy)phenyl)-7-(4-nitro-3-(trifluoromethyl)phenyl)-5,6,7,8-tetrahydropyrido[3,4-d]pyrimidin-4-amine

(41) N-(3-chloro-4-(3-(4-methylpiperazin-1-yl)propoxy)phenyl)-7-(4-nitro-3-(trifluoromethyl)phenyl)-5,6,7,8-tetrahydropyrido[3,4-d]pyrimidin-4-amine

(42) 4-(4-((4-(3-(4-acetylpiperazin-1-yl)propoxy)-3-chlorophenyl)amino)-5,6-dihydropyrido[3,4-d]pyrimidin-7(8H)-yl)-2-chlorobenzonitrile

(43) 4-(4-((4-(3-(4-acetylpiperazin-1-yl)propoxy)-3-(trifluoromethyl)phenyl)amino)-5,6-dihydropyrido[3,4-d]pyrimidin-7(8H)-yl)-2-chlorobenzonitrile

(44) 4-(4-((4-(3-(4-acetylpiperazin-1-yl)propoxy)-2-(trifluoromethyl)phenyl)amino)-5,6-dihydropyrido[3,4-d]pyrimidin-7(8H)-yl)-2-(trifluoromethyl)benzonitrile

(45) 1-(4-(3-(4-((7-(4-nitro-3-(trifluoromethyl)phenyl)-5,6,7,8-tetrahydropyrido[3,4-d]pyrimidin-4-yl)amino)-2-(trifluoromethyl)phenoxy)propyl)piperazin-1-yl)ethanone

(46) 1-(4-(3-(4-((7-(4-nitro-3-(trifluoromethyl)phenyl)-5,6,7,8-tetrahydropyrido[3,4-d]pyrimidin-4-yl)amino)phenoxy)propyl) piperazin-1-yl)ethanone

(47) 7-(4-cyano-3-(trifluoromethyl)phenyl)-4-((4-methoxyphenyl)amino)-5,6,7,8-tetrahydropyrido[3,4-d]pyrimidine-2-carbonitrile

(48) 4-(4-((4-methoxyphenyl)amino)-2-methyl-5,6-dihydropyrido[3,4-d]pyrimidin-7(8H)-yl)-2-(trifluoromethyl)benzonitrile The fused pyrimidine compound of the present invention or a salt thereof can be produced by various methods. The compound represented by the formula (T) can be produced according to a generally known method. For example, the compound represented by the formula (I) can be produced by the following Reaction scheme 1.

Reaction scheme 1

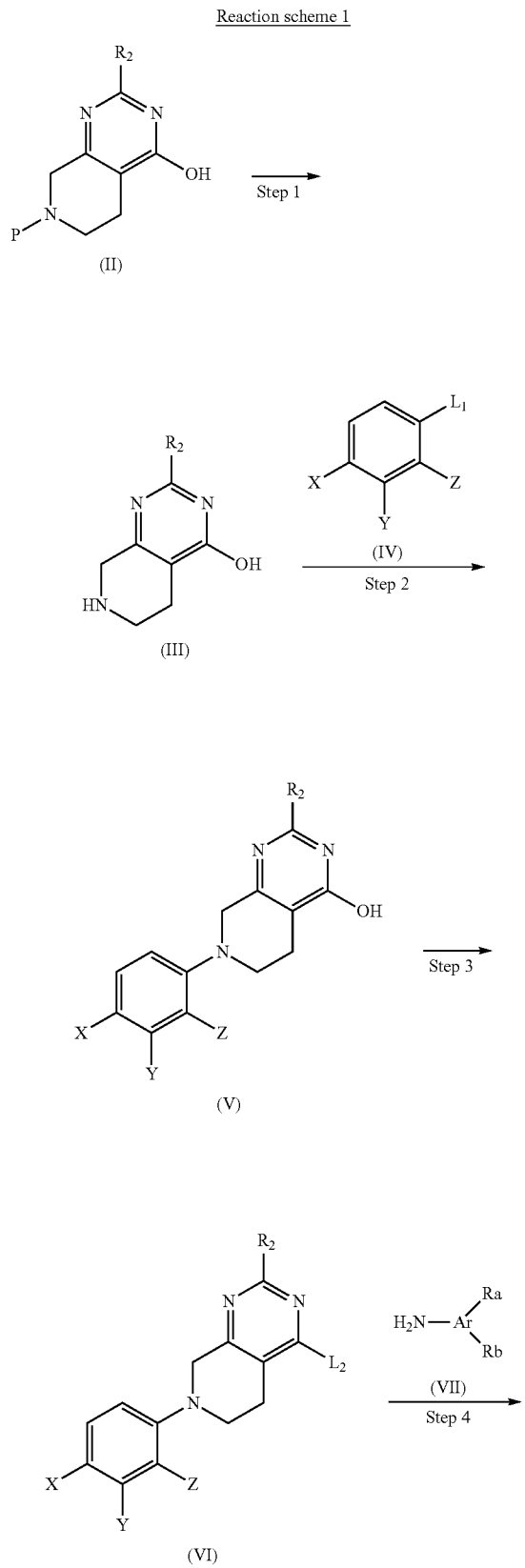

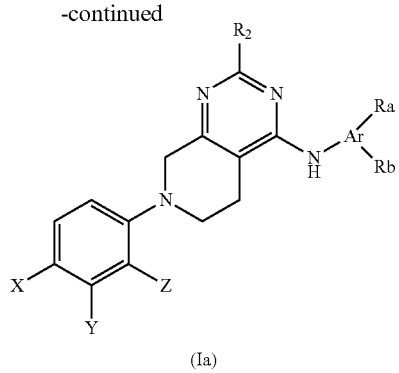

The Reaction scheme 1 is a reaction scheme for synthesizing a compound of the formula (Ia) from a compound of the formula (II). In Reaction scheme 1, X, Y, Z, $R_2$, Ra, and Rb are as defined above and can be each appropriately selected; and Ar represents a $C_{6-14}$ aryl group or a 5 to 6-membered heteroaryl group.

(Step 1)

This step is a reaction for deprotecting the protecting group P of the compound of the formula (II) shown in Reaction scheme 1 above. As for the method for deprotection, it can be performed by a generally known method, for example, the method described in Protective Groups in Organic Synthesis, T. W. Greene, John Wiley & Sons (1981) or a method similar to it. Examples of the protecting group P include a Boc group, a benzyloxycarbonyl group, and a benzyl group. When a benzyl group is used as a protecting group P, examples of the catalyst for hydrogenolysis include palladium hydroxide, palladium/carbon, platinum, Raney nickel, platinum oxide, and rhodium-aluminum oxide. Preferably, it is palladium/carbon. The amount used of the reagent is, relative to 1 eqv. of the compound of the formula (II), 0.001 to 10 eqv., and preferably 0.05 to 2 eqv. Temperature for deprotecting reaction is 0 to 100° C., and preferably 40 to 80° C. The solvent used in this step may be any solvent that does not cause any problem in the reaction, and examples thereof include methanol, THF, ethyl acetate, DMF, pyridine, and a solvent mixture thereof. A preferred solvent is methanol. The compound of the formula (III) obtained by this step can be separated and purified by a known means for separation and purification, for example, concentration, concentration under reduced pressure, crystallization, re-precipitation, and chromatography, or it can be subjected to the next step without any separation and purification.

(Step 2)

In this step, a compound represented by the formula (V) is produced by a nucleophilic substitution reaction between an amine represented by the formula (III) and an aromatic ring having a leaving group $L^1$ represented by the formula (IV). Examples of the leaving group $L_1$ include, in addition to a halogen atom such as fluorine and chlorine, a methanesulfonyloxy group, a p-toluenesulfonyloxy group, and a trifluoromethanesulfonyloxy group. The solvent used for this step is not particularly limited as long as it does not cause any problem on the reaction. Examples of the solvent include toluene, acetonitrile, benzene, dioxane, THF, DMSO, DMF, pyridine, and a mixed solvent thereof. It is preferably DMSO. The equivalent of the aromatic ring represented by the formula (IV), which is used for this reaction, is 0.1 to excess mol and preferably 0.5 to 3 mol relative to 1 mol of the amine represented by the formula (III). In the reaction, a base may or may not be used. When a base is used, examples of the base include pyridine, DBU, potassium carbonate, cesium carbonate, and tertiary amine. The base is preferably triethylamine or potassium carbonate. The temperature for the nucleophilic substitution reaction is 0 to 200° C., and preferably 0 to 50° C. The compound of the formula (V) obtained by this step can be separated and purified by a known means for separation and purification, for example, concentration, concentration under reduced pressure, crystallization, re-precipitation, and chromatography, or it can be subjected to the next step without any separation and purification.

In another method of this step, the compound represented by the formula (V) can be produced using a metal catalyst and a phosphine ligand. As the metal catalyst, a metal complex having various ligands can be used, and examples thereof include tetrakistriphenylphosphine palladium (0), chlorobis(triphenylphosphine)palladium (II), tris (dibenzylideneacetone)dipalladium (0), and palladium acetate (II). Examples of the phosphine ligand include dppf, Xantphos, and XPhos. Examples of the base used for the reaction of this step include potassium carbonate, cesium carbonate, and sodium tert-butoxide. The solvent which can be used for this step is not particularly limited as long as it does not cause any problem on the reaction. Examples of the solvent include dioxane, ethyl acetate, toluene, and pyridine. The amount of the metal catalyst used for the reaction is, relative to 1 mol of the compound of the formula (III), 0.005 to 10 mol, and preferably 0.01 to 1 mol. The time of the reaction is 0.1 to 48 hours, and preferably 0.5 to 24 hours. The reaction temperature is 0 to 200° C., and preferably 50 to 150° C. The compound of the formula (V) obtained by this step can be separated and purified by a known means for separation and purification, for example, concentration, concentration under reduced pressure, crystallization, re-precipitation, and chromatography.

(Step 3)

This step is a step for converting the free hydroxyl group of the compound of the formula (V) to a leaving group $L_2$. Examples of the leaving group $L_2$ include the same groups as $L_1$, and it is preferably a halogen atom. The conversion reaction is carried out without a solvent or in the presence of a solvent. Examples of the solvent which can be used for this step is not particularly limited as long as it does not cause any problem on the reaction. Examples of the solvent include DMF, NMP, DMA, toluene, dichloroethane, and acetonitrile. Examples of the base used for the reaction include triethylamine, diisopropylethylamine, N,N-dimethylaniline, and sodium hydrogen carbonate. The amount of the halogenating agent used for the reaction (e.g., phosphorus oxychloride, phosphorus pentachloride, and phosphorus tribromide) is, relative to 1 mol of the compound of the formula (V), 0.5 to 20 mol, and preferably 5 to 15 mol. The time of the conversion reaction is 0.1 to 48 hours, and preferably 0.5 to 24 hours. The reaction temperature is 0 to 200° C., and preferably 50 to 120° C. The compound of the formula (VI) obtained by this step can be separated and purified by a known means for separation and purification, for example, concentration, concentration under reduced pressure, crystallization, re-precipitation, and chromatography, or it can be subjected to the next step without any separation and purification.

(Step 4)

This step is a step for obtaining a compound of the formula (Ia) by linking the compound of the formula (vI) to the compound of the formula (VII). The reaction of this step is performed by using a metal catalyst and a phosphine ligand in a suitable solvent, in the presence of various bases. The equivalent of the compound of the formula (VII) is, relative to 1 mol of the compound of the formula (VI), 0.1 to excess mol, and preferably 1 to 10 mol. As the metal catalyst, a metal complex having various ligands can be used, and examples thereof include tetrakistriphenylphosphine palladium (0), chlorobis(triphenylphosphine)palladium (II), tris (dibenzylideneacetone)dipalladium (0), and palladium acetate (II). Examples of the phosphine ligand include dppf, Xantphos, and XPhos. Examples of the base used for the reaction of this step include potassium carbonate, cesium carbonate, and sodium tert-butoxide. The solvent which can be used for this step is not particularly limited as long as it does not cause any problem on the reaction. Examples of the solvent include dioxane, ethyl acetate, and toluene. The amount of the metal catalyst used for the reaction is, relative to 1 mol of the compound of the formula (VI), 0.005 to 10 mol, and preferably 0.01 to 1 mol. The amount of the base is, relative to 1 mol of the compound of the formula (VI), 0.1 to 20 mol and preferably 1.0 to 5.0 mol. The time of the reaction is 0.1 to 48 hours, and preferably 0.5 to 24 hours. The reaction temperature is 0 to 200° C., and preferably 50 to 120° C. The compound of the formula (Ia) obtained by this step can be separated and purified by a known means for separation and purification, for example, concentration, concentration under reduced pressure, crystallization, re-precipitation, and chromatography.

According to another method for this step, the compound represented by the formula (Ia) can be obtained by using only a base without using the metal catalyst and phosphine ligand. Examples of the base include potassium carbonate. The amount of the base is, relative to 1 mol of the compound of the formula (VI), 0.005 to 10 mol, and preferably 1.0 to 5.0 mol. The solvent used for the reaction of this step is not particularly limited as long as it does not cause any problem on the reaction. Examples of the solvent include acetonitrile and dioxane. The time of the reaction is 0.1 to 48 hours, and preferably 0.5 to 24 hours. The reaction temperature is 0 to 200° C., and preferably 50 to 120° C. The compound of the formula (Ia) obtained by this step can be separated and purified by a known means for separation and purification, for example, concentration, concentration under reduced pressure, crystallization, re-precipitation, and chromatography.

As another method for this step, the linking between the compound of the formula (VI) and the compound of the formula (VII) can be performed by using an acid instead of using the metal catalyst and phosphine ligand. The equivalent of the compound of the formula (VII) is, relative to 1 mol of the compound of the formula (VI), 0.1 to excess mol, and preferably 1 to 10 mol. Examples of the acid which is used include paratoluenesulfonic acid, camphorsulfonic acid, and hydrochloric acid. The amount of the acid is, relative to 1 mol of the compound of the formula (VI), 0.005 to excess mol, and preferably 0.1 to 10 mol. The solvent used for the reaction of this step is not particularly limited as long as it does not cause any problem on the reaction. Examples of the solvent include tert-butanol, 2-propanol, THF, and dioxane. The time of the reaction is 0.1 to 48 hours, and preferably 0.1 to 24 hours. The reaction temperature is 0 to 200° C., and preferably 50 to 180° C. The compound of the formula (Ia) obtained by this step can be separated and purified by a known means for separation and purification, for example, concentration, concentration under reduced pressure, crystallization, re-precipitation, and chromatography.

In the production method described above, $R_2$, $Ra$, $Rb$, and $L_2$ each can be subjected to introduction of a protecting group, deprotection, or conversion in an appropriate step according to a common method.

The order of each step of Reaction scheme 1 can be changed. As an alternative method by changing the order of the steps of Reaction scheme 1, the following Reaction scheme 2 can be used.

Reaction scheme 2

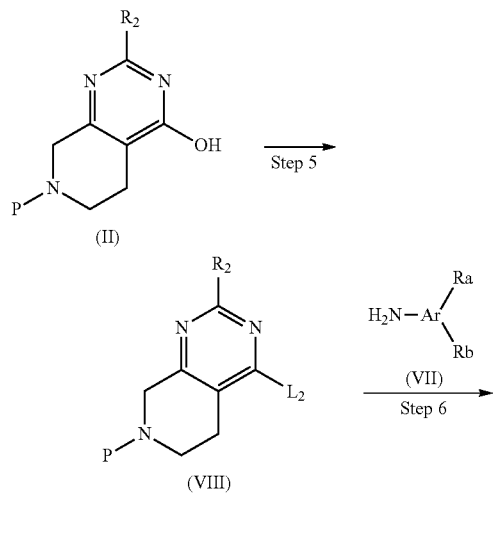

-continued

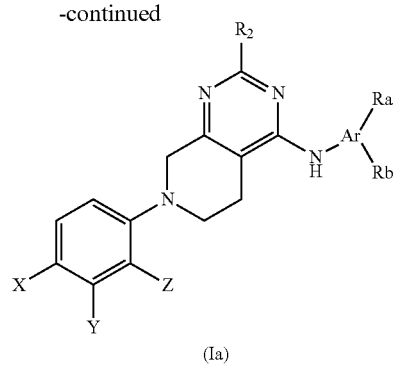

The fused pyrimidine compound represented by the formula (I) (hereinbelow, it may be also referred to as the "compound of the formula (I) of the present invention"), which is obtained by the process described above, may have an optical isomer or a geometric isomer depending on the type of a substituent group, and any of those is also included in the compound of the formula (I) of the present invention. The isomers may be subjected to resolution or used as a mixture of the isomers by themselves. Furthermore, tautomers shown below are present for the fused pyrimidine compound represented by the formula (I), and any of those tautomers is also included in the compound of the formula (I) of the present invention.

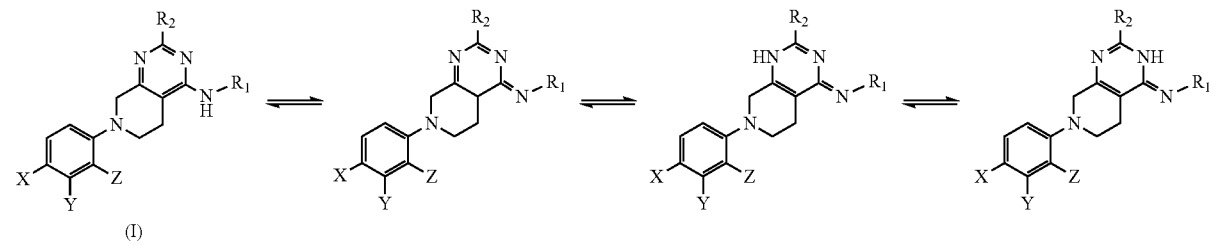

-continued

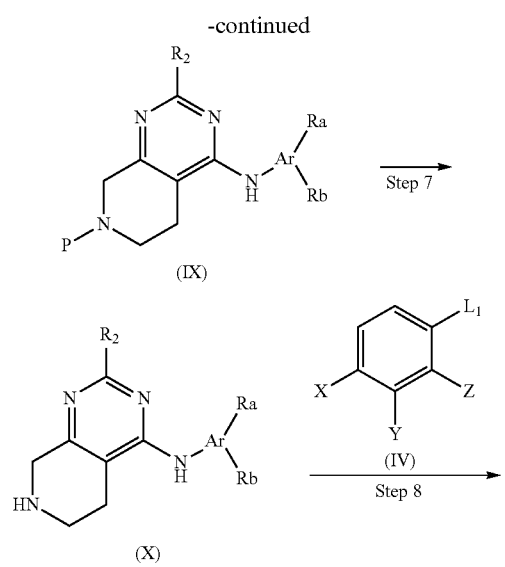

Furthermore, a solvate represented by a hydrate, a non-crystalline (amorphous) or crystalline polymorph is also encompassed by the compound of the formula (I) of the present invention.

The compound of the formula (I) of the present invention may form a salt according to a commonly known method. As for the type of the salt of the compound of the formula (I) of the present invention, any of the aforementioned pharmaceutically acceptable salts is possible.

The compound of the formula (I) of the present invention or a salt thereof can be separated and purified by a known means for separation and purification, for example, concentration, solvent extraction, filtration, recrystallization, or various chromatographies.

When the compound of the formula (I) of the present invention or a pharmaceutically acceptable salt thereof is used as a pharmaceutical agent, various administration forms can be adopted depending on purpose of prevention or treatment. Examples of the administration form include oral and parenteral administration forms, for example, an oral preparation, an injection, a suppository, an external preparation, and a patch. Preferably, an oral preparation is used.

Each of those administration forms can be produced by a formulation method that is generally known to a person skilled in the art.

The pharmaceutical agent can be a pharmaceutical composition containing an effective amount of the compound of the formula (I) of the present invention or a pharmaceutically acceptable salt, and a pharmaceutically acceptable carrier. As for the pharmaceutically acceptable carrier, various organic or inorganic carrier substances that are generally used as a material for formulation are used, and for a solid formulation, for example, there may be mentioned a vehicle, a lubricating agent, a binding agent, and a disintegrating agent, and for a liquid formulation, there may be mentioned a solvent, a dissolution aid, a suspending agent, an isotonic agent, a buffer agent, a stabilizing agent, a pH controlling agent, a surfactant, a wetting agent, a preservative, and a pain relieving agent. Furthermore, the pharmaceutical agent may contain formulation additives such as a preservative, an anti-oxidant, a coloring agent, a sweetening agent, and a flavoring agent, if necessary.

The pharmaceutically acceptable carrier or formulation additives can be those that are generally used in the pertinent field. Examples of the vehicle include lactose, white sugar, sodium chloride, glucose, starch, calcium carbonate, kaolin, microcrystalline cellulose, and silicic acid; examples of the binding agent include water, ethanol, propanol, sweet syrup, glucose solution, starch solution, gelatin solution, carboxymethyl cellulose, hydroxypropyl cellulose, hydroxypropyl starch, methyl cellulose, ethyl cellulose, shellac, calcium phosphate, and polyvinylpyrrolidone; examples of the disintegrating agent include dry starch, sodium alginate, agar powder, sodium hydrogen carbonate, calcium carbonate, sodium lauryl sulfate, stearic acid monoglyceride, and lactose; examples of the lubricating agent include purified talc, stearic acid salt, borax, and polyethylene glycol; examples of the coloring agent include titanium oxide and iron oxide; and examples of the flavoring agent include white sugar, orange peel, citric acid, and tartaric acid.

For producing a solid formulation for oral administration, the compound of the formula (I) of the present invention or a pharmaceutically acceptable salt thereof is added with a vehicle, and if necessary, with a binding agent, a disintegrating agent, a lubricating agent, a coloring agent, a flavoring agent, or the like, and prepared as a tablet, a coated tablet, a granule, a powder, or a capsule, for example, according to a commonly used method.

For producing a liquid formulation for oral administration, the compound of the formula (I) of the present invention or a pharmaceutically acceptable salt thereof is added with a flavoring agent, a buffer agent, a stabilizing agent, or the like, and prepared as an internal liquid medicine, a syrup, or an elixir, for example. In that case, the flavoring agent may be the same as those described above; examples of the buffer agent include sodium citrate; and examples of the stabilizing agent include tragacanth, gum Arabic, and gelatin.

For producing an injection, the compound of the formula (I) of the present invention or a pharmaceutically acceptable salt thereof is added with a pH controlling agent, a buffer agent, a stabilizing agent, an isotonic agent, a local anesthetic, or the like, and prepared as a subcutaneous, intramuscular, or intravenous injection according to a commonly used method. In that case, examples of the pH controlling agent and buffer agent include sodium citrate, sodium acetate, and sodium phosphate; examples of the stabilizing agent include sodium pyrosulfite, EDTA, thioglycolic acid, and thiolactic acid; examples of the local anesthetic include procaine hydrochloride and lidocaine hydrochloride; and examples of the isotonic agent include sodium chloride and glucose.

For producing a suppository, the compound of the formula (I) of the present invention or a pharmaceutically acceptable salt thereof is added with a known carrier for formulation, e.g., polyethylene glycol, lanolin, kakao fat, and a fatty acid triglyceride, and if necessary, a surfactant such as Tween (registered trademark), and production is performed according to a common method.

For producing an external preparation such as an ointment, a cream, a gel, or a paste, the compound of the formula (I) of the present invention or a pharmaceutically acceptable salt thereof is added with, if necessary, a commonly used base, a stabilizing agent, a wetting agent, or a preservative, and mixing and formulating are performed according to a common method. Examples of the base include fluid paraffin, white vaseline, white beeswax, octyl dodecyl alcohol, and paraffin. Examples of the preservative include methyl paraoxybenzoate, ethyl paraoxybenzoate, and propyl paraoxybenzoate.

For producing a patch, the ointment, cream, gel, or paste, for example, are coated on a common support according to a common method. Examples of the support include a woven or non-woven fabric consisting of cotton, staple fiber, or chemical fiber, or a film or a foamed sheet of soft vinyl chloride, polyethylene, and polyurethane.

The amount of the compound of the formula (I) of the present invention or a pharmaceutically acceptable salt thereof which needs to be blended in each administration unit form described above varies depending on symptom, weight, age, or sex of a subject for application, or a formulation type, for example. However, in terms of the amount of the compound of the formula (I) of the present invention, it is preferably 0.05 to 1000 mg for an oral preparation, 0.01 to 500 mg for an injection, and 1 to 1000 mg for a suppository. Furthermore, the daily dose of above administration form varies depending on species, symptom, weight, age, or sex of a subject for application. However, in terms of the amount of the compound of the formula (I) of the present invention, it is preferably 0.05 to 5000 mg, and preferably 0.1 to 1000 mg per day for an adult, and it is preferably administered once or in about 2 to 4 divided doses per day. With regard to the compound of the formula (I) of the present invention or a pharmaceutically acceptable salt, any one type of the compound or a salt may be used singly or a plurality of types may be used in combination.

As described herein, the anti-androgen activity means an activity of suppressing the androgen activity, and a compound, a composition, or a pharmaceutical agent having the anti-androgen activity is referred to as an anti-androgen agent. The compound of the formula (I) of the present invention or a pharmaceutically acceptable salt thereof acts as an antagonist for an androgen receptor (AR) and suppresses the response of AR to androgen, thus exhibiting the anti-androgen activity. Furthermore, as the compound of the formula (I) of the present invention or a salt thereof also has an activity of reducing AR expression, it can exhibit an anti-androgen activity based on it. By having the anti-androgen activity, the compound of the formula (I) of the present invention or a pharmaceutically acceptable salt thereof exhibits the effect of suppressing an occurrence or progress of various disorders, an occurrence of tumor, or progress or recurrence of a progressive or recurrent tumor.

Thus, according to another embodiment, provided by the present invention is an anti-androgen agent which contains, as an active ingredient, the compound of the formula (I) of the present invention or a pharmaceutically acceptable salt. Also provided by the present invention is use of the compound of the formula (I) of the present invention or a pharmaceutically acceptable salt thereof for producing an anti-androgen agent. Also provided by the present invention is use of the compound of the formula (I) of the present invention or a pharmaceutically acceptable salt thereof as an anti-androgen agent. Also provided by the present invention is the compound of the formula (I) of the present invention or a pharmaceutically acceptable salt thereof for use as an anti-androgen agent.

According to another embodiment, provided by the present invention is a pharmaceutical agent which contains, as an active ingredient, the compound of the formula (I) of the present invention or a pharmaceutically acceptable salt. Also provided by the present invention is use of the compound of the formula (I) of the present invention or a pharmaceutically acceptable salt thereof for producing a pharmaceutical agent. Also provided by the present invention is use of the compound of the formula (I) of the present invention or a pharmaceutically acceptable salt thereof as a pharmaceutical agent. Also provided by the present invention is the compound of the formula (I) of the present invention or a pharmaceutically acceptable salt thereof for use as a pharmaceutical agent.

According to another embodiment, provided by the present invention is a pharmaceutical composition which contains the compound of the formula (I) of the present invention or a pharmaceutically acceptable salt, and a pharmaceutically acceptable carrier.

According to a preferred embodiment, the pharmaceutical agent or pharmaceutical composition is used as an anti-androgen agent. Furthermore, according to a preferred embodiment, the pharmaceutical agent or pharmaceutical composition is a therapeutic agent for a disorder related with AR activation. Furthermore, according to a preferred embodiment, the pharmaceutical agent or pharmaceutical composition is an anti-tumor agent.

Meanwhile, according to another embodiment, provided by the present invention is a method of suppressing androgen activity including administering an effective amount of the compound of the formula (I) of the present invention or a pharmaceutically acceptable salt thereof to a subject. Also provided by the present invention is a method for treating a disorder related with AR activation including administering an effective amount of the compound of the formula (I) of the present invention or a pharmaceutically acceptable salt thereof to a subject. Also provided by the present invention is a method for treating tumor including administering an effective amount of the compound of the formula (I) of the present invention or a pharmaceutically acceptable salt thereof to a subject.

With regard to a method for suppressing androgen activity, a method for treating a disorder related with AR activation, and a method for treating tumor according to the present invention, examples of the subject include a human or a non-human animal in need of the method. Examples of the non-human animal include primates such as a monkey and a chimpanzee, and mammals such as a mouse, a rat, a hamster, a guinea pig, a dog, a cat, a cow, a horse, a sheep, a goat, and a pig; however, it is not limited thereto.

The effective amount or administration regimen of the compound of the formula (I) of the present invention or a pharmaceutically acceptable salt thereof administered to the above subject can be suitably determined by a person skilled in the art depending on, for example, species, symptom, weight, age, or sex, of the subject. For example, when the subject is an adult human, it is usually administered at 0.05 to 5000 mg, and preferably 0.1 to 1000 mg per day in terms of the amount of the compound of the formula (I) of the present invention, and it is preferably administered once or in about 2 to 4 divided doses per day.

Examples of the disorder related with AR activation include tumor, metastatic bone disease, prostatic hyperplasia, acne vulgaris, seborrhea, hypertrichosis, androgenetic alopecia, precocious puberty, and virillizing syndrome. Examples of the tumor include prostate cancer, breast cancer, ovarian cancer, bladder cancer, uterine cancer, pancreatic cancer, and hepatocellular cancer. It is preferably prostate cancer. Meanwhile, the tumor also includes resistant, recurrent, or metastatic tumor. Thus, specific examples of the prostate cancer include, in addition to common prostate cancer, castration resistant prostate cancer (CRPC), hormone resistant prostate cancer (HRPC), PSA recurrent prostate cancer, taxan resistant prostate cancer, and radiation resistant prostate cancer. It is preferably castration resistant prostate cancer.

Examples of a conventional anti-androgen agent include bicalutamide. However, as they have an agonist activity for AR, the effect is not maintained for a long period of time, and recurrent cancer is observed 2 to 5 years after the response. Furthermore, in CRPC, overexpression of AR is believed to be a cause of recurrence. The compound of the formula (I) of the present invention or a salt thereof has a potent antagonist activity for AR but no agonist activity therefor, and it exhibits a strong AR antagonist activity for cells in which AR is overexpressed. Furthermore, by having the activity of reducing AR expression in addition to the antagonist activity for AR, the compound of the formula (I) of the present invention or a salt thereof is effective for cancer having overexpressed AR such as CRPC.

Hereinbelow, the present invention is described specifically by way of Examples and Test Examples. However, they are described solely for exemplification, and the scope of the present invention is not limited to them.

Production Example

In the following examples, each reagent used was commercially available one, unless specifically described otherwise. For silica gel column chromatography, Biotage (registered trademark) SNAP Ultra pre-packed column or Biotage (registered trademark) SNAP KP-NH pre-packed column (both manufactured by Biotage AB) was used. Reverse phase preparative HPLC column chromatography was performed at the following conditions.
Column: YMC-Actus Triart C18 manufactured by YMC, 30×50 mm, 5 μm
UV detection: 254 nm
Column flow rate: 40 mL/min
Mobile phase: water/acetonitrile (0.1% formic acid)
Injection volume: 1.0 mL
Gradient: water/acetonitrile 10%→90% (8 minutes)

For $^1$H-NMR spectrum measurement, AL400 (400 MHz; JEOL Ltd. (JEOL)), or Mercury400 (400 MHz; Agilent Technologies, Inc.) type spectrometer was used. For obtaining $^1$H-NMR spectrum, measurement was made using TMS (tetramethylsilane) as an internal standard, and chemical shift was represented in terms of δ value (ppm). With regard to the chemical shift, number of protons, absorption pattern, and coupling constant (J value) were described in parentheses. With regard to the absorption pattern, the following symbols were used: s=singlet, d=doublet, t=triplet, q=quartet, sept=septet, dd=double doublet, dt=double triplet, dq=double quartet, m=multiplet, br-s=broad singlet, br-d=broad doublet, br-t=broad triplet, br-dd=broad double doublet.

LCMS spectra were measured with an SQD manufactured by Waters Corporation under the following two conditions, and the retention time (RT) (min) and [M+H]⁺ value were shown.

MS detection: ESI positive
UV detection: 254 nm
Column flow rate: 0.5 mL/min
Mobile phase: water/acetonitrile (0.1% formic acid)
Injection volume: 1 μL
Method A
Column: Acguity BEH, 2.1×50 mm, 1.7 μm
Gradient:

| Time (min) | water/acetonitrile (0.1% formic acid) |
|---|---|
| 0 | 95/5 |
| 0.1 | 95/5 |
| 2.1 | 5/95 |
| 3.0 | STOP |

Method B
Column: Acguity BEH, 2.1×50 mm, 1.7 μm
Gradient:

| Time (min) | water/acetonitrile (0.1% formic acid) |
|---|---|
| 0 | 95/5 |
| 0.1 | 95/5 |
| 1.1 | 5/95 |
| 2.0 | STOP |

With regard to the structural formula of compounds, the following symbols may be used: Me=methyl, Et=ethyl, tBu=tert-butyl, Ph=phenyl, Bn=benzyl, Ac=acetyl, Boc=tert-butoxy carbonyl, Ms=methanesulfonyl.

With regard to the solvent and reagent, the following abbreviations may be used:
DMSO=dimethyl sulfoxide;
DMF=N,N-dimethylformamide;
THF=tetrahydrofuran;
dba=dibenzylideneacetone;
dppf=1,1-bis(diphenylphosphino) ferrocene;
XantPhos=4,5-bis(diphenylphosphino)-9,9-dimethylxanthene;
Boc₂O=di-tert-butyl dicarbonate;
DMAP=4-dimethylaminopyridine;
TFA=trifluoroacetic acid;
DIPEA=diisopropylethylamine;
DMT-MM=4-(4,6-dimethoxy-1,3,5-triazin-2-yl)-4-methylmorpholinum chloride;
HATU=O-(7-azabenzotriazol-1-yl)-N,N,N',N'-tetramethyluroniumhexafluorophosphate;
HOBt=1-hydroxybenzotriazole;
mCPBA=3-chloroperbenzoic acid
WSC=EDCI=1-ethyl-3-(3-dimethylaminopropyl)carbodiimide;
DBU=1,8-diazabicyclo[5,4,0]undecene;
NMP=N-methyl-2-pyrrolidone;
DMA=dimethylacetamide;
DCC=N,N'-dicyclohexylcarbodiimide;
DPPA=diphenylphosphoryl azide;
LDA=lithium diisopropylamide.

Reference Example 1

4-(4-Chloro-5,6-dihydropyrido[3,4-d]pyrimidin-7(8H)-yl)-2-(trifluoromethyl)benzonitrile

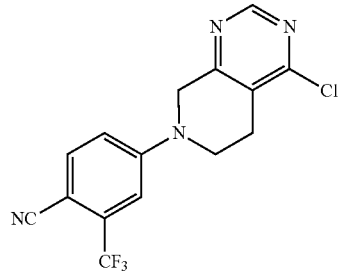 [SMILES: N#Cc1ccc(N2CCc3c(Cl)ncnc3C2)cc1C(F)(F)F]

(Step 1) 4-(4-Hydroxy-5,6-dihydropyrido[3,4-d]pyrimidin-7(8H)-yl)-2-(trifluoromethyl)benzonitrile

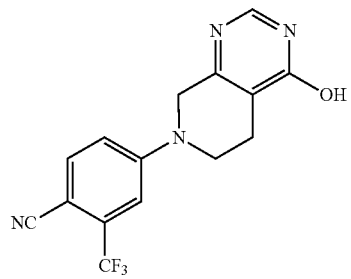 [SMILES: N#Cc1ccc(N2CCc3c(O)ncnc3C2)cc1C(F)(F)F]

Commercially available 7-benzyl-5,6,7,8-tetrahydropyrido[3,4-d]pyrimidin-4-ol (12.6 g), 10% palladium/carbon (2 g), and ammonium formate (16.5 g) were suspended in methanol (200 mL), followed by stirring overnight at 60° C. The reaction mixture was filtered through Celite to remove insolubles, and the filtrate was concentrated. The resulting residue was used in the subsequent reaction without purification. The resulting compound and 4-fluoro-2-(trifluoromethyl)benzonitrile (10 g) were suspended in DMSO (150 mL), followed by stirring at room temperature overnight. Water (200 mL) was added to the reaction mixture, and the solid was collected by filtration. The resulting solid was suspended and washed with 100 mL of ethyl acetate, followed by drying by heating to obtain the target compound.

¹H-NMR (DMSO-d6) δ12.35 (1H, br-s), 8.09 (1H, S), 7.85 (1H, d, J=8.0 Hz), 7.39 (1H, s), 7.32 (1H, d, J=8.0 Hz), 4.34 (2H, s), 3.71 (2H, t, J=4.0), 2.56 (2H, t, J=4.0 Hz). LCMS (A) RT 1.37, m/z [M+H]⁺ 321.

(Step 2) 4-(4-Chloro-5,6-dihydropyrido[3,4-d]pyrimidin-7(8H)-yl)-2-(trifluoromethyl)benzonitrile

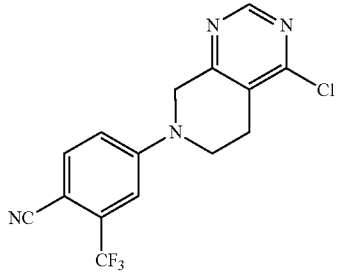

The solid (12.3 g) obtained in step 1 was suspended in dichloroethane (60 mL), and added with phosphorus oxychloride (36 mL) and triethylamine (12 mL), followed by stirring for 30 minutes at 90° C. The reaction mixture was added to water (300 mL), and the mixture was adjusted to pH 7 with sodium carbonate, followed by extraction with chloroform (300 mL×three times). The extract was dried over magnesium sulfate and was then concentrated, and the resulting solid was suspended and washed with ethyl acetate to obtain 9.4 g (72%) of the target compound.

$^1$H-NMR (DMSO-d6) δ8.89 (1H, s), 7.89 (1H, d, J=8.0 Hz), 7.47 (1H, s), 7.40 (1H, d, J=8.0 Hz), 4.73 (2H, s), 3.90 (2H, t, J=4.0), 2.94 (2H, t, J=4.0 Hz).

LCMS (A) RT 1.81, m/z[M+H]$^+$ 339/341.

Reference Example 2

2-Chloro-4-(4-chloro-5,6-dihydropyrido[3,4-d]pyrimidin-7(8H)-yl)benzonitrile

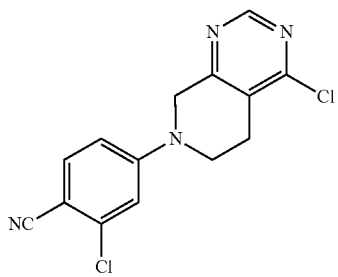 [SMILES: N#Cc1ccc(N2CCc3c(Cl)ncnc3C2)cc1Cl]

Commercially available 5,6,7,8-tetrahydropyrido[3,4-d]pyrimidin-4-ol hydrochloride (10.0 g), 2-chloro-4-fluorobenzonitrile (8.1 g), and triethylamine (22 mL) were added to DMSO (183 mL) and stirred for 2 days at room temperature. After adding water (400 mL), the reaction mixture was adjusted to pH 4 to 6 using conc. hydrochloric acid, and the precipitated solid was collected by filtration. The obtained solid was suspended and washed with ethyl acetate, followed by drying. Phosphorus oxychloride (15 mL) was added to the resulting solid (6.4 g), and the reaction mixture was heated to reflux for 10 minutes. The reaction mixture was concentrated under reduced pressure, water (400 mL) was added to the residue, and the aqueous layer was adjusted to pH 8 with sodium carbonate. The precipitated solid was collected by filtration, was dried, and was suspended and washed with toluene to obtain the target compound.

$^1$H-NMR (DMSO-d6) δ8.87 (1H, s), 7.70 (1H, d, J=8.9 Hz), 7.32 (1H, d, J=2.3 Hz), 7.12 (1H, dd, J=8.9, 2.3 Hz), 4.66 (2H, s), 3.83 (2H, t, J=5.8 Hz), 2.90 (2H, t, J=5.8 Hz).

LCMS (A) RT 1.75, m/z[M+H]$^+$ 305/307.

Reference Example 3

4-Chloro-7-(4-nitro-3-(trifluoromethyl)phenyl)-5,6,7,8-tetrahydropyrido[3,4-d]pyrimidine

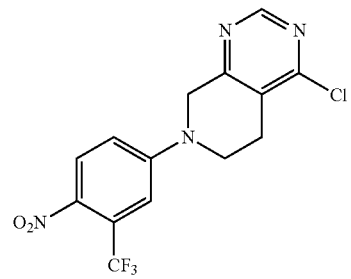 [SMILES: O=[N+]([O-])c1ccc(N2CCc3c(Cl)ncnc3C2)cc1C(F)(F)F]

The target compound was obtained by the same procedure as Reference Example 1 except that 4-fluoro-1-nitro-2-(trifluoromethyl)benzene was used instead of 4-fluoro-2-(trifluoromethyl)benzonitrile.

$^1$H-NMR (CDCl$_3$) δ: 8.86 (1H, s), 8.08 (1H, d, J=9.2 Hz), 7.27-7.24 (1H, m), 7.06 (1H, dd, J=9.3, 2.7 Hz), 4.64 (2H, s), 3.86 (2H, t, J=5.9 Hz), 3.09 (2H, t, J=5.7 Hz).

LCMS (A) RT 1.87, m/z [M+H]$^+$ 359/361.

Reference Example 4

2-(6-((5,6,7,8-Tetrahydropyrido[3,4-d]pyrimidin-4-yl)amino)pyridin-3-yl)propan-2-ol

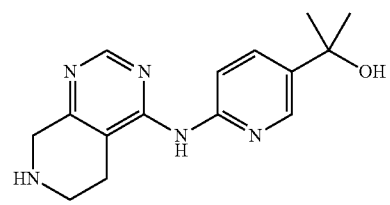 [SMILES: CC(C)(O)c1ccc(Nc2ncnc3c2CCNC3)nc1]

(Step 1) Methyl 6-((7-benzyl-5,6,7,8-tetrahydropyrido[3,4-d]pyrimidin-4-yl)amino) nicotinate

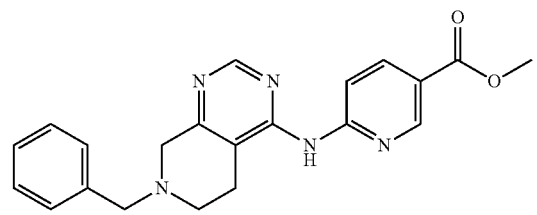 [SMILES: COC(=O)c1ccc(Nc2ncnc3c2CCN(Cc2ccccc2)C3)nc1]

Commercially available 7-benzyl-4-chloro-5,6,7,8-tetrahydropyrido[3,4-d]pyrimidine (48 g), methyl 6-aminonicotinate (31 g), Pd(dba)$_2$ (10.6 g), dppf (10.2 g), and cesium carbonate (133 g) were suspended in dioxane (1000 mL), and the reaction mixture was stirred under an argon atmosphere at 105° C. for 3 hours. The reaction mixture was cooled, and the precipitated solid was then collected by filtration and was suspended and washed with toluene to obtain the target compound as a light yellow solid.

$^1$H-NMR (DMSO-d6) δ: 9.39 (1H, s), 8.84 (1H, d, J=2.6 Hz), 8.57 (1H, s), 8.32 (1H, d, J=9.2 Hz), 8.26 (1H, d, J=2.6 Hz), 7.36-7.36 (5H, m), 3.85 (3H, s), 3.68 (2H, s), 2.77 (2H, d, J=4.8 Hz), 2.74 (2H, d, J=4.4 Hz). LCMS (A) RT 1.09, m/z [M+H]$^+$ 376.

(Step 2) 2-(6-((7-Benzyl-5,6,7,8-tetrahydropyrido[3,4-d]pyrimidin-4-yl)amino)pyridin-3-yl)propan-2-ol

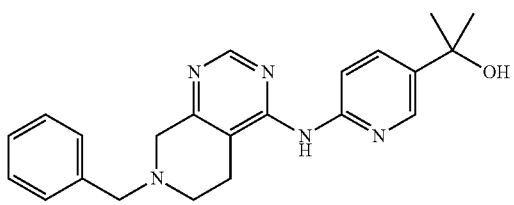 [SMILES: CC(C)(O)c1ccc(Nc2ncnc3c2CCN(Cc2ccccc2)C3)nc1]

Methylmagnesium bromide (3 mol/L ether solution, 60 mL) was dropwise added under ice cooling to a THF (400 mL) solution of the compound (15 g) obtained in step 1. The ice bath was removed after completion of the dropwise addition. The reaction mixture was stirred at room temperature for 2 hours, and 2 mol/L hydrochloric acid was added to the reaction mixture, followed by extraction with ethyl acetate. The organic layer was washed with saturated brine, was dried over magnesium sulfate, and was then concentrated under reduced pressure. The resulting residue was purified by silica gel column chromatography (eluent: chloroform-methanol) to obtain the target compound as a white solid.

$^1$H-NMR (DMSO-d6) δ: 8.78 (1H, s), 8.43 (1H, s), 8.40 (1H, d, J=2.2 Hz), 8.07 (1H, d, J=8.4 Hz), 7.82 (1H, dd, J=8.6, 2.4 Hz), 7.38-7.25 (5H, m), 5.16 (1H, s), 3.67 (2H, s), 2.72 (4H, s), 1.45 (6H, s).

LCMS (A) RT 0.81, m/z [M+H]-376.

(Step 3) 2-(6-((5,6,7,8-Tetrahydropyrido[3,4-d]pyrimidin-4-yl)amino)pyridin-3-yl)propan-2-ol

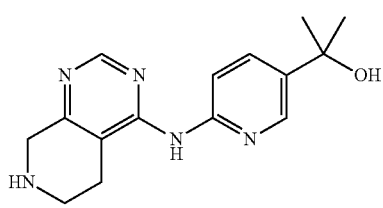 [SMILES: CC(C)(O)c1ccc(Nc2ncnc3c2CCNC3)nc1]

The compound (25 g) obtained in step 2, palladium hydroxide (50% wet) (9.3 g), and ammonium formate (33.6 g) were suspended in methanol (620 mL), and the reaction mixture was stirred at 60° C. for 1.5 hours. The reaction mixture was filtered through Celite to remove insolubles, and the filtrate was concentrated under reduced pressure to obtain the target compound as a white solid. $^1$H-NMR (DMSO-d6) δ: 8.71 (1H, s), 8.44 (1H, s), 8.40 (1H, d, J=2.2 Hz), 8.06 (1H, d, J=8.8 Hz), 7.82 (1H, dd, J=8.6, 2.4 Hz), 5.16 (1H, s), 3.72 (2H, s), 3.16 (1H, s), 2.99 (2H, t, J=5.9 Hz), 2.59 (2H, t, J=5.7 Hz), 1.45 (61H, s).

LCMS (A) RT 0.43, m/z [M+H]$^+$ 286.

Reference Example 5

6-((7-(3-Chloro-4-cyanophenyl)-5,6,7,8-tetrahydropyrido[3,4-d]pyrimidin-4-yl)amino)-2-fluoronicotinic acid

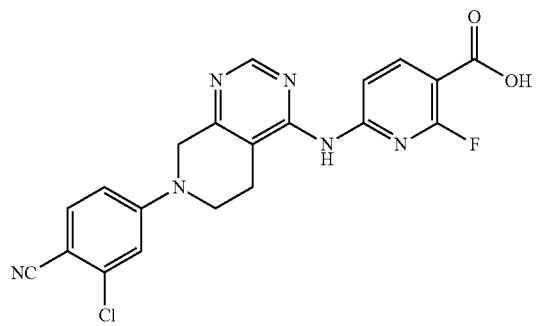 [SMILES: N#Cc1ccc(N2CCc3c(ncnc3Nc3ccc(C(=O)O)c(F)n3)C2)cc1Cl]

(Step 1) Methyl 6-((7-(3-chloro-4-cyanophenyl)-5,6,7,8-tetrahydropyrido[3,4-d]pyrimidin-4-yl)amino)-2-fluoronicotinate

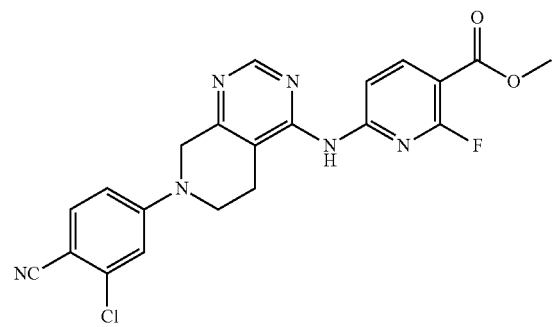 [SMILES: COC(=O)c1ccc(Nc2ncnc3c2CCN(c2ccc(C#N)c(Cl)c2)C3)nc1F]

The compound (88 mg) obtained in Reference Example 2, commercially available 6-amino-2-fluoronicotinic acid methyl ester (35 mg), Pd$_2$(dba)$_3$ (19 mg), dppf (23 mg), and cesium carbonate (201 mg) were suspended in dioxane (0.7 mL), and the reaction mixture was stirred under microwave irradiation at 140° C. for 50 minutes. The filtrate was concentrated under reduced pressure, and the residue was then purified by reversed-phase preparative HPLC column chromatography. The resulting fraction was concentrated under reduced pressure to obtain the target compound as a dark brown solid.

$^1$H-NMR (CDCl$_3$) δ: 8.76 (1H, s), 8.56 (1H, dd, J=8.4, 1.5 Hz), 8.43 (1H, t, J=8.8 Hz), 7.53 (1H, d, J=8.8 Hz), 7.38 (1H, s), 7.00 (1H, d, J=2.6 Hz), 6.85 (1H, dd, J=8.8, 2.6 Hz), 4.49 (2H, s), 3.95 (3H, s), 3.82 (2H, t, J=5.7 Hz), 2.84 (2H, t, J=5.7 Hz).

LCMS (A) RT 1.83, m/z [M+H]$^+$ 439/441.

(Step 2) 6-((7-(3-Chloro-4-cyanophenyl)-5,6,7,8-tetrahydropyrido[3,4-d]pyrimidin-4-yl)amino)-2-fluoronicotinic acid

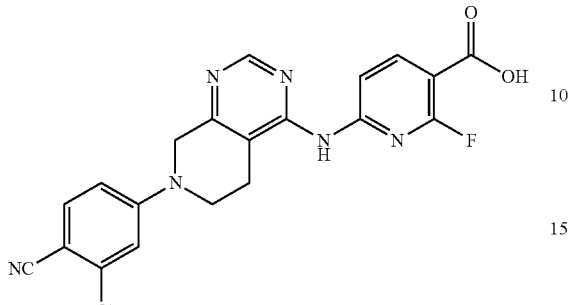

An aqueous solution (0.5 mL) of 5.0 mol/L sodium hydroxide was added to an ethanol (0.5 mL) solution of the compound (10 mg) obtained in step 1 at room temperature, and the reaction mixture was then stirred at 40° C. for 1 hour. The reaction mixture was cooled, and 5.0 mol/L hydrochloric acid (0.55 mL) was added thereto. The precipitated solid was collected by filtration to obtain the target compound.

$^1$H-NMR (DMSO-d6) δ: 9.23 (1, s), 8.60 (1H, s), 8.12 (1H, t, J=9.2 Hz), 7.98 (1H, d, J=8.1 Hz), 7.68 (1H, d, J=9.2 Hz), 7.31 (1H, d, J=1.8 Hz), 7.11 (1H, dd, J=9.2, 1.8 Hz), 4.50 (2H, s), 3.79 (2H, t, J=5.3 Hz), 2.87 (2H, t, J=4.8 Hz).

LCMS (A) RT 1.51, m/z [M+H]$^+$ 425/427.

Reference Example 6

6-((7-(4-Cyano-3-(trifluoromethyl)phenyl)-5,6,7,8-tetrahydropyrido[3,4-d]pyrimidin-4-yl)amino)-2-fluoronicotinic acid

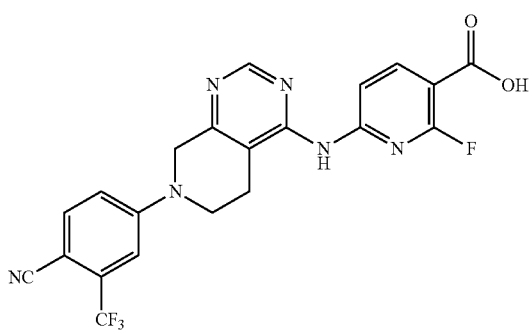 [SMILES: N#Cc1ccc(N2CCc3c(ncnc3Nc3ccc(C(=O)O)c(F)n3)C2)cc1C(F)(F)F]

The target compound was obtained by the same procedure as Reference Example 5 except that Reference Example 1 was used instead of Reference Example 2.

$^1$H-NMR (DMSO-d6) δ: 13.17 (1H, br-s), 9.86 (1H, s), 8.71 (1H, s), 8.35 (1H, dd, J=9.9, 8.8 Hz), 8.14 (1H, dd, J=8.4, 1.8 Hz), 7.87 (1H, d, J=8.8 Hz), 7.45 (1H, d, J=2.6 Hz), 7.38 (1H, dd, J=8.8, 2.6 Hz), 4.61 (2H, s), 3.85 (2H, t, J=5.7 Hz), 2.93 (2H, t, J=5.1 Hz). LCMS (A) RT 1.62, m/z [M+H]$^+$ 459.

Reference Example 7

6-((7-(4-Cyano-3-(trifluoromethyl)phenyl)-5,6,7,8-tetrahydropyrido[3,4-d]pyrimidin-4-yl)amino)nicotinic acid

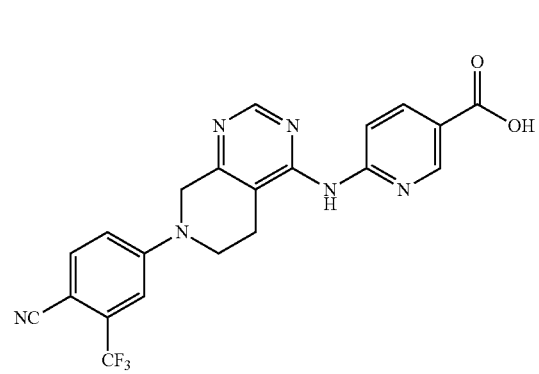 [SMILES: N#Cc1ccc(N2CCc3c(ncnc3Nc3ccc(C(=O)O)cn3)C2)cc1C(F)(F)F]

(Step 1) 6-((7-(4-Cyano-3-(trifluoromethyl)phenyl)-5,6,7,8-tetrahydropyrido[3,4-d]pyrimidin-4-yl)amino) nicotinic acid methyl ester

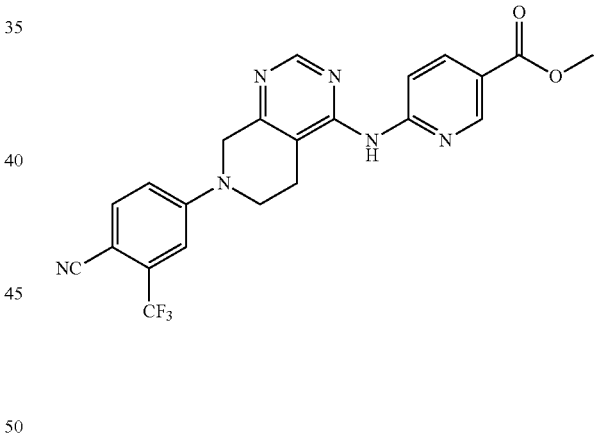

The compound (10.0 g) obtained in Reference Example 1, methyl 6-aminonicotinate (4.49 g), Pd(dba)$_2$ (1.70 g), dppf (1.64 g), and cesium carbonate (24.1 g) were suspended in dioxane (120 mL), and the reaction mixture was stirred under a nitrogen atmosphere at 80° C. overnight. The reaction mixture was cooled, and water was then added thereto. The precipitated solid was collected by filtration, and the resulting solid was purified by silica gel column chromatography to obtain 9.42 g (70%) of the target compound.

$^1$H-NMR (DMSO-d6) δ9.63 (1H, s), 8.82 (1H, s), 8.65 (1H, s), 8.27-8.21 (2H, m), 7.85 (1H, d, J=8.8 Hz), 7.42 (1H, d, J=2.0 Hz), 7.35 (1H, dd, J=8.8, 2.0 Hz), 4.57 (2H, s), 3.85-3.80 (5H, m), 2.91 (2H, t, 5.2 Hz).

LCMS (A) RT 1.77, m/z [M+H]$^+$ 455.

(Step 2) 6-((7-(4-Cyano-3-(trifluoromethyl)phenyl)-5,6,7,8-tetrahydropyrido[3,4-d]pyrimidin-4-yl)amino) nicotinic acid

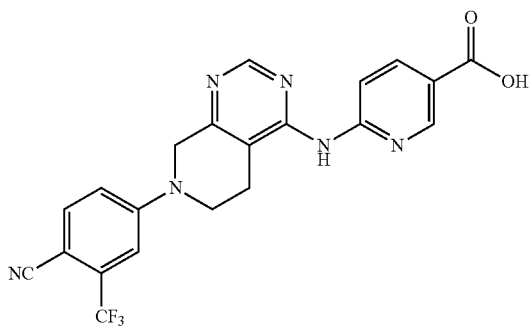

An aqueous solution (11 mL) of 5.0 mol/L sodium hydroxide was added to a methanol (100 mL) suspension of the compound (9.21 g) obtained in step 1, and the reaction mixture was then stirred at 40° C. overnight. The reaction mixture was cooled and was adjusted to pH about 3 with 5.0 mol/L hydrochloric acid. The precipitated solid was collected by filtration, was washed with water, and was dried under reduced pressure to obtain 8.24 g (92%) of the target compound as a crude product.

$^1$H-NMR (DMSO-d6) δ9.59 (1H, s), 8.83 (1H, d, J=2.0 Hz), 8.67 (1H, s), 8.27-8.23 (2H, m), 7.87 (1H, d, J=8.8 Hz), 7.45 (1H, d, J=2.0 Hz), 7.38 (1H, dd, J=2.4, 8.8 Hz), 4.60 (2H, s), 3.86 (2H, t, J=5.6 Hz), 2.93 (2H, t, J=5.6 Hz). LCMS (A) RT 1.48, m/z [M+H]$^+$ 441.

Reference Example 8

6-((7-(4-Cyano-3-(trifluoromethyl)phenyl)-5,6,7,8-tetrahydropyrido[3,4-d]pyrimidin-4-yl)amino)pyridazine-3-carboxylic acid

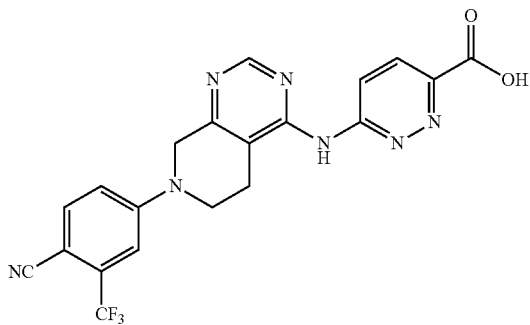 [SMILES: N#Cc1ccc(N2CCc3c(ncnc3Nc3ccc(C(=O)O)nn3)C2)cc1C(F)(F)F]

(Step 1) Methyl 6-((7-(4-cyano-3-(trifluoromethyl)phenyl)-5,6,7,8-tetrahydropyrido[3,4-d]pyrimidin-4-yl)amino)pyridazine-3-carboxylate

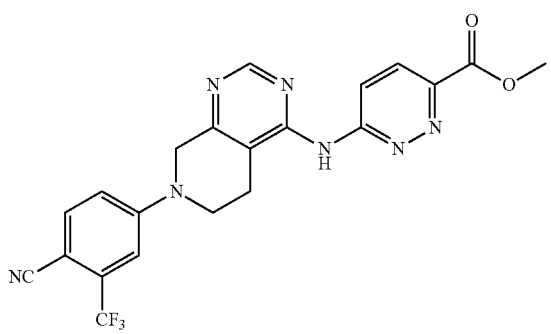 [SMILES: COC(=O)c1ccc(Nc2ncnc3c2CCN(c2ccc(C#N)c(C(F)(F)F)c2)C3)nn1]

By performing the same operation as Reference Example 7 (Step 1) and using a commercially available methyl 6-aminopyridazine-3-carboxylate (100 mg) instead of methyl 6-aminonicotinate, 38 mg of the target compound was obtained.

$^1$H-NMR (DMSO-d6) δ10.39 (1H, s), 8.65 (1H, s), 8.48 (1H, d, J=9.6 Hz), 8.16 (1H, d, J=9.6 Hz), 7.86 (1H, d, J=8.8 Hz), 7.44 (1H, d, J=2.8 Hz), 7.37 (1H, dd, J=8.8, 2.0 Hz), 4.60 (2H, s), 3.91 (3H, s), 3.85 (2H, t, J=6.0 Hz), 2.97 (2H, t, 5.6 Hz).

(Step 2) 6-((7-(4-Cyano-3-(trifluoromethyl)phenyl)-5,6,7,8-tetrahydropyrido[3,4-d]pyrimidin-4-yl)amino)pyridazine-3-carboxylic acid

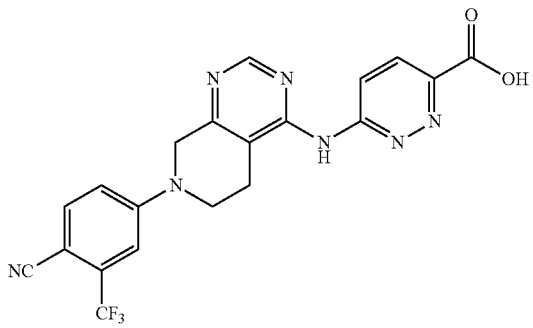

By performing the same operation as Reference Example 7 (Step 2) and using the compound (2.30 g) obtained in this step 1 instead of the compound obtained in Reference Example 7 (Step 1), 2.04 g of the target compound was obtained.

$^1$H-NMR (DMSO-d6) δ10.32 (1H, s), 8.64 (11H, s), 8.45 (1H, d, J=9.6 Hz), 8.13 (1H, d, J=9.2 Hz), 7.86 (1H, d, J=8.8 Hz), 7.44 (1H, d, J=2.4 Hz), 7.37 (1H, dd, J=8.8, 2.4 Hz), 4.60 (2H, s), 3.85 (2H, t, J=5.6 Hz), 2.97 (2H, t, 6.0 Hz). LCMS (A) RT 1.42, m/z [M+H]$^+$ 442.

Reference Example 9 tert-Butyl 4-(3-(4-amino-2-chlorophenoxy)propyl)piperazine-1-carboxylate

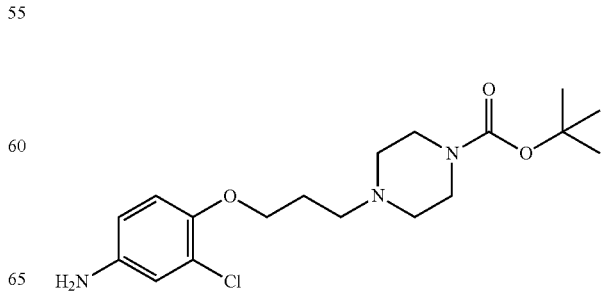

(Step 1) tert-Butyl 4-(3-(2-chloro-4-nitrophenoxy)propyl)piperazine-1-carboxylate

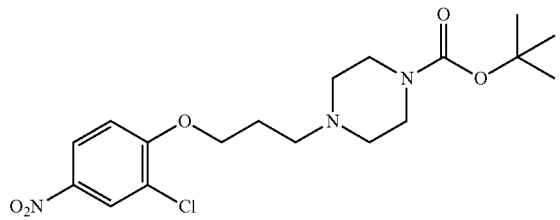 [SMILES: CC(C)(C)OC(=O)N1CCN(CCCOc2ccc(N)cc2Cl)CC1]

2-Chloro-1-fluoro-4-nitrobenzene (320 mg) and sodium hydride (60% in oil, 83 mg) were added to a THF (3 mL) solution of tert-butyl 4-(3-hydroxypropyl)piperazine-1-carboxylate (310 mg) at room temperature, and the reaction mixture was stirred at 70° C. overnight. Water was added to the reaction mixture, followed by extraction with ethyl acetate. The organic layer was washed with water and saturated brine, was dried over sodium sulfate, and was then concentrated under reduced pressure. The resulting residue was purified by silica gel column chromatography (eluent: hexane-ethyl acetate) to obtain the target compound.

$^1$H-NMR (CDCl$_3$) δ 1.46 (9H, s), 1.94-2.04 (2H, m), 2.36-2.44 (4H, m), 2.51 (2H, t, J=7.1 Hz), 3.44 (4H, br-s), 4.11 (2H, t, J=6.2 Hz), 6.87 (1H, dd, J=9.2, 2.6 Hz), 7.03 (1H, d, J=2.6 Hz), 8.00 (1H, d, J=9.2 Hz). LCMS (B) RT 1.01, m/z [M+H]$^+$ 400/402.

(Step 2) tert-Butyl 4-(3-(4-amino-2-chlorophenoxy)propyl) piperazine-1-carboxylate

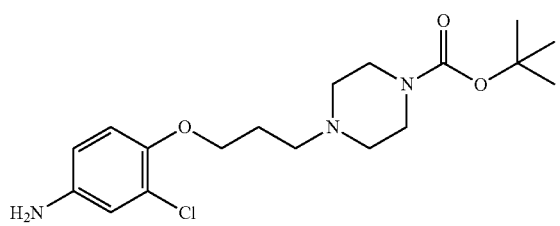 [SMILES: CC(C)(C)OC(=O)N1CCN(CCCOc2ccc(N)cc2Cl)CC1]

Hydrazine monohydrate (1 mL) and developed Raney nickel (0.3 mL) were added to a methanol (10 mL) solution of the compound (180 mg) obtained in step 1 at room temperature, and the reaction mixture was stirred at room temperature overnight. The precipitate was removed by filtration through Celite, and the solvent was then concentrated under reduced pressure to obtain the target compound as a yellow amorphous.

$^1$H-NMR (CDCl$_3$) δ 1.46 (9H, s), 1.89-2.04 (2H, m), 2.35-2.46 (4H, m), 2.55 (2H, br-t, J=7.3 Hz), 3.43 (4H, br-s), 3.99 (2H, brt, J=6.2 Hz), 6.52 (1H, dd, J=8.4, 2.6 Hz), 6.73 (1H, d, J=2.6 Hz), 6.78 (1H, br-d, J=8.4 Hz).

LCMS (B) RT 0.80, m/z [M+H]$^+$ 370/372.

Reference Example 10 tert-Butyl 4-(3-(4-aminophenoxy)propyl)piperazine-1-carboxylate

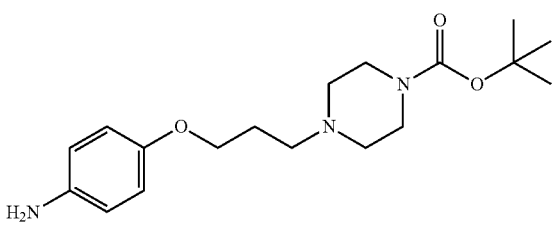 [SMILES: CC(C)(C)OC(=O)N1CCN(CCCOc2ccc(N)cc2)CC1]

The target compound was obtained by the same procedure as Reference Example 9 except that 1-fluoro-4-nitrobenzene was used instead of 2-chloro-1-fluoro-4-nitrobenzene.

$^1$H-NMR (CDCl$_3$) δ 1.46 (9H, s), 1.86-1.98 (1H, m), 2.40 (2H, br-t, J=4.6 Hz), 2.51 (1H, t, J=7.5 Hz), 3.43 (2H, br-t, J=4.6 Hz), 3.94 (1H, t, J=6.2 Hz), 6.63 (1H, d, J=8.8 Hz), 6.74 (1H, d, J=8.8 Hz).

LCMS (B) RT 0.70, m/z [M+H]$^+$ 336.

Reference Example 11 tert-Butyl 4-(3-(4-amino-2-(trifluoromethyl) phenoxy)propyl) piperazine-1-carboxylate

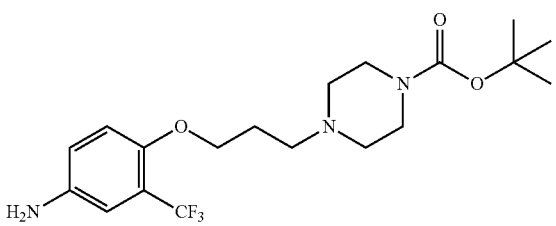

The target compound was obtained by the same procedure as Reference Example 9 except that 1-fluoro-4-nitro-2-(trifluoromethyl)benzene was used instead of 2-chloro-1-fluoro-4-nitrobenzene.

$^1$H-NMR (CDCl$_3$) δ 1.46 (9H, s), 1.90-2.01 (2H, m), 2.40 (4H, br-t, J=4.4 Hz), 2.54 (2H, t, J=7.3 Hz), 3.43 (4H, br-t, J=4.4 Hz), 4.01 (2H, t, J=6.0 Hz), 6.78 (1H, dd, J=8.8, 2.6 Hz), 6.83 (1H, d, J=8.8 Hz), 6.90 (1H, d, J=2.6 Hz).

LCMS (B) RT 0.85, m/z [M+H]$^+$ 404.

Reference Example 12 tert-Butyl 4-(3-(4-amino-3-(trifluoromethyl)phenoxy)propyl)piperazine-1-carboxylate

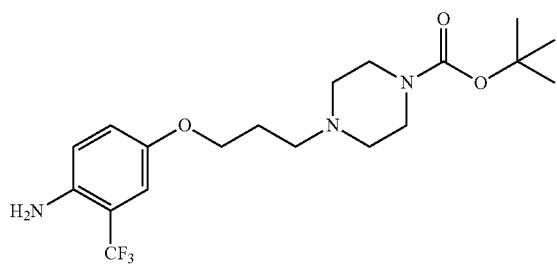 [SMILES: CC(C)(C)OC(=O)N1CCN(CCCOc2ccc(N)c(C(F)(F)F)c2)CC1]

The target compound was obtained by the same procedure as Reference Example 9 except that 1-fluoro-4-nitro-3-(trifluoromethyl)benzene was used instead of 2-chloro-1-fluoro-4-nitrobenzene.

$^1$H-NMR (CDCl$_3$) δ 1.46 (9H, s), 2.40 (4H, br-t, J=4.8 Hz), 2.51 (2H, d, J=6.2 Hz), 3.44 (4H, br-t, J=4.8 Hz), 3.86 (2H, br-s), 3.95 (2H, t, J=6.2 Hz), 6.69 (1H, d, J=8.8 Hz), 6.90 (1H, dd, J=8.8, 2.9 Hz), 6.97 (1H, d, J=2.9 Hz).

LCMS (B) RT 0.98, m/z [M+H]$^+$ 404.

Reference Example 13

N-(4-Methoxyphenyl)-2-(methylthio)-5,6,7,8-tetrahydropyrido[3,4-d]pyrimidin-4-amine

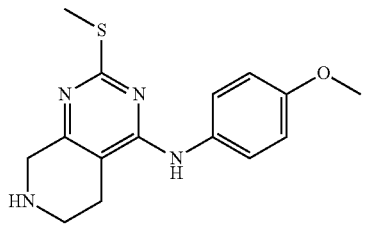 [SMILES: COc1ccc(Nc2nc(SC)nc3c2CCNC3)cc1]

(Step 1) 7-Benzyl-N-(4-methoxyphenyl)-2-(methylthio)-5,6,7,8-tetrahydropyrido[3,4-d]pyrimidin-4-amine

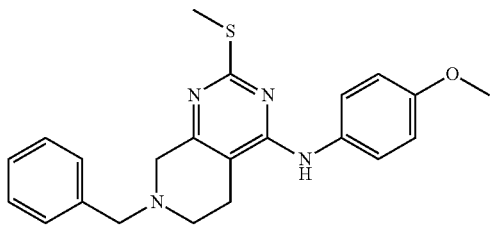 [SMILES: COc1ccc(Nc2nc(SC)nc3c2CCN(Cc2ccccc2)C3)cc1]

Hydroiodic acid (50% aqueous solution, 2.5 mL) was added to a dioxane (30 mL) solution of a commercially available 7-benzyl-4-chloro-2-(methylthio)-5,6,7,8-tetrahydropyrido[3,4-d]pyrimidine (1.57 g), 4-methoxyaniline (756 mg), and sodium iodide (767 mg) at room temperature, and the reaction mixture was stirred at 100° C. overnight. The solution was cooled to room temperature, and the solvent was then distilled off under reduced pressure. Ethyl acetate was added to the residue, and the precipitated residue was collected by filtration to obtain the target compound as a brown solid.

$^1$H-NMR (DMSO-d6) δ 8.81 (1H, s), 7.62-7.71 (2H, m), 7.49-7.52 (5H, m), 6.86-7.01 (2H, m), 3.81-4.67 (1H, m), 3.87-4.03 (6H, m), 3.75 (3H, s), 2.82-3.03 (2H, m), 2.35 (3H, s).

LCMS (B) RT 1.14, m/z [M+H]$^+$ 393.

(Step 2) N-(4-Methoxyphenyl)-2-(methylthio)-5,6,7,8-tetrahydropyrido[3,4-d]pyrimidin-4-amine

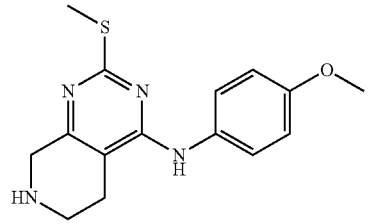 [SMILES: COc1ccc(Nc2nc(SC)nc3c2CCNC3)cc1]

1-chloroethyl chloroformate (0.279 mL) was dropwise added to a 1,2-dichloroethane (10 mL) solution of the compound (507 mg) obtained in step 1 and diisopropylethylamine (0.89 mL) in an ice bath. The ice bath was removed, and the reaction mixture was then stirred at room temperature for 2 hours. The solvent was distilled off under reduced pressure, and methanol (5 mL) was then added thereto. The reaction mixture was stirred at room temperature overnight. The solvent was distilled off under reduced pressure, and chloroform was then added to the residue. The precipitated residue was collected by filtration to obtain the target compound as a white solid.

$^1$H-NMR (CDCl$_3$) δ 7.41-7.50 (2H, m), 6.83-6.94 (2H, m), 6.26 (1H, br-s), 4.49 (2H, br-s), 3.80-3.84 (3H, m), 3.74 (3H, s), 2.52 (2H, br-t, J=5.4 Hz), 2.46 (3H, s).

LCMS (B) RT 0.97, m/z [M+H]$^+$ 303.

Reference Example 14

N-(4-Methoxyphenyl)-2-methyl-5,6,7,8-tetrahydropyrido[3,4-d]pyrimidin-4-amine

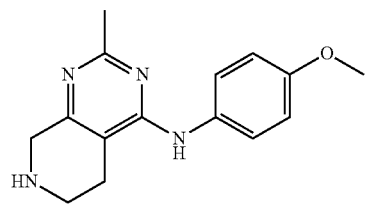 [SMILES: COc1ccc(Nc2nc(C)nc3c2CCNC3)cc1]

(Step 1) 7-Benzyl-N-(4-methoxyphenyl)-2-methyl-5,6,7,8-tetrahydropyrido[3,4-d]pyrimidin-4-amine

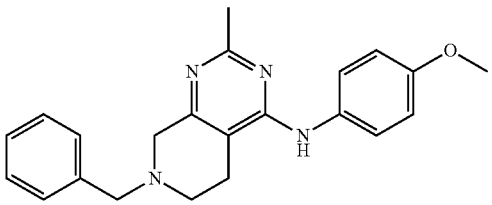 [SMILES: COc1ccc(Nc2nc(C)nc3c2CCN(Cc2ccccc2)C3)cc1]

4-Methoxyaniline (97 mg) was added to an acetonitrile (2 mL) solution of commercially available 7-benzyl-4-chloro-2-methyl-5,6,7,8-tetrahydropyrido[3,4-d]pyrimidine (206 mg) at room temperature, and the reaction mixture was stirred under microwave irradiation at 180° C. for 10 minutes. The solvent was distilled off under reduced pressure, and ethyl acetate was added to the residue. The precipitated residue was collected by filtration to obtain the target compound as a light brown solid.

$^1$H-NMR (CDCl$_3$) δ 7.26-7.56 (8H, m), 6.83-7.08 (2H, m), 3.87-3.96 (2H, m), 3.81 (3H, s), 2.45-3.12 (6H, m), 2.05 (3H, s).

LCMS (B) RT 0.93, m/z [M+H]$^+$ 361.

(Step 2) N-(4-Methoxyphenyl)-2-methyl-5,6,7,8-tetrahydropyrido[3,4-d]pyrimidin-4-amine

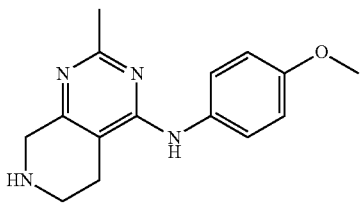 [SMILES: COc1ccc(Nc2nc(C)nc3c2CCNC3)cc1]

The compound (210 mg) obtained in step 1, 10% palladium/carbon (40 mg), and ammonium formate (184 mg) were suspended in methanol (6 mL), followed by stirring at 60° C. for 3 hours. The insolubles were removed by filtration through Celite, and the filtrate was concentrated under reduced pressure. Water was added to the residue, followed by extraction with a solvent mixture of chloroform and methanol three times. The collected organic layer was dried over sodium sulfate. The solvent was then distilled off under reduced pressure to obtain the target compound as a crude product of a light brown solid.

LCMS (B) RT 0.51, m/z[M+H]$^+$ 271.

Reference Example 15

N-(3-Fluoro-4-methoxyphenyl)-5,6,7,8-tetrahydropyrido[3,4-d]pyrimidin-4-amine

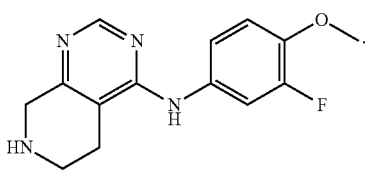 [SMILES: COc1ccc(Nc2ncnc3c2CCNC3)cc1F]

A crude product of the target compound was obtained by the same procedure as Reference Example 14 except that commercially available 7-benzyl-4-chloro-5,6,7,8-tetrahydropyrido[3,4-d]pyrimidine was used instead of 7-benzyl-4-chloro-2-methyl-5,6,7,8-tetrahydropyrido[3,4-d]pyrimidine and that 3-fluoro-4-methoxyaniline was used instead of 4-methoxyaniline.

LCMS (A) RT 0.82, m/z [M+H]$^+$ 275.

Production Example A

A starting compound (Ia)″ and amine (XI) were reacted according to the following reaction formula to produce a production compound (Ia)′ (Examples 1 to 11). As a typical procedure, the production procedure of Example 1 is shown below. The compounds of Examples 2 to 11 were each produced by the same procedure with the starting compound (Ia)″ and the amine (XI) changed as shown in Tables 1 and 2.

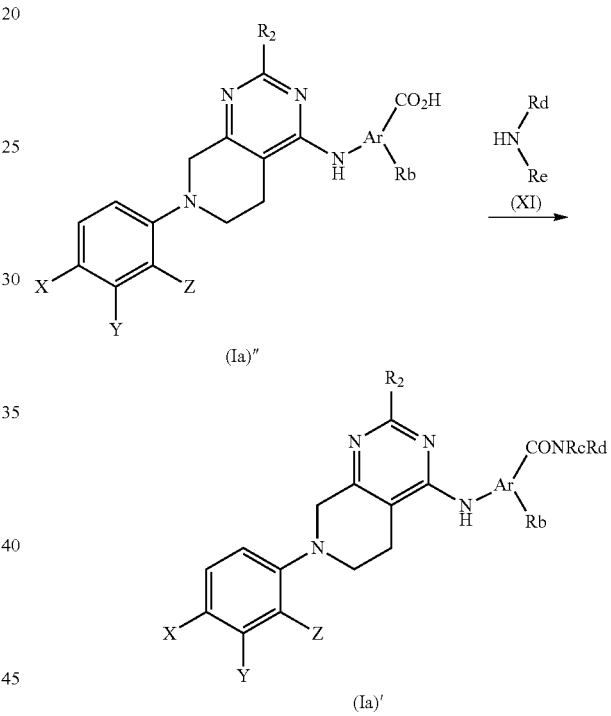

Example 1 6-((7-(3-Chloro-4-cyanophenyl)-5,6,7,8-tetrahydropyrido[3,4-d]pyrimidin-4-yl)amino)-N-ethyl-2-fluoronicotinamide

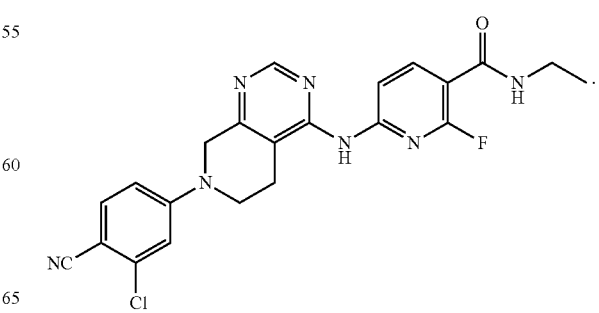

WSC.HCl (5.8 mg), HOBt (4.7 mg), and an ethylamine-THF solution (2 mol/L, 0.012 mL) were sequentially added to a DMA (0.5 mL) solution of 6-((7-(3-chloro-4-cyanophenyl)-5,6,7,8-tetrahydropyrido[3,4-d]pyrimidin-4-yl)amino)-2-fluoronicotinic acid (8.6 mg) obtained in Reference Example 5, and the reaction mixture was stirred at room temperature for 1.5 hours. The reaction mixture was purified by reversed-phase preparative HPLC column chromatography. The resulting fraction was concentrated under reduced pressure to obtain the target compound.

TABLE 1

| Example | (Ia)" | (XI) | Production Compound (Ia)' |
|---|---|---|---|
| 1 | Reference Example 5 | ethylamine | 6-((7-(3-chloro-4-cyanophenyl)-5,6,7,8-tetrahydropyrido[3,4-d]pyrimidin-4-yl)amino)-N-ethyl-2-fluoronicotinamide |
| 2 | Reference Example 5 | methylamine | 6-((7-(3-chloro-4-cyanophenyl)-5,6,7,8-tetrahydropyrido[3,4-d]pyrimidin-4-yl)amino)-2-fluoro-N-methylnicotinamide |
| 3 | Reference Example 6 | methylamine | 6-((7-(4-cyano-3-(trifluoromethyl)phenyl)-5,6,7,8-tetrahydropyrido[3,4-d]pyrimidin-4-yl)amino)-2-fluoro-N-methylnicotinamide |
| 4 | Reference Example 6 | ethylamine | 6-((7-(4-cyano-3-(trifluoromethyl)phenyl)-5,6,7,8-tetrahydropyrido[3,4-d]pyrimidin-4-yl)amino)-N-ethyl-2-fluoronicotinamide |
| 5 | Reference Example 7 | ethylamine | 6-((7-(4-cyano-3-(trifluoromethyl)phenyl)-5,6,7,8-tetrahydropyrido[3,4-d]pyrimidin-4-yl)amino)-N-ethylnicotinamide |
| 6 | Reference Example 7 | azepane (HN-cycloheptane) | 4-(4-((5-(azepane-1-carbonyl)pyridin-2-yl)amino)-5,6-dihydropyrido[3,4-d]pyrimidin-7(8H)-yl)-2-(trifluoromethyl)benzonitrile |

TABLE 2

| Example | (Ia)" | (VII) | Production Compound (Ia)' |
|---|---|---|---|
| 7 | Reference Example 7 | H$_2$N-O-tBu (O-tert-butylhydroxylamine) | N-(tert-butoxy)-6-((7-(4-cyano-3-(trifluoromethyl)phenyl)-5,6,7,8-tetrahydropyrido[3,4-d]pyrimidin-4-yl)amino)nicotinamide |
| 8 | Reference Example 7 | H$_2$N-CH$_2$CH$_2$-NHBoc | tert-butyl (2-(6-((7-(4-cyano-3-(trifluoromethyl)phenyl)-5,6,7,8-tetrahydropyrido[3,4-d]pyrimidin-4-yl)amino)pyridazine-3-carboxamido)ethyl)carbamate |
| 9 | Reference Example 8 | cyclopropylamine (H$_2$N-cyclopropyl) | 6-((7-(4-cyano-3-(trifluoromethyl)phenyl)-5,6,7,8-tetrahydropyrido[3,4-d]pyrimidin-4-yl)amino)-N-cyclopropylpyridazine-3-carboxamide |
| 10 | Reference Example 8 | ethylamine | 6-((7-(4-cyano-3-(trifluoromethyl)phenyl)-5,6,7,8-tetrahydropyrido[3,4-d]pyrimidin-4-yl)amino)-N-ethylpyridazine-3-carboxamide |
| 11 | Reference Example 8 | H$_2$N-CH$_2$-C≡CH (propargylamine) | 6-((7-(4-cyano-3-(trifluoromethyl)phenyl)-5,6,7,8-tetrahydropyrido[3,4-d]pyrimidin-4-yl)amino)-N-(prop-2-yn-1-yl)pyridazine-3-carboxamide |

Production Example B

Example 12 N-Ethyl-2-fluoro-6-((7-(4-nitro-3-(trifluoromethyl)phenyl)-5,6,7,8-tetrahydropyrido[3,4-d]pyrimidin-4-yl)amino)nicotinamide

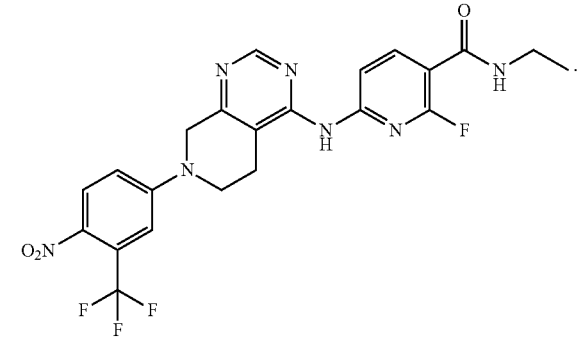 [SMILES: CCNC(=O)c1ccc(Nc2ncnc3c2CCN(c2ccc([N+](=O)[O-])c(C(F)(F)F)c2)C3)nc1F]

2-Fluoro-6-((7-(4-nitro-3-(trifluoromethyl)phenyl)-5,6,7,8-tetrahydropyrido[3,4-d]pyrimidin-4-yl)amino)nicotinic acid was obtained by the same procedure as Reference Example 5 except that the compound obtained in Reference Example 3 was used instead of the compound obtained in Reference Example 1 and that ethyl 6-amino-2-fluoronicotinate was used instead of methyl 6-aminonicotinate. The procedure as in Example 1 was further performed using the resulting product to obtain the target compound.

Production Example C

A starting compound (X) and a compound (IV) were reacted according to the following reaction formula to produce a production compound (Ia) (Examples 13 to 22). As a typical procedure, the production procedure of Example 13 is shown below. The compounds of Examples 14 to 22 were each produced by the same procedure with the starting compound (X) and the compound (IV) changed as shown in Tables 3 and 4.

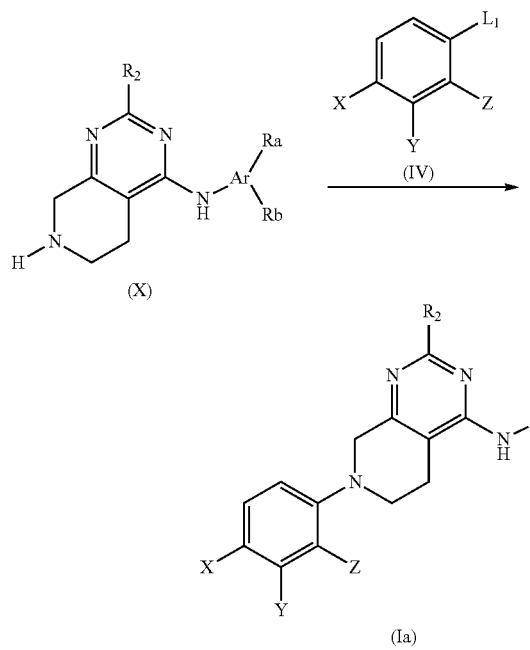

(X)

(Ia)

Example 13 2-(6-((7-(3-Chloro-4-nitrophenyl)-5,6,7,8-tetrahydropyrido[3,4-d]pyrimidin-4-yl)amino)pyridin-3-yl)propan-2-ol The compound (50 mg) obtained in Reference Example 4, 4-fluoro-1-nitro-2-chlorobenzene (37 mg), and potassium carbonate (97 mg) were suspended in DMSO (1.0 mL), and the reaction mixture was stirred at room temperature for 2 hours. Insolubles were removed from the reaction mixture by filtration, and the filtrate was then purified by reversed-phase preparative HPLC column chromatography. The resulting fraction was concentrated under reduced pressure to obtain the target compound.

TABLE 3

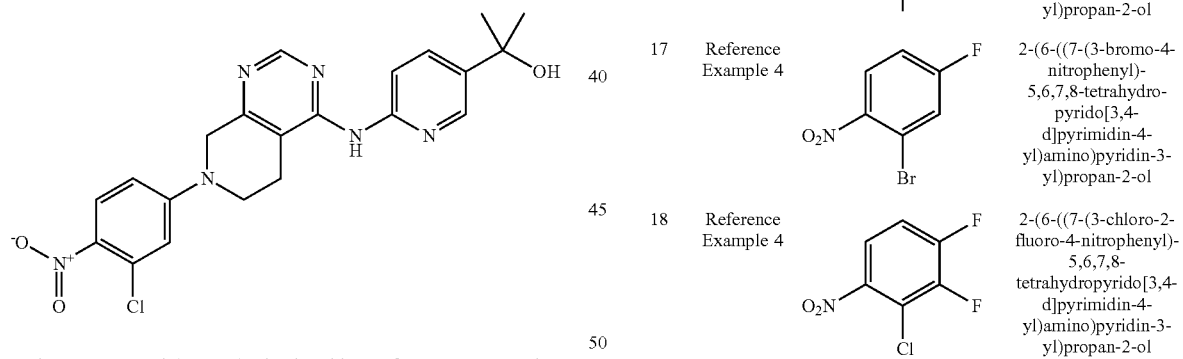

| Example | (X) | (IV) | Production Compound (Ia) |
|---|---|---|---|
| 13 | Reference Example 4 | | 2-(6-((7-(3-chloro-4-nitrophenyl)-5,6,7,8-tetrahydropyrido[3,4-d]pyrimidin-4-yl)amino)pyridin-3-yl)propan-2-ol |
| 14 | Reference Example 4 | | 2-(6-((7-(4-nitro-3-(trifluoromethyl)phenyl)-5,6,7,8-tetrahydropyrido[3,4-d]pyrimidin-4-yl)amino)pyridin-3-yl)propan-2-ol |
| 15 | Reference Example 4 | | 2-(6-((7-(3-methoxy-4-nitrophenyl)-5,6,7,8-tetrahydropyrido[3,4-d]pyrimidin-4-yl)amino)pyridin-3-yl)propan-2-ol |
| 16 | Reference Example 4 | | 2-(6-((7-(3-methyl-4-nitrophenyl)-5,6,7,8-tetrahydropyrido[3,4-d]pyrimidin-4-yl)amino)pyridin-3-yl)propan-2-ol |
| 17 | Reference Example 4 | | 2-(6-((7-(3-bromo-4-nitrophenyl)-5,6,7,8-tetrahydropyrido[3,4-d]pyrimidin-4-yl)amino)pyridin-3-yl)propan-2-ol |
| 18 | Reference Example 4 | | 2-(6-((7-(3-chloro-2-fluoro-4-nitrophenyl)-5,6,7,8-tetrahydropyrido[3,4-d]pyrimidin-4-yl)amino)pyridin-3-yl)propan-2-ol |

TABLE 4

| Example | (X) | (IV) | Production Compound (Ia) |
|---|---|---|---|
| 19 | Reference Example 4 | | 2-(6-((7-(3-isopropoxy-4-nitrophenyl)-5,6,7,8-tetrahydropyrido[3,4-d]pyrimidin-4-yl)amino)pyridin-3-yl)propan-2-ol |

TABLE 4-continued

| Example | (X) | (IV) | Production Compound (Ia) |
|---|---|---|---|
| 20 | Reference Example 4 | 4-fluoro-2-methylbenzonitrile (NC-phenyl-F with methyl) | 4-(4-((5-(2-hydroxypropan-2-yl)pyridin-2-yl)amino)-5,6-dihydropyrido[3,4-d]pyrimidin-7(8H)-yl)-2-methylbenzonitrile |
| 21 | Reference Example 15 | 4-fluoro-1-nitro-2-(trifluoromethyl)benzene (O$_2$N-phenyl-F with CF$_3$) | N-(3-fluoro-4-methoxyphenyl)-7-(4-nitro-3-(trifluoromethy))phenyl)-5,6,7,8-tetrahydropyrido[3,4-d]pyrimidin-4-amine |
| 22 | Reference Example 15 | 2-chloro-4-fluoro-1-nitrobenzene (O$_2$N-phenyl-F with Cl) | 7-(3-chloro-4-nitrophenyl)-N-(3-fluoro-4-methoxyphenyl)-5,6,7,8-tetrahydropyrido[3,4-d]pyrimidin-4-amine |

Production Example D

Example 23 4-(4-((5-(2-Hydroxypropan-2-yl)pyridin-2-yl)amino)-5,6-dihydropyrido[3,4-d]pyrimidin-7(8H)-yl)-2-methoxybenzonitrile 2-(6-((5,6,7,8-Tetrahydropyrido[3,4-d]pyrimidin-4-yl)amino)pyridin-3-yl)propan-2-ol (20 mg) obtained in Reference Example 4, 4-bromo-2-methoxybenzonitrile (22 mg), tris(dibenzylideneacetone)dipalladium (6.4 mg), Xantphos (8.1 mg), and sodium tert-butoxide (10 mg) were suspended in dioxane (0.4 mL), followed by stirring under microwave irradiation at 130° C. for 40 minutes. Insolubles were removed from the reaction mixture by filtration, and the resulting solution was purified by reversed-phase preparative HPLC column chromatography. The resulting fraction was concentrated under reduced pressure to obtain the target compound.

Production Example E

A starting compound (VI) and amine (VII) were reacted according to the following reaction formula to produce a production compound (Ia) (Examples 24 and 25). As a typical procedure, the production procedure of Example 24 is shown below. The compound of Example 25 was produced by the same procedure with the starting compound (VI) and the amine (VII) changed as shown in Table 5.

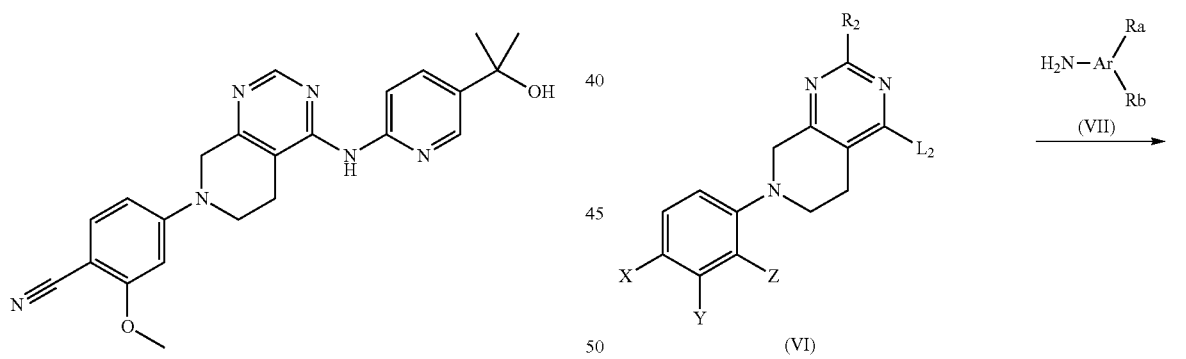

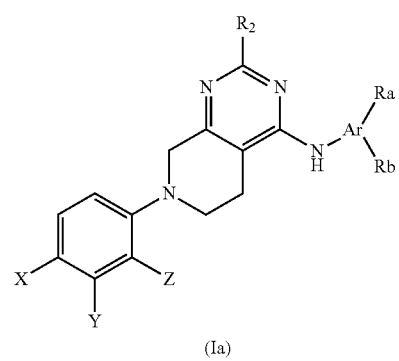

Example 24 6-((7-(4-Nitro-3-(trifluoromethyl)phenyl)-5,6,7,8-tetrahydropyrido[3,4-d]pyrimidin-4-yl)amino)-N-(2,2,2-trifluoroethyl)pyridazine-3-carboxamide

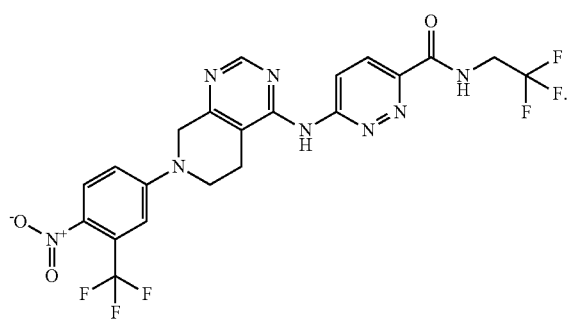

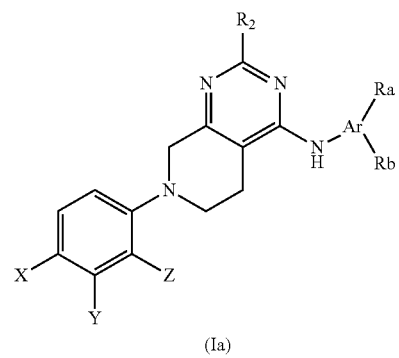
(Ia)

The compound (20 mg) obtained in Reference Example 3, commercially available 6-amino-N-(2,2,2-trifluoroethyl)pyrazine-3-carboxamide (15 mg), tris(dibenzylideneacetone)dipalladium (5.1 mg), dppf (6.2 mg), and cesium carbonate (55 mg) were suspended in dioxane (0.4 mL) and NMP (0.02 mL), followed by stirring under microwave irradiation at 140° C. for 45 minutes. Insolubles were removed from the reaction mixture by filtration, and the resulting solution was purified by reversed-phase preparative HPLC column chromatography. The resulting fraction was concentrated under reduced pressure to obtain the target compound.

TABLE 5

| Example | (VI) | (VII) | Production Compound (Ia) |
|---|---|---|---|
| 24 | Reference Example 3 | 6-amino-N-(2,2,2-trifluoroethyl)pyrazine-3-carboxamide | 6-((7-(4-nitro-3-(trifluoromethyl)phenyl)-5,6,7,8-tetrahydropyrido[3,4-d]pyrimidin-4-yl)amino)-N-(2,2,2-trifluoroethyl)pyridazine-3-carboxamide |
| 25 | Reference Example 3 | 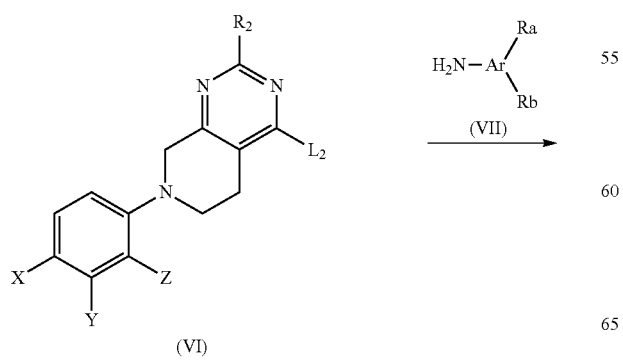 | N-(6-methoxypyridin-3-yl)-7-(4-nitro-3-(trifluoromethyl)phenyl)-5,6,7,8-tetrahydropyrido[3,4-d]pyrimidin-4-amine |

Production Example F

A starting compound (VI) and amine (VII) were reacted according to the following reaction formula to produce a production compound (Ia) (Examples 26 to 34). As a typical procedure, the production procedure of Example 26 is shown below. The compounds of Examples 27 to 34 were each produced by the same procedure with the starting compound (VI) and the amine (VII) changed as shown in Tables 6 and 7.

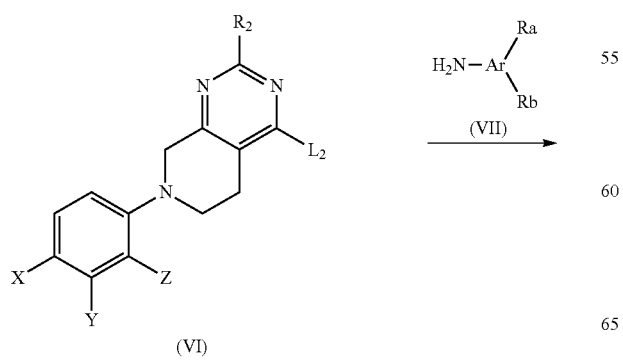

Example 26 4-(4-((3,4-Dimethoxyphenyl)amino)-5,6-dihydropyrido[3,4-d]pyrimidin-7(8H)-yl)-2-(trifluoromethyl)benzonitrile

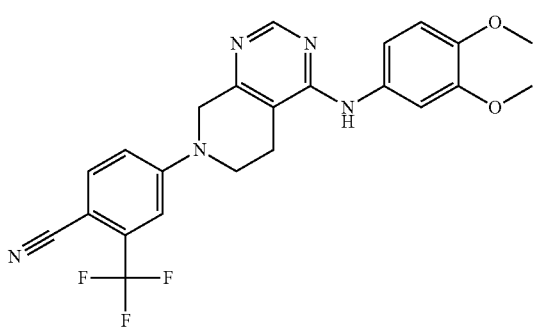 [SMILES: COc1ccc(Nc2ncnc3c2CCN(c2ccc(C#N)c(C(F)(F)F)c2)C3)cc1OC]

The solid (5.7 mg) obtained in Reference Example 1, 3,4-dimethoxyaniline (11.5 mg), and (+)-10-camphorsulfonic acid (5.6 mg) were suspended in tert-butanol (1 mL), followed by stirring under microwave irradiation at 140° C. for 45 minutes. The reaction mixture was concentrated and dried with a nitrogen flow, and the residue was then purified by reversed-phase preparative HPLC column chromatography. The resulting fraction was concentrated under reduced pressure to obtain the target compound.

TABLE 6

| Example | (VI) | (VII) | Production Compound (Ia) |
|---|---|---|---|
| 26 | Reference Example 1 | 3,4-dimethoxyaniline | 4-(4-((3,4-dimethoxyphenyl)amino)-5,6-dihydropyrido[3,4-d]pyrimidin-7(8H)-yl)-2-(trifluoromethyl)benzonitrile |
| 27 | Reference Example 1 | 4-(trifluoromethoxy)aniline | 4-(4-((4-(trifluoromethoxy)phenyl)amino)-5,6-dihydropyrido[3,4-d]pyrimidin-7(8H)-yl)-2-(trifluoromethyl)benzonitrile |
| 28 | Reference Example 2 | 4-(2-oxa-6-azaspiro[3.3]heptan-6-yl)aniline | 4-(4-((4-(2-oxa-6-azaspiro[3.3]heptan-6-yl)phenyl)amino)-5,6-dihydropyrido[3,4-d]pyrimidin-7(8H)-yl)-2-chlorobenzonitrile |
| 29 | Reference Example 2 | tert-butyl 5-aminoisoindoline-2-carboxylate | tert-butyl 5-((7-(3-chloro-4-cyanophenyl)-5,6,7,8-tetrahydropyrido[3,4-d]pyrimidin-4-yl)amino)isoindoline-2-carboxylate |
| 30 | Reference Example 3 | Reference Example 9 | tert-butyl 4-(3-(2-chloro-4-((7-(4-nitro-3-(trifluoromethyl)phenyl)-5,6,7,8-tetrahydropyrido[3,4-d]pyrimidin-4-yl)amino)phenoxy)propyl)piperazine-1-carboxylate |

TABLE 7

| Example | (VI) | (VII) | Production Compound (Ia) |
|---|---|---|---|
| 31 | Reference Example 3 | 3,4-dimethoxyaniline | N-(3,4-dimethoxyphenyl)-7-(4-nitro-3-(trifluoromethyl)phenyl)-5,6,7,8-tetrahydropyrido[3,4-d]pyrimidin-4-amine |
| 32 | Reference Example 3 | tert-butyl 7-amino-3,4-dihydroisoquinoline-2(1H)-carboxylate | tert-butyl 7-((7-(4-nitro-3-(trifluoromethyl)phenyl)-5,6,7,8-tetrahydropyrido[3,4-d]pyrimidin-4-yl)amino)-3,4-dihydroisoquinoline-2(1H)-carboxylate |
| 33 | Reference Example 3 | 3-methyl-4-(2-oxa-6-azaspiro[3.3]heptan-6-yl)aniline | N-(3-methyl-4-(2-oxa-6-azaspiro[3.3]heptan-6-yl)phenyl)-7-(4-nitro-3-(trifluoromethyl)phenyl)-5,6,7,8-tetrahydropyrido[3,4-d]pyrimidin-4-amine |
| 34 | Reference Example 3 | [1,1'-biphenyl]-3-amine | N-([1,1'-biphenyl]-3-yl)-7-(4-nitro-3-(trifluoromethyl)phenyl)-5,6,7,8-tetrahydropyrido[3,4-d]pyrimidin-4-amine |

Production Example G

Example 35 2-Chloro-4-(4-((6-fluoro-5-(3-hydroxyoxetan-3-yl)pyridin-2-yl)amino)-5,6-dihydropyrido[3,4-d]pyrimidin-7(8H)-yl)benzonitrile

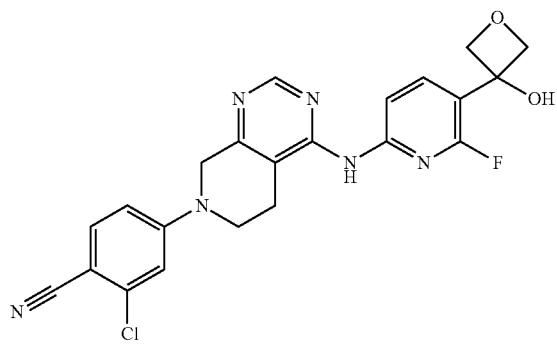 [SMILES: N#Cc1ccc(N2CCc3c(ncnc3Nc3ccc(C4(O)COC4)c(F)n3)C2)cc1Cl]

(Step 1) 3-(2,6-Difluoropyridin-3-yl)oxetan-3-ol

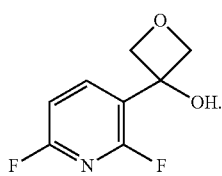

A THF (15 mL) solution of 2,6-difluoropyridine (825 mg) was cooled to −78° C., and LDA (2.0 mol/L, 5.2 mL) was dropwise added thereto. The reaction mixture was stirred for 45 minutes, and oxetan-3-one (580 mg) was then added thereto, followed by stirring at −78° C. for 90 minutes. The reaction mixture was diluted with ethyl acetate and was washed with a saturated ammonium chloride aqueous solution and saturated brine, then dried over sodium sulfate, and then concentrated to obtain the target compound as a brown oily material.

(Step 2) 3-(6-Amino-2-fluoropyridin-3-yl)oxetan-3-ol

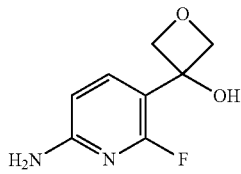

A 28% ammonia aqueous solution was added to an NMP (0.5 mL) solution of the compound (17 mg) obtained in step 1 at room temperature, and the reaction mixture was stirred at 90° C. overnight. The solvent was distilled off with a nitrogen flow, and the residue was then purified by silica gel chromatography (eluent: hexane-ethyl acetate) to obtain the target compound.

(Step 3) 2-Chloro-4-(4-((6-fluoro-5-(3-hydroxyoxetan-3-yl)pyridin-2-yl)amino)-5,6-dihydropyrido[3,4-d]pyrimidin-7(8H)-yl)benzonitrile

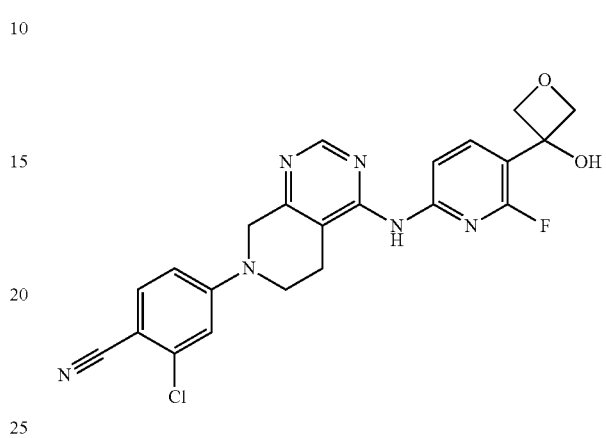

The compound (2.8 mg) obtained in step 2, the compound obtained in Reference Example 2, tris(dibenzylideneacetone)dipalladium (2.7 mg), Xantphos (3.7 mg), and sodium tert-butoxide (10 mg) were suspended in DME (1 mL), followed by stirring under microwave irradiation at 100° C. for 60 minutes. The solvent was distilled off with a nitrogen flow, and the residue was then purified by reversed-phase preparative HPLC column chromatography. The resulting fraction was concentrated under reduced pressure to obtain the target compound.

Production Example H

A starting compound (VI) and amine (VII) were reacted according to the following reaction formula to produce a production compound (Ia) (Examples 36 to 38). As a typical procedure, the production procedure of Examples 36 and 37 is shown below. The compound of Example 38 was produced by the same procedure with the starting compound (VI) and the amine (VII) changed as shown in Table 8.

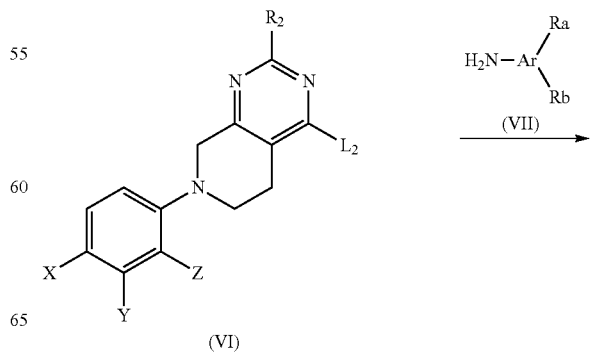

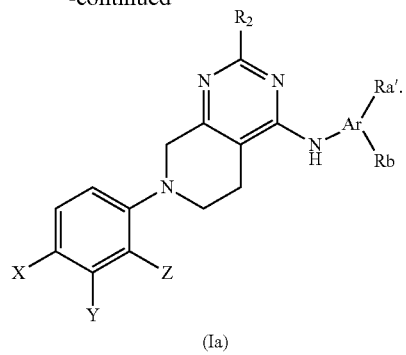

(Ia)

Example 36 tert-Butyl 7-((7-(3-chloro-4-cyanophenyl)-5,6,7,8-tetrahydropyrido[3,4-d]pyrimidin-4-yl)amino)-3,4-dihydroisoquinoline-2(1H)-carboxylate, and Example 37 2-Chloro-4-(4-((1,2,3,4-tetrahydroisoquinolin-7-yl)amino)-5,6-dihydropyrido[3,4-d]pyrimidin-7(8H)-yl)benzonitrile

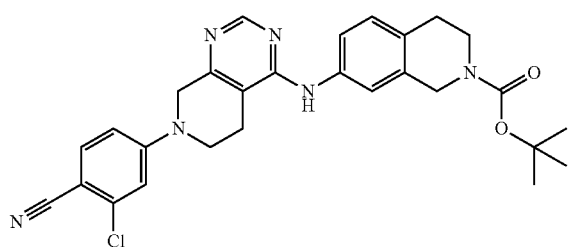

Example 36

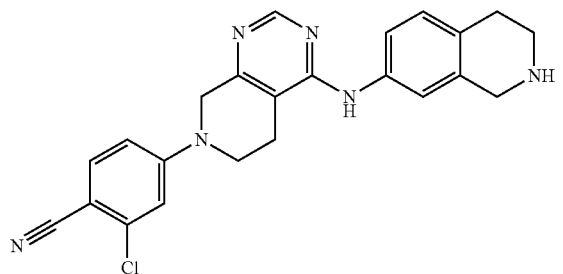

Example 37

The compound (7.4 mg) obtained in Reference Example 2,7-amino-3,4-dihydro-1H-isoquinoline-2-carboxylic acid tert-butyl ester (9.3 mg), and (+)-10-camphorsulfonic acid (2.5 mg) were suspended in tert-butanol (1 mL), followed by stirring under microwave irradiation at 140° C. for 15 minutes. The reaction mixture was concentrated and dried with a nitrogen flow, and the residue was then purified by reversed-phase preparative HPLC column chromatography. The resulting fraction was concentrated under reduced pressure to obtain the target compound.

TABLE 8

| Example | (VI) | (VII) | Production Compound (Ia) |
|---|---|---|---|
| 36 | Reference Example 2 | 7-amino-3,4-dihydro-1H-isoquinoline-2-carboxylic acid tert-butyl ester | tert-butyl 7-((7-(3-chloro-4-cyanophenyl)-5,6,7,8-tetrahydropyrido[3,4-d]pyrimidin-4-yl)amino)-3,4-dihydroisoquinoline-2(1H)-carboxylate |
| 37 | Reference Example 2 | 7-amino-3,4-dihydro-1H-isoquinoline-2-carboxylic acid tert-butyl ester | 2-chloro-4-(4-((1,2,3,4-tetrahydroisoquinolin-7-yl)amino)-5,6-dihydropyrido[3,4-d]pyrimidin-7(8H)-yl)benzonitrile |
| 38 | Reference Example 2 | Reference Example 11 | 2-chloro-4-(4-((4-(3-(piperazin-1-yl)propoxy)-3-(trifluoromethyl)phenyl)amino)-5,6-dihydropyrido[3,4-d]pyrimidin-7(8H)-yl)benzonitrile |

Production Example I

Examples 39, 40, and 41

(Step 1) N-[3-Chloro-4-(3-piperazin-1-ylpropoxy)phenyl]-7-[4-nitro-3-(trifluoromethyl)phenyl]-6,8-dihydro-5H-pyrido[3,4-d]pyrimidin-4-amine

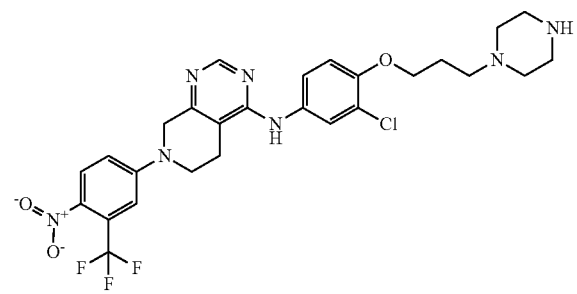

The compound (24 mg) obtained in Reference Example 9, the compound obtained in Reference Example 3, and (+)-10-camphorsulfonic acid (26 mg) were suspended in tert-butanol (2 mL), followed by stirring under microwave irradiation at 135° C. for 1 hour. The solvent was distilled off with a nitrogen flow, and the residue was used in the subsequent reaction as a crude product. [M+H]$^+$ 591/594.

Step 2A 1-(4-(3-(2-Chloro-4-((7-(4-nitro-3-(trifluoromethyl)phenyl)-5,6,7,8-tetrahydropyrido[3,4-d]pyrimidin-4-yl)amino)phenoxy)propyl)piperazin-1-yl)ethanone (Example 39)

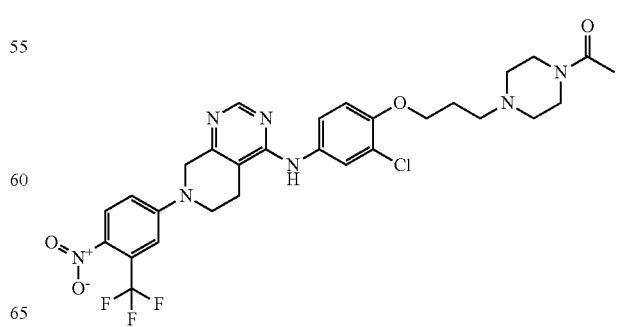

The crude product obtained in step 1 was equally divided into 5 fractions, and one of the fractions was dissolved in pyridine (0.2 mL). Acetic anhydride (0.01 mL) was added to the solution at room temperature, and the reaction mixture was stirred at room temperature for 15 minutes. The reaction mixture was concentrated and dried with a nitrogen flow, and the residue was then purified by reversed-phase preparative HPLC column chromatography. The resulting fraction was concentrated under reduced pressure to obtain the target compound.

Step 2B

N-(3-Chloro-4-(3-(4-(methylsulfonyl)piperazin-1-yl)propoxy)phenyl)-7-(4-nitro-3-(trifluoromethyl)phenyl)-5,6,7,8-tetrahydropyrido[3,4-d]pyrimidin-4-amine (Example 40)

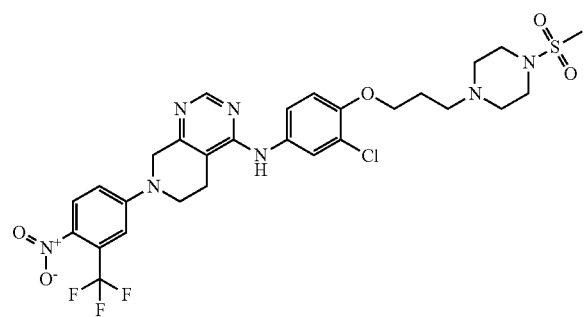 [SMILES: CS(=O)(=O)N1CCN(CCCOc2ccc(Nc3ncnc4c3CCN(c3ccc([N+](=O)[O-])c(C(F)(F)F)c3)C4)cc2Cl)CC1]

One of the fractions prepared in step 2 was dissolved in pyridine (0.2 mL). Methanesulfonyl chloride (0.01 mL) was added to the solution at room temperature, and the reaction mixture was stirred at room temperature for 15 minutes. The reaction mixture was concentrated and dried with a nitrogen flow, and the residue was purified by reversed-phase preparative HPLC column chromatography. The resulting fraction was concentrated under reduced pressure to obtain the target compound.

Step 2C

N-(3-Chloro-4-(3-(4-methylpiperazin-1-yl)propoxy)phenyl)-7-(4-nitro-3-(trifluoromethyl)phenyl)-5,6,7,8-tetrahydropyrido[3,4-d]pyrimidin-4-amine (Example 41)

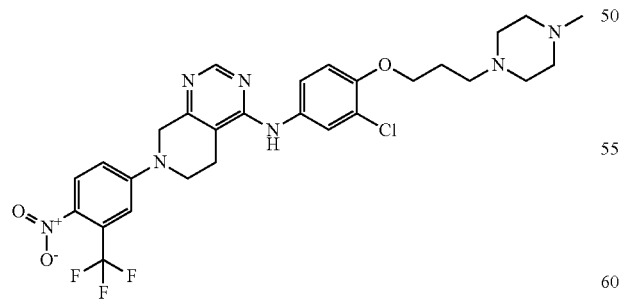

Zn(BH₃CN)₂ (0.3 mol/L methanol solution, 0.3 mL) separately prepared and a 50% formaldehyde aqueous solution (0.05 mL) were added to one of the fractions prepared in step 2, and the reaction mixture was stirred at room temperature for 15 minutes. The reaction mixture was concentrated and dried with a nitrogen flow, and the residue was then purified by reversed-phase preparative HPLC column chromatography. The resulting fraction was concentrated under reduced pressure to obtain the target compound.

Production Example J

A starting compound (VI) and amine (VII) were reacted according to the following reaction formula to produce a production compound (Ia) (Examples 42 to 46). As a typical procedure, the production procedure of Example 42 is shown below. The compounds of Examples 43 to 46 were each produced by the same procedure with the starting compound (VI) and the amine (VII) changed as shown in Table 9.

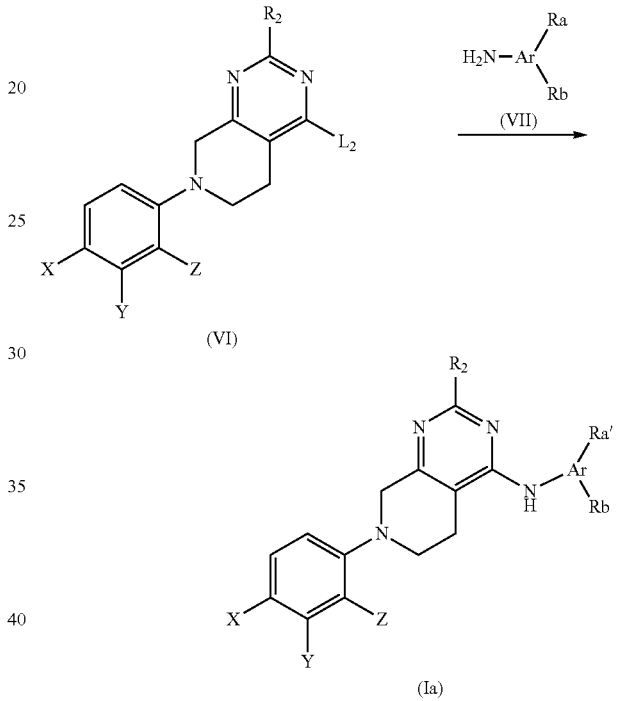

Example 42 4-(4-((4-(3-(4-Acetylpiperazin-1-yl)propoxy)-3-chlorophenyl)amino)-5,6-dihydropyrido[3,4-d]pyrimidin-7(8H)-yl)-2-chlorobenzonitrile

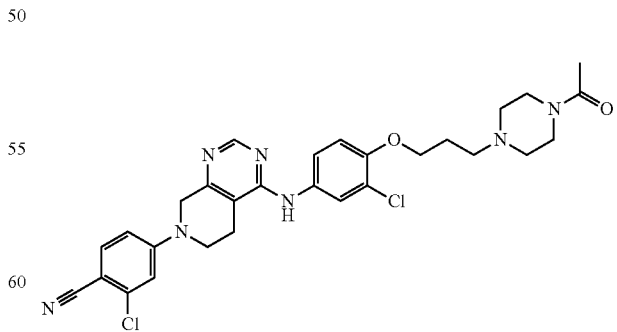

The compound (2.9 mg) obtained in Reference Example 2, the compound (4.4 mg) obtained in Reference Example 9, and (+)-10-camphorsulfonic acid (4.2 mg) were suspended in tert-butanol (1 mL), and the reaction mixture was stirred at 135° C. for 2 hours. The reaction mixture was concentrated and dried with a nitrogen flow. Pyridine (0.2 mL) and acetic anhydride (0.1 mL) were added to the residue at room temperature, and the reaction mixture was stirred at room temperature for 15 minutes. The reaction mixture was concentrated and dried with a nitrogen flow, and the residue was purified by reversed-phase preparative HPLC column chromatography. The resulting fraction was concentrated under reduced pressure to obtain the target compound as a yellow amorphous product.

TABLE 9

| Example | (VI) | (VII) | Production Compound (Ia) |
|---|---|---|---|
| 42 | Reference Example 2 | Reference Example 9 | 4-(4-((4-(3-(4-acetylpiperazin-1-yl)propoxy)-3-chlorophenyl)amino)-5,6-dihydropyrido[3,4-d]pyrimidin-7(8H)-yl)-2-chlorobenzonitrile |
| 43 | Reference Example 2 | Reference Example 11 | 4-(4-((4-(3-(4-acetylpiperazin-1-yl)propoxy)-3-(trifluoromethyl)phenyl)amino)-5,6-dihydropyrido[3,4-d]pyrimidin-7(8H)-yl)-2-chlorobenzonitrile |
| 44 | Reference Example 1 | Reference Example 12 | 4-(4-((4-(3-(4-acetylpiperazin-1-yl)propoxy)-2-(trifluoromethyl)phenyl)amino)-5,6-dihydropyrido[3,4-d]pyrimidin-7(8H)-yl)-2-(trifluoromethyl)benzonitrile |
| 45 | Reference Example 3 | Reference Example 11 | 1-(4-(3-(4-((7-(4-nitro-3-(trifluoromethyl)phenyl)-5,6,7,8-tetrahydropyrido[3,4-d]pyrimidin-4-yl)amino)-2-(trifluoromethyl)phenoxy)propyl)piperazin-1-yl)ethanone |
| 46 | Reference Example 3 | Reference Example 10 | 1-(4-(3-(4-((7-(4-nitro-3-(trifluoromethyl)phenyl)-5,6,7,8-tetrahydropyrido[3,4-d]pyrimidin-4-yl)amino)phenoxy)propyl)piperazin-1-yl)ethanone |

Production Example K

Example 47 7-(4-Cyano-3-(trifluoromethyl)phenyl)-4-((4-methoxyphenyl)amino)-5,6,7,8-tetrahydropyrido[3,4-d]pyrimidine-2-carbonitrile

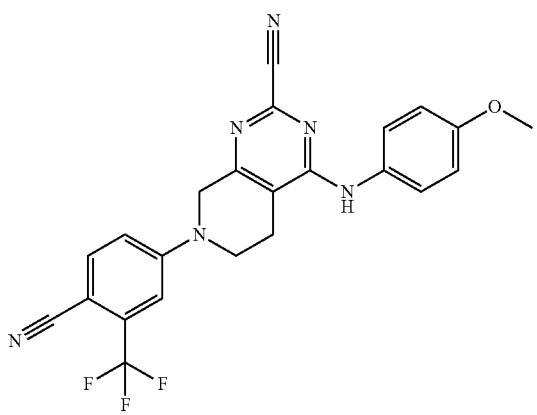 [SMILES: COc1ccc(Nc2nc(C#N)nc3c2CCN(c2ccc(C#N)c(C(F)(F)F)c2)C3)cc1]

(Step 1) 4-(4-((4-Methoxyphenyl)amino)-2-(methylthio)-5,6-dihydropyrido[3,4-d]pyrimidin-7(8H)-yl)-2-(trifluoromethyl)benzonitrile

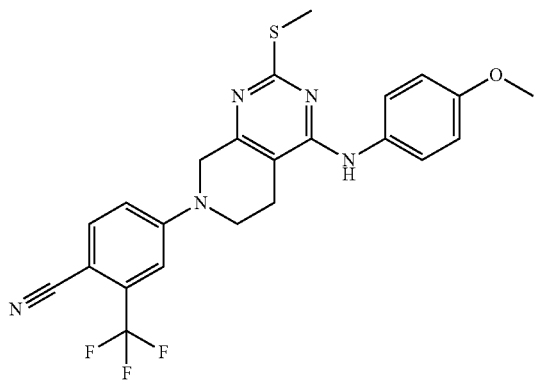 [SMILES: COc1ccc(Nc2nc(SC)nc3c2CCN(c2ccc(C#N)c(C(F)(F)F)c2)C3)cc1]

The target compound was obtained as a light brown solid by the same procedure as Example 13 except that the compound (656 mg) obtained in step 2 of Reference Example 13 was used instead of 2-(6-((5,6,7,8-tetrahydropyrido[3,4-d]pyrimidin-4-yl)amino)pyridin-3-yl)propan-2-ol and that 4-fluoro-1-cyano-(2-trifluoromethyl)benzene (403 mg) was used instead of 4-fluoro-1-nitro-2-chlorobenzene.

(Step 2) 4-(4-((4-Methoxyphenyl)amino)-2-(methylsulfonyl)-5,6-dihydropyrido[3,4-d]pyrimidin-7(8H)-yl)-2-(trifluoromethyl)benzonitrile

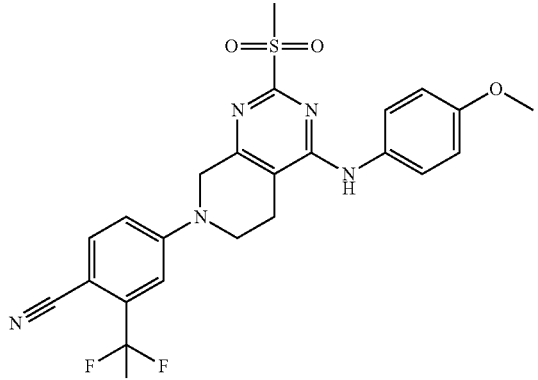

mCPBA (157 mg) was added to a chloroform (4 mL) solution of the compound (157 mg) obtained in step 1 at room temperature, and the reaction mixture was stirred at room temperature for 30 minutes. A saturated sodium hydrogen sulfite aqueous solution and a saturated sodium hydrogen carbonate aqueous solution were added to the reaction mixture, followed by extraction with a chloroform/methanol solvent mixture. The collected organic layer was dried over sodium sulfate and was then concentrated under reduced pressure to obtain the target compound as a light yellow solid.

(Step 3) 7-(4-Cyano-3-(trifluoromethyl)phenyl)-4-((4-methoxyphenyl)amino)-5,6,78-tetrahydropyrido[3,4-d]pyrimidine-2-carbonitrile

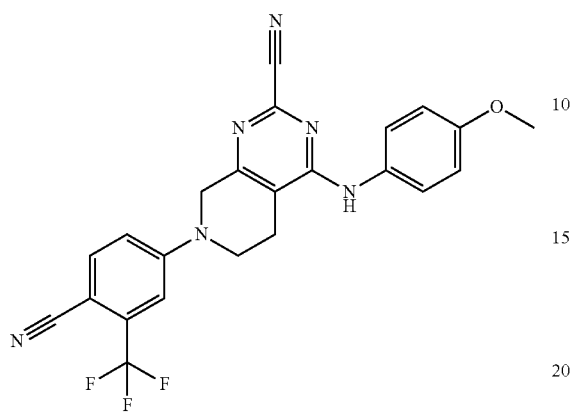

Sodium cyanide (9 mg) was added to a DMSO (1.5 mL) solution of the compound (44 mg) obtained in step 2 at room temperature, and the reaction mixture was stirred at 150° C. for 15 minutes. The reaction mixture was diluted with ethyl acetate, washed with water and saturated brine, then dried over sodium sulfate, and then concentrated. The resulting residue was purified by silica gel column chromatography to obtain the target compound.

Example 48 4-(4-((4-Methoxyphenyl)amino)-2-methyl-5,6-dihydropyrido[3,4-d]pyrimidin-7(8H)-yl)-2-(trifluoromethyl)benzonitrile

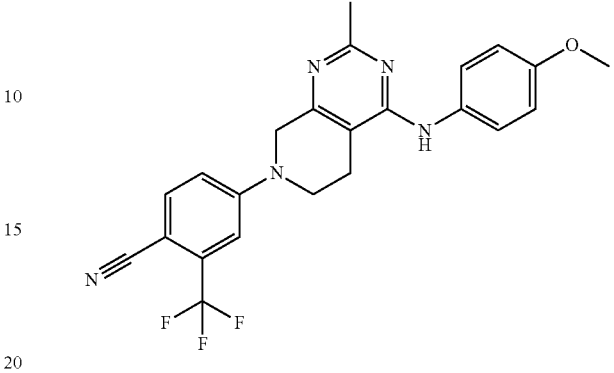

The target compound was obtained by the same procedure as Example 47 except that the compound (117 mg) obtained in step 2 of Reference Example 14 was used instead of 2-(6-((5,6,7,8-tetrahydropyrido[3,4-d]pyrimidin-4-yl)amino)pyridin-3-yl)propan-2-ol and that 4-fluoro-1-cyano-(2-trifluoromethyl)benzene (90 mg) was used instead of 4-fluoro-1-nitro-2-chlorobenzene.

Tables 10 to 22 show the structural formulae and physical property values obtained by LC/MS analysis of the compounds of Examples 1 to 48.

TABLE 10

| Example | Structural formula | Physical property value |
|---|---|---|
| 1 |  | $^1$H-NMR (CDCl$_3$) δ: 8.76 (1H, s), 8.61 (1H, d, J = 2.6 Hz), 8.60 (1H, s), 7.53 (1H, d, J = 8.8 Hz), 7.00 (1H, d, J = 2.6 Hz), 6.85 (1H, dd, J = 8.8, 2.6 Hz), 6.69 (1H, br-s), 4.49 (2H, s), 3.82 (2H, t, J = 5.7 Hz), 3.56-3.50 (2H, m), 2.84 (2H, t, J = 5.7 Hz), 1.28 (3H, t, J = 7.1 Hz). LC/MS (A) RT 1.7 min; m/z [M + H]$^+$ 452/454. |
| 2 |  | $^1$H-NMR (CDCl$_3$) δ: 8.76 (1H, s), 8.62 (1H, d, J = 4.0 Hz), 8.61 (1H, s), 7.53 (1H, d, J = 8.8 Hz), 7.00 (1H, d, J = 2.2 Hz), 6.85 (1H, dd, J = 9.0, 2.4 Hz), 6.71 (1H, br-s), 4.49 (2H, s), 3.82 (2H, t, J = 5.7 Hz), 3.05 (3H, d, J = 4.4 Hz), 2.83 (2H, t, J = 5.9 Hz). LC/MS (A) RT 1.59 min; m/z [M + H]$^+$ 438/440. |

TABLE 10-continued

| Example | Structural formula | Physical property value |
|---|---|---|
| 3 | | ¹H-NMR (CDCl₃) δ: 8.77 (1H, s), 8.63 (1H, d, J = 5.1 Hz), 8.61 (1H, s), 7.71 (1H, d, J = 8.8 Hz), 7.25 (1H, d, J = 2.6 Hz), 7.08 (1H, dd, J = 8.8, 2.6 Hz), 6.71 (1H, br-s), 4.55 (2H, s), 3.88 (2H, t, J = 5.7 Hz), 3.05 (3H, d, J = 4.4 Hz), 2.86 (2H, t, J = 5.7 Hz). LC/MS (A) RT 1.68 min; m/z [M + H]⁺ 472. |
| 4 | | ¹H-NMR (CDCl₃) δ: 8.77 (1H, s), 8.62 (1H, d, J = 3.7 Hz), 8.61 (1H, s), 7.70 (1H, d, J = 8.4 Hz), 7.24 (1H, d, J = 2.2 Hz), 7.08 (1H, dd, J = 8.6, 2.7 Hz), 6.68 (1H, br-s), 4.55 (2H, s), 3.88 (2H, t, J = 5.7 Hz), 3.55-3.51 (2H, m), 2.88-2.85 (2H, m), 1.28 (3H, t, J = 7.3 Hz). LC/MS (A) RT 1.77 min; m/z [M + H]⁺ 486. |

TABLE 11

| Example | Structural formula | Physical property value |
|---|---|---|
| 5 | | ¹H-NMR (DMSO-d6) δ: 1.10 (3H, br-t, J = 7.3 Hz), 2.84-2.94 (2H, m), 3.18-3.40 (2H, m), 3.77-3.89 (2H, m), 4.55 (2H, s), 7.35 (1H, br-d, J = 8.9 Hz), 7.41 (1H, br-s), 7.84 (1H, br-d, J = 8.9 Hz), 8.15 (1H, d, J = 8.9 Hz), 8.19 (1H, d, J = 8.9 Hz), 8.48 (1H, br-t, J = 5.1 Hz), 8.60 (1H, s), 8.75 (1H, br-s), 9.40 (1H, br-s). LC/MS (A) RT 1.47 min; m/z [M + H]⁺ 468. |
| 6 | | ¹H-NMR (DMSO-d6) δ: 1.42-1.76 (8H, m), 2.83-2.94 (2H, m), 3.34-3.44 (2H, m), 3.48-3.58 (2H, m), 3.79-3.89 (2H, m), 4.54 (2H, s), 7.35 (1H, br-d, J = 8.9 Hz), 7.41 (1H, s), 7.79 (1H, br-d, J = 8.9 Hz), 7.84 (1H, br-d, J = 8.9 Hz), 8.16 (1H, br-d, J = 8.9 Hz), 8.33 (1H, s), 8.58 (1H, s), 9.30 (1H, s). LC/MS (A) RT 1.7 min; m/z [M + H]⁺ 522. |

TABLE 11-continued

| Example | Structural formula | Physical property value |
|---|---|---|
| 7 | | ¹H-NMR (DMSO-d6) δ: 1.21 (6H, s), 2.84-2.93 (2H, m), 3.78-3.89 (2H, m), 4.55 (2H, s), 7.35 (1H, br-d, J = 8.9 Hz), 7.41 (1H, br-s), 7.84 (1H, br-d, J = 8.9 Hz), 8.09 (1H, br-d, J = 8.2 Hz), 8.17 (1H, br-d, J = 8.9 Hz), 8.60 (1H, s), 8.67 (1H, br-s), 9.44 (1H, br-s), 10.97 (2H, br-s). LC/MS (A) RT 1.6 min; m/z [M + H]⁺ 512. |
| 8 | | ¹H-NMR (CDCl₃) δ: 9.00 (1H, d, J = 8.8 Hz), 8.75 (1H, s), 8.32 (1H, d, J = 9.2 Hz), 8.27 (1H, s), 7.95 (1H, s), 7.71 (1H, d, J = 8.8 Hz), 7.09 (1H, d, J = 8.4 Hz), 4.93 (1H, br-s), 4.57 (2H, s), 3.91 (2H, t, J = 5.3 Hz), 3.65 (2H, q, J = 5.7 Hz), 3.42 (2H, q, J = 5.9 Hz), 2.99-2.96 (2H, m), 1.58 (9H, s). LC/MS (A) RT 1.83 min; m/z [M + H]⁺ 584. |

TABLE 12

| Example | Structural formula | Physical property value |
|---|---|---|
| 9 | | ¹H-NMR (DMSO-d6) δ: 0.62-0.72 (2H, m), 1.56-3.56 (5H, m), 3.79-3.92 (2H, m), 4.58 (2H, br-s), 7.35 (1H, br-d, J = 8.9 Hz), 7.40-7.45 (1H, m), 7.84 (1H, br-d, J = 8.9 Hz), 8.09 (1H, br-d, J = 8.9 Hz), 8.38 (1H, br-d, J = 8.9 Hz), 8.60 (1H, br-s), 8.92 (1H, br-d, J = 4.4 Hz), 10.02-10.15 (1H, br-s). LC/MS (A) RT 1.61 min; m/z [M + H]⁺ 481. |
| 10 | | ¹H-NMR (DMSO-d6) δ: 1.12 (2H, br-t, J = 7.0 Hz), 2.90-3.01 (2H, m), 3.31 (s H, m), 3.79-3.88 (2H, m), 4.59 (2H, s), 7.36 (1H, br-d, J = 8.9 Hz), 7.42 (1H, br-s), 7.84 (1H, br-d, J = 8.9 Hz), 8.10 (1H, br-d, J = 9.5 Hz), 8.41 (1H, br-d, J = 9.5 Hz), 8.61 (1H, s), 8.93-9.03 (1H, m), 10.15 (2H, br-s). LC/MS (A) RT 1.6 min; m/z [M + H]⁺ 469. |

TABLE 12-continued

| Example | Structural formula | Physical property value |
|---|---|---|
| 11 | | ¹H-NMR (CDCl₃) δ: 9.02 (1H, d, J = 9.2 Hz), 8.75 (1H, s), 8.33 (1H, d, J = 9.2 Hz), 8.13 (1H, t, J = 5.5 Hz), 8.07 (1H, br-s), 7.71 (1H, d, J = 8.8 Hz), 7.25 (1H, s), 7.10 (1H, dd, J = 8.8, 2.6 Hz), 4.57 (2H, s), 4.33 (2H, dd, J = 5.5, 2.6 Hz), 3.91 (2H, t, J = 5.7 Hz), 2.98 (2H, t, J = 5.5 Hz), 2.31 (1H, t, J = 2.6 Hz). LC/MS (A) RT 1.73 min; m/z [M + H]⁺ 479. |
| 12 | | ¹H-NMR (CDCl₃) δ: 8.78 (1H, s), 8.62 (1H, d, J = 3.7 Hz), 8.61 (1H, s), 8.09 (1H, d, J = 9.2 Hz), 7.32 (1H, s), 7.27 (1H, d, J = 3.3 Hz), 7.07 (1H, dd, J = 9.2, 2.9 Hz), 6.70-6.68 (1H, m), 4.58 (2H, s), 3.91 (2H, t, J = 5.7 Hz), 3.57-3.50 (2H, m), 2.88 (2H, t, J = 5.7 Hz), 1.28 (3H, t, J = 7.3 Hz). LC/MS (A) RT 1.71 min; m/z [M + H]⁺ 506. |

TABLE 13

| Example | Structural formula | Physical property value |
|---|---|---|
| 13 | | ¹H-NMR (CDCl₃) δ: 8.68 (1H, s), 8.48 (1H, d, J = 8.8 Hz), 8.35 (1H, d, J = 2.2 Hz), 8.20 (1H, s), 8.08 (1H, d, J = 9.2 Hz), 7.93 (1H, dd, J = 8.8, 2.2 Hz), 6.98 (1H, d, J = 2.6 Hz), 6.84 (1H, dd, J = 9.5, 2.6 Hz), 4.52 (2H, s), 3.85 (2H, t, J = 5.9 Hz), 2.94 (2H, t, J = 5.7 Hz), 1.63 (6H, s). LC/MS (A) RT 1.41 min; m/z [M + H]⁺ 441/443. |
| 14 | | ¹H-NMR (CDCl₃) δ: 8.68 (1H, s), 8.48 (1H, d, J = 8.8 Hz), 8.33 (1H, d, J = 2.6 Hz), 8.21 (1H, s), 8.09 (1H, d, J = 9.2 Hz), 7.96 (1H, dd, J = 9.0, 2.4 Hz), 7.27 (1H, d, J = 2.6 Hz), 7.06 (1H, dd, J = 9.2, 2.9 Hz), 4.57 (2H, s), 3.89 (2H, t, J = 5.7 Hz), 2.99 (2H, t, J = 5.7 Hz), 1.63 (6H, s). LC/MS (A) RT 1.5 min; m/z [M + H]⁺ 475. |

TABLE 13-continued

| Example | Structural formula | Physical property value |
| --- | --- | --- |
| 15 | | $^1$H-NMR (CDCl$_3$) δ: 8.68 (1H, s), 8.48 (1H, d, J = 9.2 Hz), 8.43 (1H, d, J = 2.6 Hz), 8.06 (1H, d, J = 9.2 Hz), 7.87 (1H, dd, J = 8.8, 2.6 Hz), 6.55 (1H, dd, J = 9.5, 2.6 Hz), 6.42 (1H, d, J = 2.6 Hz), 4.53 (2H, s), 3.99 (3H, s), 3.86 (2H, t, J = 5.7 Hz), 2.85 (2H, t, J = 5.7 Hz), 1.25 (6H, s). LC/MS (A) RT 1.24 min; m/z [M + H]$^+$ 437. |
| 16 | | $^1$H-NMR (DMSO-d6) δ: 9.05 (1H, s), 8.54 (1H, s), 8.42 (1H, d, J = 2.2 Hz), 8.04 (1H, d, J = 2.6 Hz), 8.02 (1H, d, J = 2.9 Hz), 7.83 (1H, dd, J = 8.8, 2.6 Hz), 7.05-7.02 (2H, m), 5.15 (1H, br-s), 4.52 (2H, s), 3.84 (2H, t, J = 5.7 Hz), 2.87 (2H, t, J = 5.5 Hz), 2.59 (3H, s), 1.46 (6H, s). LC/MS (A) RT 1.32 min; m/z [M + H]$^+$ 421. |

TABLE 14

| Example | Structural formula | Physical property value |
| --- | --- | --- |
| 17 | | $^1$H-NMR (CDCl$_3$) δ: 1.60 (6H, s), 2.88 (2H, m), 3.86 (2H, d, J = 5.5 Hz), 4.50 (2H, s), 6.92 (1H, dd, J = 9.2, 2.9 Hz), 7.23 (1H, d, J = 2.9 Hz), 7.89 (1H, dd, J = 8.8, 2.4 Hz), 8.07 (1H, d, J = 9.2 Hz), 8.11 (1H, br-s), 8.40 (1H, d, J = 2.4 Hz), 8.46 (1H, d, J = 8.8 Hz), 8.64 (1H, s). LC/MS (A) RT 1.44 min; m/z [M + H]$^+$ 485/487. |
| 18 | | $^1$H-NMR (CDCl$_3$) δ: 1.63 (6H, s), 2.93 (2H, t, J = 5.5 Hz), 3.76 (2H, t, J = 5.5 Hz), 4.44 (2H, s), 6.92 (1H, t, J = 9.2 Hz), 7.88 (1H, dd, J = 9.2, 1.8 Hz), 7.92 (1H, dd, J = 8.8, 2.6 Hz), 8.18 (1H, s), 8.36 (1H, d, J = 2.6 Hz), 8.48 (1H, d, J = 8.8 Hz), 8.67 (1H, s). LC/MS (A) RT 1.38 min; m/z [M + H]$^+$ 459/461. |

TABLE 14-continued

| Example | Structural formula | Physical property value |
|---|---|---|
| 19 | | ¹H-NMR (CDCl₃) δ: 1.43 (6H, d, J = 5.9 Hz), 1.61 (7H, s), 2.86 (2H, t, J = 5.9 Hz), 3.83 (2H, t, J = 5.9 Hz), 4.48 (2H, s), 4.61-4.73 (1H, m), 6.46 (1H, d, J = 2.6 Hz), 6.55 (1H, dd, J = 9.2, 2.6 Hz), 7.88 (1H, dd, J = 8.8, 2.6 Hz), 8.00 (1H, d, J = 9.2 Hz), 8.41 (1H, d, J = 2.6 Hz), 8.49 (1H, d, J = 8.8 Hz), 8.66 (1H, s). LC/MS (A) RT 1.45 min; m/z [M + H]⁺ 465. |
| 20 | | ¹H-NMR (CDCl₃) δ: 8.66 (1H, s), 8.48 (1H, d, J = 8.8 Hz), 8.33 (1H, d, J = 1.8 Hz), 8.20 (1H, s), 7.94 (1H, dd, J = 8.8, 2.6 Hz), 7.49 (1H, d, J = 8.4 Hz), 6.82-6.80 (2H, m), 4.47 (2H, s), 3.79 (2H, t, J = 5.9 Hz), 2.91 (2H, t, J = 5.7 Hz), 2.50 (3H, s). LC/MS (A) RT 1.21 min; m/z [M + H]⁺ 401. |

TABLE 15

| Example | Structural formula | Physical property value |
|---|---|---|
| 21 | | ¹H-NMR (CDCl₃) δ: 8.58 (1H, s), 8.09 (1H, d, J = 9.2 Hz), 7.50 (1H, dd, J = 12.5, 2.6 Hz), 7.18-7.15 (1H, m), 7.05 (1H, dd, J = 9.3, 2.7 Hz), 6.97 (1H, t, J = 9.0 Hz), 6.29 (1H, s), 4.53 (2H, s), 3.91-3.90 (5H, m), 2.78 (2H, t, J = 5.7 Hz). LC/MS (A) RT 1.68 min; m/z [M + H]⁺ 464. |
| 22 | | ¹H-NMR (CDCl₃) δ: 8.58 (1H, s), 8.08 (1H, d, J = 9.5 Hz), 7.49 (1H, dd, J = 12.8, 2.6 Hz), 7.16 (1H, dd, J = 8.6, 2.4 Hz), 6.97 (1H, t, J = 9.0 Hz), 6.83 (1H, dd, J = 9.3, 2.7 Hz), 6.27 (1H, s), 4.49 (2H, s), 3.90 (3H, s), 3.86 (2H, t, J = 5.7 Hz), 2.75 (2H, t, J = 5.7 Hz). LC/MS (A) RT 1.59 min; m/z [M + H]⁺ 430/432. |

TABLE 15-continued

| Example | Structural formula | Physical property value |
|---|---|---|
| 23 | | $^1$H-NMR (CDCl$_3$) δ: 8.66 (1H, s), 8.48 (1H, d, J = 9.2 Hz), 8.35 (1H, d, J = 2.6 Hz), 8.23 (1H, s), 7.93 (1H, dd, J = 8.8, 2.6 Hz), 7.42 (1H, d, J = 8.4 Hz), 6.55 (1H, dd, J = 8.8, 2.2 Hz), 6.42 (1H, d, J = 2.2 Hz), 4.48 (2H, s), 3.93 (3H, s), 3.80 (2H, t, J = 5.7 Hz), 2.91 (2H, t, J = 5.7 Hz). LC/MS (A) RT 1.27 min; m/z [M + H]$^+$ 417. |
| 24 | | $^1$H-NMR (CDCl$_3$) δ: 9.05 (1H, d, J = 9.2 Hz), 8.77 (1H, s), 8.34 (1H, d, J = 9.5 Hz), 8.28 (1H, t, J = 6.0 Hz), 8.08 (1H, d, J = 9.2 Hz), 8.05 (1H, s), 7.28 (1H, d, J = 2.6 Hz), 7.08 (1H, dd, J = 9.3, 2.7 Hz), 4.61 (2H, s), 4.18 (2H, dt, J = 17.1, 8.0 Hz), 3.95 (2H, t, J = 5.7 Hz), 3.01 (2H, t, J = 5.5 Hz). LC/MS (A) RT 1.93 min; m/z [M + H]$^+$ 543. |

TABLE 16

| Example | Structural formula | Physical property value |
|---|---|---|
| 25 | | $^1$H-NMR (CDCl$_3$) δ: 8.53 (1H, s), 8.23 (1H, s), 8.08 (1H, d, J = 8.8 Hz), 7.86 (1H, dd, J = 7.0, 3.3 Hz), 7.05 (1H, d, J = 9.2 Hz), 6.80 (1H, d, J = 9.2 Hz), 6.36 (1H, s), 4.53 (2H, s), 3.95-3.91 (5H, m), 2.83-2.81 (2H, m). LC/MS (A) RT 1.54 min; m/z [M + H]$^+$ 447. |
| 26 | | $^1$H-NMR (CDCl$_3$) δ: 8.56 (1H, s), 7.68 (1H, d, J = 8.4 Hz), 7.23 (1H, d, J = 1.8 Hz), 7.18 (1H, d, J = 2.2 Hz), 7.06 (1H, dd, J = 2.2, 8.8 Hz), 6.99 (1H, dd, J = 1.8, 8.4 Hz), 6.88 (1H, d, J = 8.4 Hz), 6.41 (1H, br-s), 4.50 (2H, s), 3.89 (6H, s), 3.85-3.92 (2H, m), 2.76 (2H, t, J = 5.7 Hz). LC/MS (A) RT 1.52 min; m/z [M + H]$^+$ 456. |

TABLE 16-continued

| Example | Structural formula | Physical property value |
|---|---|---|
| 27 | | ¹H-NMR (CDCl₃) δ: 8.62 (1H, s), 7.70 (1H, d, J = 8.8 Hz), 7.61-7.67 (2H, m), 7.23-7.27 (4H, m), 7.08 (1H, dd, J = 8.8, 2.6 Hz), 6.43 (1H, br-s), 4.52 (2H, s), 3.89 (2H, t, J = 5.8 Hz), 2.81 (2H, t, J = 5.8 Hz). LC/MS (B) RT 1.62 min; m/z [M + H]⁺ 480. |
| 28 | | ¹H-NMR (CDCl₃) δ: 2.69 (2H, t, J = 5.7 Hz), 3.79 (2H, t, J = 5.7 Hz), 4.04 (4H, s), 4.45 (2H, s), 4.85 (4H, s), 6.48 (2H, d, J = 8.8 Hz), 6.84 (1H, dd, J = 8.8, 2.6 Hz), 6.99 (1H, d, J = 2.6 Hz), 7.29 (2H, d, J = 8.8 Hz), 7.52 (1H, d, J = 8.8 Hz), 8.04 (1H, br-s), 8.50 (1H, s). LC/MS (A) RT 1.34 min; m/z [M + H]⁺ 459/461. |

TABLE 17

| Example | Structural formula | Physical property value |
|---|---|---|
| 29 | | ¹H-NMR (CDCl₃) δ: 1.52 (9H, s), 2.69-2.82 (2H, m), 3.75-3.90 (2H, m), 4.45 (2H, s), 4.58-4.75 (4H, m), 6.45 (1H, s), 6.84 (1H, dd, J = 8.8, 2.2 Hz), 6.99 (1H, d, J = 2.2 Hz), 7.20-7.33 (3H, m), 7.52 (1H, d, J = 8.8 Hz), 8.57 (1H, d, J = 5.9 Hz). LC/MS (A) RT 1.88 min; m/z [M + H]⁺ 503/505. |
| 30 | | ¹H-NMR (CDCl₃) δ: 1.47 (9H, s), 2.06-2.09 (2H, m), 2.76-2.83 (3H, m), 3.00-3.14 (4H, m), 3.18-3.25 (2H, m), 3.69-3.85 (4H, m), 3.86-3.93 (2H, m), 4.10-4.18 (2H, m), 4.53 (2H, s), 6.93 (1H, d, J = 8.8 Hz), 7.05 (1H, dd, J = 8.8, 2.6 Hz), 7.38 (1H, dd, J = 8.8, 2.6 Hz), 7.70 (1H, d, J = 2.6 Hz), 8.05-8.12 (2H, m), 8.56 (1H, s). LC/MS (A) RT 1.72 min; m/z [M + H]⁺ 692/694. |

TABLE 17-continued

| Example | Structural formula | Physical property value |
|---|---|---|
| 31 | | $^1$H-NMR (CDCl$_3$) δ: 2.78 (2H, t, J = 5.7 Hz), 3.88-3.92 (2H, m), 3.89 (3H, s), 3.90 (3H, s), 4.53 (2H, s), 6.37 (1H, br-s), 6.88 (1H, d, J = 8.4 Hz), 6.99 (1H, dd, J = 8.4, 2.6 Hz), 7.04 (1H, dd, J = 9.2, 2.9 Hz), 7.18 (1H, d, J = 2.9 Hz), 8.08 (1H, d, J = 9.2 Hz), 8.56 (1H, s). LC/MS (B) RT 1.13 min: m/z [M + H]$^+$ 476. |
| 32 | | $^1$H-NMR (CDCl$_3$) δ: 1.50 (9H, s), 2.75-2.87 (4H, m), 3.65 (2H, br-s), 3.91 (2H, t, J = 5.7 Hz), 4.50-4.56 (2H, m), 4.57-4.62 (2H, m), 6.36 (1H, s), 7.05 (1H, dd, J = 9.2, 2.9 Hz), 7.15 (1H, d, J = 8.4 Hz), 7.26-7.29 (2H, m), 8.08 (1H, d, J = 9.2 Hz), 8.58 (1H, s). LC/MS (B) RT 1.36 min; m/z [M + H]$^+$ 571. |

TABLE 18

| Example | Structural formula | Physical property value |
|---|---|---|
| 33 | | $^1$H-NMR (CDCl$_3$) δ: 2.23 (2H, s), 2.73 (2H, br-t, J = 5.7 Hz), 3.88 (2H, br-t, J = 5.7 Hz), 4.06-4.08 (3H, m), 4.54-4.60 (2H, m), 4.86 (3H, s), 6.43 (1H, br-s), 6.50 (1H, d, J = 8.4 Hz), 7.05 (1H, dd, J = 9.2, 2.6 Hz), 7.13 (1H, d, J = 2.6 Hz), 7.21 (1H, dd, J = 8.4, 2.6 Hz), 8.06 (1H, s), 8.08 (1H, d, J = 9.2 Hz), 8.52 (1H, s). LC/MS (B) RT 1.14 min; m/z [M + H]$^+$ 527. |
| 34 | | $^1$H-NMR (CDCl$_3$) δ: 2.82 (2H, t, J = 5.7 Hz), 3.91 (2H, t, J = 5.7 Hz), 4.56 (2H, s), 6.53 (1H, s), 7.05 (1H, dd, J = 9.3, 2.7 Hz), 7.27 (1H, d, J = 2.6 Hz), 7.34-7.42 (2H, m), 7.43-7.50 (3H, m), 7.60 (3H, br-d, J = 1.1 Hz), 7.79 (1H, t, J = 1.8 Hz), 8.08 (1H, d, J = 9.2 Hz), 8.62 (1H, s). LC/MS (B) RT 1.4 min; m/z [M + H]$^+$ 492. |

TABLE 18-continued

| Example | Structural formula | Physical property value |
| --- | --- | --- |
| 35 | | $^1$H-NMR (CDCl$_3$) δ: 2.82 (2H, d, J = 5.5 Hz), 3.82 (2H, t, J = 5.5 Hz), 4.48 (2H, s), 4.89 (2H, d, J = 7.3 Hz), 5.12 (2H, d, J = 7.0 Hz), 6.85 (1H, dd, J = 9.2, 1.8 Hz), 7.00 (1H, d, J = 1.8 Hz), 7.20 (1H, s), 7.53 (1H, d, J = 9.2 Hz), 7.86 (1H, t, J = 9.2 Hz), 8.51 (1H, d, J = 9.2 Hz), 8.72 (1H, s). LC/MS (A) RT 1.56 min; m/z [M + H]$^+$ 453/455. |
| 36 | | $^1$H-NMR (CDCl$_3$) δ: 1.49 (9H, s), 2.74 (2H, t, J = 5.7 Hz), 2.82 (2H, br-t, J = 5.5 Hz), 3.59-3.70 (2H, m), 3.81 (2H, t, J = 5.7 Hz), 4.45 (2H, s), 4.59 (2H, s), 6.38 (1H, s), 6.84 (1H, dd, J = 8.8, 2.6 Hz), 6.99 (1H, d, J = 2.6 Hz), 7.15 (1H, d, J = 8.1 Hz), 7.26 (1H, s), 7.52 (1H, d, J = 8.8 Hz), 8.57 (1H, s). LC/MS (A) RT 1.94 min; m/z [M + H]$^+$ 517/519. |

TABLE 19

| Example | Structural formula | Physical property value |
| --- | --- | --- |
| 37 | | $^1$H-NMR (METHANOL-d4) δ: 2.82 (2H, br-t, J = 5.9 Hz), 3.11 (2H, t, J = 6.4 Hz), 3.51 (1H, t, J = 6.4 Hz), 3.85 (2H, t, J = 5.9 Hz), 4.36 (2H, s), 4.44 (2H, s), 7.05 (1H, dd, J = 8.8, 2.6 Hz), 7.20 (1H, d, J = 2.2 Hz), 7.25 (1H, d, J = 8.4 Hz), 7.49 (1H, dd, J = 8.4, 2.2 Hz), 7.58-7.63 (2H, m), 8.39 (1H, s). LC/MS (A) RT 1.11 min; m/z [M + H]$^+$ 417/419. |
| 38 | | $^1$H-NMR (CDCl$_3$) δ: 1.96-2.06 (2H, m), 2.47 (4H, br-s), 2.55 (2H, br-t, J = 7.3 Hz), 2.75 (2H, br-t, J = 5.7 Hz), 2.92 (4 H, t, J = 4.8 Hz), 3.82 (2H, t, J = 5.5 Hz), 4.12 (2H, t, J = 6.2 Hz), 4.44 (2H, s), 6.31 (1H, s), 6.84 (1H, dd, J = 8.8, 2.2 Hz), 6.99 (1H, d, J = 2.2 Hz), 7.03 (1H, d, J = 8.8 Hz), 7.52 (1H, d, J = 8.8 Hz), 7.65 (1H, d, J = 2.2 Hz), 7.72 (1H, dd, J = 8.8, 2.2 Hz), 8.55 (1H, s). LC/MS (A) RT 1.31 min; m/z [M + H]$^+$ 572/574. |

TABLE 19-continued

| Example | Structural formula | Physical property value |
|---|---|---|
| 39 | | $^1$H-NMR (CDCl$_3$) δ: 2.12 (3H, s), 2.21-2.27 (2H, m), 2.80 (3H, br-d, J = 4.4 Hz), 2.87-3.11 (6H, m), 3.75 (2H, br-s), 3.89 (4H, s), 4.09-4.17 (2H, m), 4.52 (2H, s), 6.94 (1H, d, J = 8.8 Hz), 7.06 (1H, dd, J = 9.2, 2.2 Hz), 7.27 (1H, d, J = 2.6 Hz), 7.39 (1H, dd, J = 8.8, 2.6 Hz), 7.66 (1H, d, J = 2.2 Hz), 8.05-8.11 (1H, m), 8.52 (1H, s). LC/MS (A) RT 1.47 min; m/z [M + H]$^+$ 634/636. |

TABLE 20

| Example | Structural formula | Physical property value |
|---|---|---|
| 40 | | $^1$H-NMR (CDCl$_3$) δ: 2.77-2.84 (2H, m), 2.89 (3H, s), 3.12-3.21 (6H, m), 3.60 (4H, br-d, J = 4.4 Hz), 3.89 (3H, br-t, J = 5.9 Hz), 4.12 (3H, br-t, J = 5.5 Hz), 4.56 (2H, s), 6.92 (1H, d, J = 9.2 Hz), 7.06 (1H, dd, J = 9.2, 2.9 Hz), 7.39 (1H, dd, J = 8.8, 2.6 Hz), 7.65 (1H, d, J = 2.6 Hz), 8.07 (1H, d, J = 8.8 Hz), 8.55 (1H, s). LC/MS (A) RT 1.54 min; m/z [M + H]$^+$ 670/672. |
| 41 | | $^1$H-NMR (CDCl$_3$) δ: 2.08-2.16 (2H, m), 2.76 (3H, s), 2.81-2.85 (2H, m), 2.90-2.99 (2H, m), 3.08-3.25 (8H, m), 3.87-3.94 (2H, m), 4.04-4.13 (2H, m), 4.54 (2H, s), 6.83-6.96 (1H, m), 6.91 (1H, d, J = 8.8 Hz), 7.06 (1H, dd, J = 8.8, 2.2 Hz), 7.41 (1H, dd, J = 9.2, 2.2 Hz), 7.65 (1H, d, J = 2.2 Hz), 8.07 (1H, d, J = 9.2 Hz), 8.54 (1H, s). LC/MS (A) RT 1.45 min; m/z [M + H]$^+$ 606/608. |
| 42 | | $^1$H-NMR (CDCl$_3$) δ: 2.13 (3H, s), 2.18-2.31 (2H, m), 2.70-2.81 (2H, m), 2.91-3.16 (6H, m), 3.72-3.83 (4H, m), 3.87 (2H, br-s), 4.05-4.16 (2H, m), 4.46 (2H, s), 6.84 (1H, dd, J = 8.8, 2.2 Hz), 6.90 (1H, d, J = 8.8 Hz), 6.99 (1H, d, J = 2.2 Hz), 7.39 (1H, dd, J = 8.8, 2.2 Hz), 7.50 (1H, d, J = 8.8 Hz), 7.65 (1H, d, J = 2.2 Hz), 8.53 (1H, s). LC/MS (A) RT 1.24 min; m/z [M + H]$^+$ 580/582. |

TABLE 21

| Example | Structural formula | Physical property value |
|---|---|---|
| 43 | | $^1$H-NMR (CDCl$_3$) δ: 2.13 (3H, s), 2.20-2.31 (2H, m), 2.73-2.83 (2H, m), 2.89-3.12 (6H, m), 3.72-3.92 (6H, m), 4.14 (2H, t, J = 5.5 Hz), 4.47 (2H, s), 6.85 (2H, dd, J = 8.8, 2.2 Hz), 6.99 (1H, br-dd, J = 4.8, 2.6 Hz), 7.51 (1H, d, J = 8.8 Hz), 7.73 (2H, s), 8.16 (1H, s), 8.54 (1H, s). LC/MS (A) RT 1.32 min; m/z [M + H]$^+$ 614/616. |
| 44 | | $^1$H-NMR (CDCl$_3$) δ: 2.04-2.15 (2H, m), 2.20 (3H, s), 2.71-2.88 (8H, m), 3.65 (6H, br-s), 4.06 (2H, br-d, J = 5.1 Hz), 4.51 (2H, s), 7.01 (1H, dd, J = 8.8, 2.2 Hz), 7.06 (1H, dd, J = 8.8, 1.8 Hz), 7.11 (1H, d, J = 2.2 Hz), 7.19 (1H, br-d, J = 1.8 Hz), 7.69 (1H, d, J = 8.8 Hz), 7.87 (1H, d, J = 8.8 Hz), 8.15 (1H, br-s), 8.60 (1H, s). LC/MS (A) RT 1.4 min; m/z [M + H]$^+$ 648. |
| 45 | | $^1$H-NMR (CDCl$_3$) δ: 2.12 (3H, s), 2.18-2.27 (2H, m), 2.80-2.89 (6H, m), 2.98-3.00 (2H, m), 3.70-3.77 (2H, m), 3.80-3.88 (2H, m), 3.88-3.93 (2H, m), 4.11-4.17 (2H, m), 4.55 (2H, s), 6.71-6.82 (1H, m), 7.01 (1H, d, J = 8.4 Hz), 7.05 (1H, dd, J = 9.3, 2.7 Hz), 7.71-7.78 (2H, m), 8.07 (1H, d, J = 9.2 Hz), 8.55 (1H, s). LC/MS (A) RT 1.54 min; m/z [M + H]$^+$ 668. |
| 46 | | $^1$H-NMR (CDCl$_3$) δ: 2.11 (3H, s), 2.12-2.37 (2H, m), 2.70-2.94 (6H, m), 2.77-2.80 (2H, m), 3.56-3.79 (4H, m), 3.90 (2H, t, J = 5.9 Hz), 4.06 (2H, t, J = 6.0 Hz), 4.52 (2H, s), 6.35 (1H, br-s), 6.91 (2H, d, J = 8.8 Hz), 7.02-7.08 (1H, m), 7.41 (2H, d, J = 8.8 Hz), 8.04-8.12 (2H, m), 8.54 (1H, s). LC/MS (A) RT 1.38 min; m/z [M + H]$^+$ 600. |

TABLE 22

| Example | Structural formula | Physical property value |
|---|---|---|
| 47 | 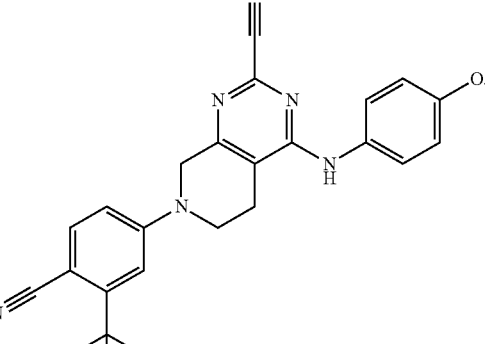 | $^1$H-NMR (CDCl$_3$) δ: 7.62 (1H, d, J = 8.8 Hz), 7.40-7.47 (2H, m), 7.23 (1H, d, J = 2.4 Hz), 7.06 (1H, dd, J = 8.8, 2.4 Hz), 6.88-6.97 (2H, m), 6.58 (1H, br-s), 4.48 (2H, s), 3.87 (2H, br-t, J = 5.6 Hz), 3.83 (3H, s), 2.79 (2H, br-t, J = 5.6 Hz). LC/MS (B) RT 1.66 min; m/z [M + H]$^+$ 451. |
| 48 | 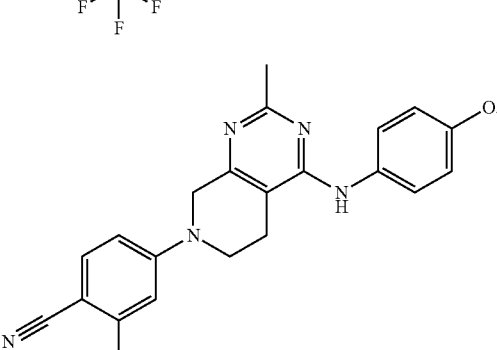 | $^1$H-NMR (DMSO-d6) δ: 8.40 (1H, s), 7.86 (1H, d, J = 8.8 Hz), 7.50-7.63 (2H, m), 7.43 (1H, d, J = 2.3 Hz), 7.37 (1H, dd, J = 8.8, 2.3 Hz), 6.87-6.94 (2H, m), 4.45 (2H, s). 3.86 (2H, br-t, J = 5.5 Hz), 3.74 (3H, d, J = 1.0 Hz), 2.73 (2H, br-t, J = 5.5 Hz), 2.34 (3H, s). LC/MS (A) RT 1.57 min; m/z [M + H]$^+$ 440. |

Biological Evaluation Test

Test Example 1: Antagonist Activity for AR

Antagonist activity for AR was evaluated according to the following method. COS-7 cells (ATCC) were transfected with pMMTV-luc vector (reporter plasmid having, as an androgen response element, murine mouse mammary virus long terminal repeat) and pEX-hAR vector (human androgen receptor expression vector: which expresses human AR gene under control of CMV promoter) by using Nucleofector (registered trademark) Kit R (Lonza) as a transfection reagent and Amaxa (Lonza). The COS-7 cells obtained after transfection were seeded in a clear bottom 96 well microplate (BD) at 1.5×10$^4$/well with phenol red free RPMI1640 containing 10% charcoal-treated fetal bovine serum (hereinbelow, DCC-FBS) (hereinbelow, the medium is referred to as an evaluation medium), and then cultured overnight. The culture was added with the evaluation medium containing dihydrotestosterone (DHT) (final concentration of DHT: 1 nmol/L) or the evaluation medium containing the compound of Examples or the compound of Comparative Example (Bicalutamide) (final concentration of the compound of Examples or the compound of Comparative Example: 5, 14, 41, 123, 370, 1111, 3333, or 10000 nmol/L), followed by culture for 24 hours. Then, the transcription activity value of the reporter plasmid was measured. The transcription activity was measured by using Bright-Glo™ Luciferase Assay System (Promega). From the measured transcription activity, 50% transcription activity inhibition concentration (IC50 value) was calculated by logistic regression when the transcription activity value obtained by using 1 nmol/L DHT was 100% and the transcription activity value obtained by using the evaluation medium only was 0%.

The results are shown in Table 23. When compared with Bicalutamide (Comparative Example), the compounds of Examples exhibited an antagonist activity for AR equal to or higher than that of Bicalutamide.

TABLE 23

| Example | AR antagonist IC50 μM |
|---|---|
| 1 | 0.0026 |
| 2 | 0.033 |
| 3 | 0.031 |
| 4 | 0.045 |
| 5 | 0.10 |
| 6 | 0.13 |
| 7 | 0.38 |
| 8 | 0.059 |
| 9 | 0.030 |
| 10 | 0.0070 |
| 11 | 0.025 |
| 13 | 0.032 |
| 14 | 0.070 |
| 15 | 0.26 |
| 16 | 0.070 |
| 17 | 0.030 |
| 18 | 1.0 |
| 19 | 1.3 |
| 20 | 0.48 |
| 23 | 0.019 |
| 24 | 0.18 |
| 26 | 1.1 |
| 27 | 1.0 |

TABLE 23-continued

| Example | AR antagonist IC50 μM |
|---|---|
| 28 | 0.68 |
| 29 | 0.22 |
| 35 | 0.12 |
| 36 | 0.18 |
| 37 | 0.69 |
| 38 | 0.95 |
| 42 | 0.56 |
| 43 | 0.30 |
| 47 | 0.70 |
| 48 | 1.0 |
| Bicalutamide | 1.3 |

Test Example 2: Inhibitory Activity on Androgen-Dependent Proliferation of Prostate Cancer Cells Human prostate cancer cells LNCaP (Non-Patent Literature 5) having amplified androgen receptor gene were seeded in a clear bottom 96 well microplate (BD) at 4.0×$10^3$/well with phenol red free RPMI1640 containing 5% DCC-FBS (hereinbelow, the medium is referred to as an evaluation medium), and then cultured overnight. The culture was added with the evaluation medium containing DHT (final concentration of DHT: 1 nmol/L) or the evaluation medium containing the compound of Examples or the compound of Comparative Example (Bicalutamide) (final concentration of the compound of Examples or the compound of Comparative Example: 5, 14, 41, 123, 370, 1111, 3333, 10000 or 30000 nmol/L), followed by culture for 72 hours. Then, the number of viable cells was measured. The number of viable cells was measured by using Cell Counting Kit-8 (DOJINDO LABORATORIES). From the measured number of viable cells, 50% proliferation inhibition concentration (GI50 value) was calculated by logistic regression when the cell proliferation activity obtained by using 1 nmol/L DHT was 100% and the cell proliferation activity obtained by using the evaluation medium only was 0%.

The results are shown in Table 24. The compounds of Examples exhibited an inhibitory activity on androgen-dependent proliferation of prostate cancer cells.

TABLE 24

| Example | Proliferation inhibition concentration GI50 value μM |
|---|---|
| 1 | 0.083 |
| 2 | 0.29 |
| 3 | 0.36 |
| 4 | 1.1 |
| 5 | 0.12 |
| 6 | 0.055 |
| 7 | 0.18 |
| 8 | 1.1 |
| 9 | 0.51 |
| 10 | 0.40 |
| 11 | 0.95 |
| 13 | 0.30 |
| 14 | 1.2 |
| 15 | 3.0 |
| 16 | 0.23 |
| 17 | 1.2 |
| 19 | 0.22 |
| 23 | 2.6 |
| 24 | 0.79 |
| 26 | 1.2 |
| 27 | 1.0 |
| 28 | 0.68 |

TABLE 24-continued

| Example | Proliferation inhibition concentration GI50 value μM |
|---|---|
| 29 | 0.83 |
| 36 | 0.15 |
| 37 | 0.99 |
| 38 | 0.12 |
| 42 | 1.3 |
| 43 | 0.38 |
| 47 | 0.45 |
| 48 | 0.61 |
| Bicalutamide | 2.3 |

Test Example 3: Agonist Activity for AR

AR positive human prostate cancer cells VCaP (In Vivo 15:163-168, 2001) were seeded in a clear bottom 96 well microplate (BD) at 1.5×$10^4$/well with phenol red free RPMI1640 containing 5% DCC-FBS (hereinbelow, the medium is referred to as an evaluation medium), and then cultured overnight. The culture was added with the evaluation medium containing the compound of Examples or the compound of Comparative Example (Bicalutamide) (final concentration of the compound of Examples or the compound of Comparative Example: 5, 14, 41, 123, 370, 1111, 3333, or 10000 nmol/L), followed by culture for 72 hours. Then, the number of viable cells was measured (test group). As a control, the cells were cultured after being added with the evaluation medium only, and the number of viable cells was measured (control group). The number of viable cells was measured by using CellTiter-Glo™ Luminescent Cell Viability Assay (Promega). From the measured number of viable cells, cell proliferation rate with respect to the compound of Examples or the compound of Comparative Examples was calculated based on the number of viable cells measured in the case of using the evaluation medium only.

Cell proliferation rate (%)=(Number of viable cells in test group−Number of viable cells in control group)/(Number of viable cells in control group)×100

By considering an error in the number of viable cells measured in the case of using the evaluation medium only, when the cell proliferation rate was more than 10% at any concentration of the 8 concentrations which had been evaluated, it was determined to have an agonist activity for AR.

Table 25 shows the results. The compounds of Examples did not exhibit any agonist activity for AR.

TABLE 25

| Example | Cell proliferation rate (%) |
|---|---|
| 1 | 9.7 |
| 3 | 8.9 |
| 4 | 9.7 |
| 5 | −1.9 |
| 6 | −1.0 |
| 7 | 0.90 |
| 8 | 5.3 |
| 9 | −3.0 |
| 11 | 4.9 |
| 13 | 7.3 |
| 14 | 1.4 |
| 15 | 7.7 |
| 16 | −1.8 |
| 17 | 9.7 |
| 18 | 9.5 |

TABLE 25-continued

| Example | Cell proliferation rate (%) |
|---|---|
| 19 | 7.8 |
| 20 | −0.89 |
| 23 | 2.3 |
| 24 | 7.8 |
| 26 | 4.5 |
| 27 | 3.8 |
| 28 | 1.4 |
| 29 | 2.4 |
| 35 | 9.4 |
| 36 | 4.9 |
| 37 | 4.6 |
| 38 | −1.3 |
| 42 | 5.1 |
| 43 | 8.4 |
| 47 | −1.7 |
| 48 | −1.6 |
| Bicalutamide | 36 |

Test Example 4: Evaluation of Activity of Reducing Expression Level of Androgen Receptor AR positive human prostate cancer cells LNCaP were seeded in a 6 well microplate (BD) at 3.5×10$^5$/well with RPMI1640 containing 5% FBS (hereinbelow, the medium is referred to as an evaluation medium), and then cultured overnight. The culture was added with the evaluation medium containing the compound of Examples or the compound of Comparative Example (Bicalutamide) such that the final concentration of the compound of Examples or the compound of Comparative Example was 10000 nmol/L, followed by culture for 48 hours. After culture for 48 hours, the medium was removed and the cells were washed with PBS and added with 0.1 mL of Lysis buffer (M-PER added with Protease Inhibitor Cocktail), followed by keeping at 4° C. for 20 minutes. After cell lysis, the cell solution was centrifuged to recover the supernatant as cell lysate. The cell lysates were adjusted to have the same protein concentration and subjected to SDS-PAGE and Western blotting using anti AR antibody (Santa Cruz Biotechnology, N-20). The antibody-reacting band (anti AR receptor) was quantified by LAS Imaging System (FUJIFILM) using Super Signal West Dura Substrate (Thermo Scientific) as a detection reagent. For the quantification, when the AR expression in LNCaP was reduced by 50% or more compared with the evaluation medium control, it was determined to have an AR expression reducing activity.

The results are shown in Table 26. When the AR expression reducing activity is 50% or more, it is described as "reduced". The compounds of the present invention were confirmed to have AR expression reducing activity of 50% or more at 10 μM.

TABLE 26

| Example | AR expression reducing activity |
|---|---|
| 1 | reduced |
| 2 | reduced |
| 3 | reduced |
| 4 | reduced |
| 5 | reduced |
| 6 | reduced |
| 7 | reduced |
| 8 | reduced |
| 9 | reduced |
| 10 | reduced |
| 11 | reduced |

TABLE 26-continued

| Example | AR expression reducing activity |
|---|---|
| 13 | reduced |
| 14 | reduced |
| 16 | reduced |
| 17 | reduced |
| 19 | reduced |
| 20 | reduced |
| 23 | reduced |
| 24 | reduced |
| 26 | reduced |
| 27 | reduced |
| 28 | reduced |
| 29 | reduced |
| 35 | reduced |
| 36 | reduced |
| 37 | reduced |
| 42 | reduced |
| 43 | reduced |
| 47 | reduced |
| 48 | reduced |
| Bicalutamide | <10% |

Test Example 5: Evaluation of Anti-Tumor Activity in In Vivo Model of Castration Resistant Prostate Cancer Based on the scientific paper (Clin Cancer Res., 2001, 7: 2941-8), castration resistant prostate cancer LNCaP-Xeno-IL-6 cells (in the paper, reported as LNCaP-IL-6+ cells) are established from the AR positive human prostate cancer cells LNCaP, and the in vivo test is carried out with the cells. The LNCaP-Xeno-IL-6 cells are implanted subcutaneously in male nude mice, and the castration treatment is performed when the tumor volume reach about 200 mm$^3$. After the castration, the vehicle only (0.5% HPMC) or the compound of Examples suspended in the vehicle is orally administered to the mice every day for 2 weeks. The compound of Examples is administered such that there is no difference in an exposure amount between the compounds. After the administration for 2 weeks, the tumor volume of each mouse is recorded and the average tumor volume of the group administered with the evaluation compound relative to the average tumor volume of the group administered only with the vehicle, that is, T/C (%), is calculated based on the following formula.

T/C (%)=(Average tumor volume of evaluation compound group)/(Average tumor volume of vehicle administration group).

The invention claimed is:

1. A fused pyrimidine compound represented by formula (I):

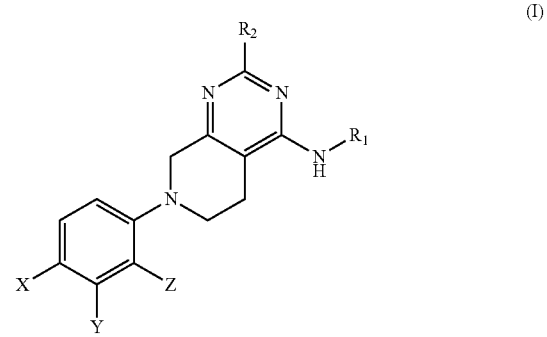

wherein, in the formula,

X represents a cyano group or a nitro group;

Y represents a halogen atom, a halogeno-$C_{1-3}$ alkyl group, a $C_{1-3}$ alkoxy group, or a $C_{1-3}$ alkyl group;

Z represents a hydrogen atom, a halogen atom, or a $C_{1-3}$ alkyl group;

$R_1$ represents a $C_{6-14}$ aryl group which is substituted with Ra and may be substituted simultaneously with Rb or a 5- or 6-membered heteroaryl group which is substituted with Ra and may be substituted simultaneously with Rb, wherein the Ra and Rb may be bonded to each other to form a fused ring together with the $C_{6-14}$ aryl group or the heteroaryl group; and $R_2$ represents a hydrogen atom, a $C_{1-3}$ alkyl group, or a cyano group, wherein Ra represents a phenyl group, a hydroxy-$C_{1-6}$ alkyl group, a hydroxy-$C_{3-7}$ cycloalkyl group, a hydroxy-heterocycloalkyl group, a $C_{1-6}$ alkoxy group which may be substituted with Rc, an amino-$C_{1-6}$ alkyl group which may be substituted with Rf, a halogeno-$C_{1-3}$ alkoxy group, a $C_{3-7}$ cycloalkylaminosulfonyl group, a $C_{1-3}$ alkylsulfonyl group, a 3- to 7-membered monocyclic heterocycloalkylsulfonyl group, a $C_{1-3}$ alkoxycarbonylamino group which may be substituted with a halogen, a $C_{1-3}$ alkylcarbonylamino group which may be substituted with a halogen, a 3- to 7-membered monocyclic heterocycloalkanecarbonyl group substituted with a hydroxy-$C_{1-6}$ alkyl group, a bicyclic heterocycloalkyl group, or —$(CH_2)_n$—C(=O)—NRdRe;

Rb represents a hydrogen atom, a halogen atom, a $C_{1-3}$ alkyl group which may be substituted with a halogen atom, or a $C_{1-4}$ alkoxy group which may be y substituted with a halogen atom;

Rc represents a pyrazolyl group, triazolyl group, or tetrazolyl group which may be substituted or a piperazinyl group which may be substituted with Rf;

Rd and Re each independently represent a hydrogen atom, a $C_{1-3}$ alkyl group, a $C_{2-6}$ alkynyl group, a $C_{1-6}$ alkoxy group, a $C_{3-7}$ cycloalkyl group, a halogeno-$C_{1-3}$ alkyl group, a hydroxy-$C_{1-6}$ alkyl group, a hydroxy-$C_{3-7}$ cycloalkyl group, a hydroxy-$C_{3-7}$ cycloalkyl-$C_{1-6}$ alkyl group, a $C_{1-4}$ alkoxy group, or a $C_{1-6}$ alkyl group substituted with Rg, or NRdRe of the —$(CH_2)_n$—C(=O)—NRdRe may form a ring;

Rf represents a $C_{1-6}$ alkyl group, a $C_{1-6}$ alkylcarbonyl group, a $C_{1-6}$ alkylsulfonyl group, a $C_{1-6}$ alkoxycarbonyl group, or a $C_{1-6}$ alkylaminocarbonyl group;

Rg represents a $C_{1-6}$ alkylpyrazolyl group, a halogeno-$C_{1-3}$ alkylthiazolyl group, an oxadiazolyl group, a halogeno-$C_{1-3}$ alkyloxadiazolyl group, or a $C_{1-6}$ alkoxycarbonylamino group; and n represents an integer of from 0 to 3, provided that:

if X is a cyano group, Y is a halogen atom or a halogeno-$C_{1-3}$ alkyl group, $R_2$ is a hydrogen atom, Z is a hydrogen atom, $R_1$ is a $C_{6-14}$ aryl group which is substituted with Ra and may be substituted simultaneously with Rb or a 5- or 6-membered heteroaryl group which is substituted with Ra and may be substituted simultaneously with Rb, and Rb is a hydrogen atom, a halogen atom, or a $C_{1-3}$ alkyl group which may be substituted with a halogen atom, then Ra is a hydroxy-heterocycloalkyl group, a $C_{1-6}$ alkoxy group which may be substituted with Rc, wherein Rc represents a piperazinyl group which may be substituted with $C_{1-6}$ alkyl, $C_{1-6}$ alkylcarbonyl, $C_{1-6}$ alkoxycarbonyl, or $C_{1-6}$ alkylaminocarbonyl, an amino-$C_{1-6}$ alkyl group which may be substituted with Rf, wherein Rf is as described above, a halogeno-$C_{1-3}$ alkoxy group, a $C_{1-3}$ alkylsulfonyl group, a bicyclic cycloheteroalkyl group, or —$(CH_2)_n$—C(=O)—NRdRe, wherein n, Rd, and Re are as described above, provided that if either one of Rd and Re is a halogeno-$C_{1-3}$ alkyl group, a hydroxy-$C_{1-6}$ alkyl group, a hydroxy-$C_{3-7}$ cycloalkyl group, a hydroxy-$C_{3-7}$ cycloalkyl-$C_{1-6}$ alkyl group, or a $C_{1-6}$ alkyl group substituted with $C_{1-6}$ alkylpyrazolyl, halogeno-$C_{1-3}$ alkylthiazolyl, oxadiazolyl, or halogeno-$C_{1-3}$ alkyloxadiazolyl, then the other is not a hydrogen atom, or a pharmaceutically acceptable salt thereof.

2. The compound or pharmaceutically acceptable salt thereof according to claim 1, wherein Z is a hydrogen atom or a fluorine atom.

3. The compound or pharmaceutically acceptable salt thereof according to claim 1, wherein $R_2$ is a hydrogen atom, a methyl group, or a cyano group.

4. The compound or pharmaceutically acceptable salt thereof according to claim 1, wherein Y is a chlorine atom, a bromine atom, a trifluoromethyl group, a methoxy group, an isopropoxy group, or a methyl group.

5. The compound or pharmaceutically acceptable salt thereof according to claim 1, wherein n is 0.

6. The compound or pharmaceutically acceptable salt thereof according to claim 1, wherein $R_1$ is a phenyl group substituted with the Ra and the Rb, a pyridinyl group substituted with the Ra and the Rb, or a pyridazinyl group substituted with the Ra and the Rb.

7. The compound or pharmaceutically acceptable salt thereof according to claim 1, wherein Ra represents a phenyl group, a hydroxy-ethyl group, a hydroxy-isopropyl group, a hydroxy-oxetanyl group, a methoxy group, a trifluoromethoxy group, a 2-oxa-6-azaspiro[3.3]heptyl group, —$(CH_2)_n$—C(=O)—NRdRe, or an n-propoxy group substituted with a piperazinyl group which may be substituted with acetyl, mesyl, tert-butoxycarbonyl, or methyl.

8. The compound or pharmaceutically acceptable salt thereof according to claim 1, wherein $R_1$ is selected from the group consisting of the following groups:

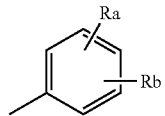

wherein, in the formula, Ra represents a phenyl group, a $C_{1-6}$ alkoxy group which may be substituted with the Rc, an amino-$C_{1-6}$ alkyl group which may be substituted with the Rf, a halogeno-$C_{1-3}$ alkoxy group, or a bicyclic heterocycloalkyl group, and Rb represents a hydrogen atom, a halogen atom, a $C_{1-3}$ alkyl group which may be substituted with a halogen atom, or a $C_{1-4}$ alkoxy group which may be substituted with a halogen atom:

or Ra is an amino-$C_{1-6}$ alkyl group which may be substituted with the Rf, and Rb is a $C_{1-3}$ alkyl group, and the Ra and Rb are bonded to each other to form a fused ring together with the ring on which they are substituted;

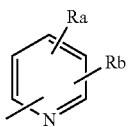

wherein, in the formula,
Ra represents a hydroxy-$C_{1-6}$ alkyl group, a hydroxy-heterocycloalkyl group, or —$(CH_2)_n$—C(=O)—NRdRe, and
Rb represents a hydrogen atom or a halogen atom; and

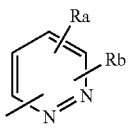

wherein, in the formula,
Ra represents —$(CH_2)_n$—C(=O)—NRdRe, and
Rb represents a hydrogen atom.

9. The compound or pharmaceutically acceptable salt thereof according to claim 1, wherein
X represents a cyano group or a nitro group;
Y represents a halogen atom, a halogeno-$C_{1-3}$ alkyl group, a $C_{1-3}$ alkoxy group, or a $C_{1-3}$ alkyl group;
Z represents a hydrogen atom or a halogen atom;
$R_1$ is a substituent selected from the group consisting of the following groups:

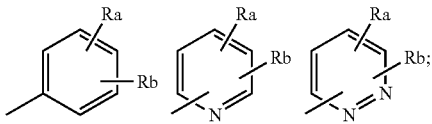

$R_2$ represents a hydrogen atom, a $C_{1-3}$ alkyl group, or a cyano group;
wherein:
Ra represents a phenyl group, a hydroxy-$C_{1-6}$ alkyl group, a hydroxy-heterocycloalkyl group, a $C_{1-6}$ alkoxy group which may be substituted with Rc, an amino-$C_{1-6}$ alkyl group which may be substituted with Rf, a halogeno-$C_{1-3}$ alkoxy group, a bicyclic heterocycloalkyl group, or —$(CH_2)_n$—C(=O)—NRdRe;
Rb represents a hydrogen atom, a halogen atom, a $C_{1-3}$ alkyl group which may be substituted with a halogen atom, or a $C_{1-4}$ alkoxy group which may be substituted with a halogen atom;
or Ra and Rb are bonded to each other to form a fused ring together with the ring on which they are substituted;
Rc represents a piperazinyl group which may be substituted with Rf;
Rd and Re each independently represent a hydrogen atom, a $C_{1-3}$ alkyl group, a $C_{2-6}$ alkynyl group, a $C_{1-6}$ alkoxy group, a $C_{3-7}$ cycloalkyl group, a halogeno-$C_{1-3}$ alkyl group, or a $C_{1-6}$ alkyl group substituted with Rg;
or NRdRe forms a 3- to 7-membered nitrogen-containing heterocyclic ring;
Rf represents a $C_{1-6}$ alkyl group, a $C_{1-6}$ alkylcarbonyl group, a $C_{1-6}$ alkylsulfonyl group, a $C_{1-6}$ alkoxycarbonyl group, or a $C_{1-6}$ alkylaminocarbonyl group;
Rg represents a $C_{1-6}$ alkoxycarbonylamino group; and
n represents an integer of 0 or 1.

10. The compound or pharmaceutically acceptable salt thereof according to claim 9, wherein
X represents a cyano group or a nitro group;
Y represents a chlorine atom, a bromine atom, a trifluoromethyl group, a methoxy group, an isopropoxy group, or a methyl group;
Z represents a hydrogen atom or a fluorine atom;
$R_1$ is a substituent selected from the group consisting of the followings:

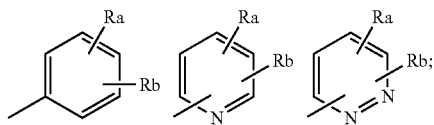

$R_2$ represents a hydrogen atom, a methyl group, or a cyano group;
Ra represents a phenyl group, a hydroxy-ethyl group, a hydroxy-isopropyl group, a hydroxy-oxetanyl group, a methoxy group, a trifluoromethoxy group, a 2-oxa-6-azaspiro[3.3]heptyl group, —$(CH_2)_n$—C(=O)—NRdRe, or an n-propoxy group substituted with a piperazinyl group which may be substituted with acetyl, tert-butoxycarbonyl, mesyl, or methyl;
Rb represents a hydrogen atom, a fluorine atom, a chlorine atom, a methyl group, a trifluoromethyl group, or a methoxy group;
or Ra and Rb are bonded to each other to form a substituted or unsubstituted tetrahydroisoquinolinyl group or isoindolinyl group together with the ring on which they are substituted;
either one of Rd and Re represents a methyl group, an ethyl group, a propynyl group, a cyclopropyl group, a trifluoroethyl group, a tert-butoxy group, or an ethyl group substituted with tert-butoxycarbonylamino, and the other represents a hydrogen atom or a methyl group;
or NRdRe forms azepane; and
n is 0.

11. The compound or pharmaceutically acceptable salt thereof according to claim 1, wherein the compound is selected from the group consisting of the following compounds (1) to (48):
(1) 6-((7-(3-chloro-4-cyanophenyl)-5,6,7,8-tetrahydropyrido[3,4-d]pyrimidin-4-yl)amino)-N-ethyl-2-fluoronicotinamide;
(2) 6-((7-(3-chloro-4-cyanophenyl)-5,6,7,8-tetrahydropyrido[3,4-d]pyrimidin-4-yl)amino)-2-fluoro-N-methylnicotinamide;
(3) 6-((7-(4-cyano-3-(trifluoromethyl)phenyl)-5,6,7,8-tetrahydropyrido[3,4-d]pyrimidin-4-yl)amino)-2-fluoro-N-methylnicotinamide;
(4) 6-((7-(4-cyano-3-(trifluoromethyl)phenyl)-5,6,7,8-tetrahydropyrido[3,4-d]pyrimidin-4-yl)amino)-N-ethyl-2-fluoronicotinamide;
(5) 6-((7-(4-cyano-3-(trifluoromethyl)phenyl)-5,6,7,8-tetrahydropyrido[3,4-d]pyrimidin-4-yl)amino)-N-ethylnicotinamide;
(6) 4-(4-((5-(azepane-1-carbonyl)pyridin-2-yl)amino)-5,6-dihydropyrido[3,4-d]pyrimidin-7(8H)-yl)-2-(trifluoromethyl)benzonitrile;
(7) N-(tert-butoxy)-6-((7-(4-cyano-3-(trifluoromethyl)phenyl)-5,6,7,8-tetrahydropyrido[3,4-d]pyrimidin-4-yl)amino)nicotinamide;

(8) tert-butyl (2-(6-((7-(4-cyano-3-(trifluoromethyl)phenyl)-5,6,7,8-tetrahydropyrido[3,4-d]pyrimidin-4-yl)amino)pyridazine-3-carboxamido)ethyl)carbamate;
(9) 6-((7-(4-cyano-3-(trifluoromethyl)phenyl)-5,6,7,8-tetrahydropyrido[3,4-d]pyrimidin-4-yl)amino)-N-cyclopropylpyridazine-3-carboxamide;
(10) 6-((7-(4-cyano-3-(trifluoromethyl)phenyl)-5,6,7,8-tetrahydropyrido[3,4-d]pyrimidin-4-yl)amino)-N-ethylpyridazine-3-carboxamide;
(11) 6-((7-(4-cyano-3-(trifluoromethyl)phenyl)-5,6,7,8-tetrahydropyrido[3,4-d]pyrimidin-4-yl)amino)-N-(prop-2-yn-1-yl)pyridazine-3-carboxamide;
(12) N-ethyl-2-fluoro-6-((7-(4-nitro-3-(trifluoromethyl)phenyl)-5,6,7,8-tetrahydropyrido[3,4-d]pyrimidin-4-yl)amino)nicotinamide;
(13) 2-(6-((7-(3-chloro-4-nitrophenyl)-5,6,7,8-tetrahydropyrido[3,4-d]pyrimidin-4-yl)amino)pyridin-3-yl)propan-2-ol;
(14) 2-(6-((7-(4-nitro-3-(trifluoromethyl)phenyl)-5,6,7,8-tetrahydropyrido[3,4-d]pyrimidin-4-yl)amino)pyridin-3-yl)propan-2-ol;
(15) 2-(6-((7-(3-methoxy-4-nitrophenyl)-5,6,7,8-tetrahydropyrido[3,4-d]pyrimidin-4-yl)amino)pyridin-3-yl)propan-2-ol;
(16) 2-(6-((7-(3-methyl-4-nitrophenyl)-5,6,7,8-tetrahydropyrido[3,4-d]pyrimidin-4-yl)amino)pyridin-3-yl)propan-2-ol;
(17) 2-(6-((7-(3-bromo-4-nitrophenyl)-5,6,7,8-tetrahydropyrido[3,4-d]pyrimidin-4-yl)amino)pyridin-3-yl)propan-2-ol;
(18) 2-(6-((7-(3-chloro-2-fluoro-4-nitrophenyl)-5,6,7,8-tetrahydropyrido[3,4-d]pyrimidin-4-yl)amino)pyridin-3-yl)propan-2-ol;
(19) 2-(6-((7-(3-isopropoxy-4-nitrophenyl)-5,6,7,8-tetrahydropyrido[3,4-d]pyrimidin-4-yl)amino)pyridin-3-yl)propan-2-ol;
(20) 4-(4-((5-(2-hydroxypropan-2-yl)pyridin-2-yl)amino)-5,6-dihydropyrido[3,4-d]pyrimidin-7(8H)-yl)-2-methylbenzonitrile;
(21) N-(3-fluoro-4-methoxyphenyl)-7-(4-nitro-3-(trifluoromethyl)phenyl)-5,6,7,8-tetrahydropyrido[3,4-d]pyrimidin-4-amine;
(22) 7-(3-chloro-4-nitrophenyl)-N-(3-fluoro-4-methoxyphenyl)-5,6,7,8-tetrahydropyrido[3,4-d]pyrimidin-4-amine;
(23) 4-(4-((5-(2-hydroxypropan-2-yl)pyridin-2-yl)amino)-5,6-dihydropyrido[3,4-d]pyrimidin-7(8H)-yl)-2-methoxybenzonitrile;
(24) 6-((7-(4-nitro-3-(trifluoromethyl)phenyl)-5,6,7,8-tetrahydropyrido[3,4-d]pyrimidin-4-yl)amino)-N-(2,2,2-trifluoroethyl)pyridazine-3-carboxamide;
(25) N-(6-methoxypyridin-3-yl)-7-(4-nitro-3-(trifluoromethyl)phenyl)-5,6,7,8-tetrahydropyrido[3,4-d]pyrimidin-4-amine;
(26) 4-(4-((3,4-dimethoxyphenyl)amino)-5,6-dihydropyrido[3,4-d]pyrimidin-7(8H)-yl)-2-(trifluoromethyl)benzonitrile;
(27) 4-(4-((4-(trifluoromethoxy)phenyl)amino)-5,6-dihydropyrido[3,4-d]pyrimidin-7(8H)-yl)-2-(trifluoromethyl)benzonitrile;
(28) 4-(4-((4-(2-oxa-6-azaspiro[3.3]heptan-6-yl)phenyl)amino)-5,6-dihydropyrido[3,4-d]pyrimidin-7(8H)-yl)-2-chlorobenzonitrile;
(29) tert-butyl 5-((7-(3-chloro-4-cyanophenyl)-5,6,7,8-tetrahydropyrido[3,4-d]pyrimidin-4-yl)amino)isoindoline-2-carboxylate;
(30) tert-butyl 4-(3-(2-chloro-4-((7-(4-nitro-3-(trifluoromethyl)phenyl)-5,6,7,8-tetrahydropyrido[3,4-d]pyrimidin-4-yl)amino)phenoxy)propyl)piperazine-1-carboxylate;
(31) N-(3,4-dimethoxyphenyl)-7-(4-nitro-3-(trifluoromethyl)phenyl)-5,6,7,8-tetrahydropyrido[3,4-d]pyrimidin-4-amine;
(32) tert-butyl 7-((7-(4-nitro-3-(trifluoromethyl)phenyl)-5,6,7,8-tetrahydropyrido[3,4-d]pyrimidin-4-yl)amino)-3,4-dihydroisoquinoline-2(1H)-carboxylate;
(33) N-(3-methyl-4-(2-oxa-6-azaspiro[3.3]heptan-6-yl)phenyl)-7-(4-nitro-3-(trifluoromethyl)phenyl)-5,6,7,8-tetrahydropyrido[3,4-d]pyrimidin-4-amine;
(34) N-([1,1'-biphenyl]-3-yl)-7-(4-nitro-3-(trifluoromethyl)phenyl)-5,6,7,8-tetrahydropyrido[3,4-d]pyrimidin-4-amine;
(35) 2-chloro-4-(4-((6-fluoro-5-(3-hydroxyoxetan-3-yl)pyridin-2-yl)amino)-5,6-dihydropyrido[3,4-d]pyrimidin-7(8H)-yl)benzonitrile;
(36) tert-butyl 7-((7-(3-chloro-4-cyanophenyl)-5,6,7,8-tetrahydropyrido[3,4-d]pyrimidin-4-yl)amino)-3,4-dihydroisoquinolin-2 (1H)-carboxylate;
(37) 2-chloro-4-(4-((1,2,3,4-tetrahydroisoquinolin-7-yl)amino)-5,6-dihydropyrido[3,4-d]pyrimidin-7(8H)-yl)benzonitrile;
(38) 2-chloro-4-(4-((4-(3-(piperazin-1-yl)propoxy)-3-(trifluoromethyl)phenyl)amino)-5,6-dihydropyrido[3,4-d]pyrimidin-7(8H)-yl)benzonitrile;
(39) 1-(4-(3-(2-chloro-4-((7-(4-nitro-3-(trifluoromethyl)phenyl)-5,6,7,8-tetrahydropyrido[3,4-d]pyrimidin-4-yl)amino)phenoxy)propyl)piperazin-1-yl)ethanone;
(40) N-(3-chloro-4-(3-(4-(methylsulfonyl)piperazin-1-yl)propoxy)phenyl)-7-(4-nitro-3-(trifluoromethyl)phenyl)-5,6,7,8-tetrahydropyrido[3,4-d]pyrimidin-4-amine;
(41) N-(3-chloro-4-(3-(4-methylpiperazin-1-yl)propoxy)phenyl)-7-(4-nitro-3-(trifluoromethyl)phenyl)-5,6,7,8-tetrahydropyrido[3,4-d]pyrimidin-4-amine;
(42) 4-(4-((4-(3-(4-acetylpiperazin-1-yl)propoxy)-3-chlorophenyl)amino)-5,6-dihydropyrido[3,4-d]pyrimidin-7(8H)-yl)-2-chlorobenzonitrile;
(43) 4-(4-((4-(3-(4-acetylpiperazin-1-yl)propoxy)-3-(trifluoromethyl)phenyl)amino)-5,6-dihydropyrido[3,4-d]pyrimidin-7(8H)-yl)-2-chlorobenzonitrile;
(44) 4-(4-((4-(3-(4-acetylpiperazin-1-yl)propoxy)-2-(trifluoromethyl)phenyl)amino)-5,6-dihydropyrido[3,4-d]pyrimidin-7(8H)-yl)-2-(trifluoromethyl)benzonitrile;
(45) 1-(4-(3-(4-((7-(4-nitro-3-(trifluoromethyl)phenyl)-5,6,7,8-tetrahydropyrido[3,4-d]pyrimidin-4-yl)amino)-2-(trifluoromethyl)phenoxy)propyl)piperazin-1-yl)ethanone;
(46) 1-(4-(3-(4-((7-(4-nitro-3-(trifluoromethyl)phenyl)-5,6,7,8-tetrahydropyrido[3,4-d]pyrimidin-4-yl)amino)phenoxy)propyl)piperazin-1-yl)ethanone;
(47) 7-(4-cyano-3-(trifluoromethyl)phenyl)-4-((4-methoxyphenyl)amino)-5,6,7,8-tetrahydropyrido[3,4-d]pyrimidine-2-carbonitrile; and
(48) 4-(4-((4-methoxyphenyl)amino)-2-methyl-5,6-dihydropyrido[3,4-d]pyrimidin-7(8H)-yl)-2-(trifluoromethyl)benzonitrile.

12. A pharmaceutical composition comprising the fused pyrimidine compound or pharmaceutically acceptable salt thereof according to claim 1, and a pharmaceutically acceptable carrier.

13. A method for inhibiting androgen activity, comprising administering an effective amount of the fused pyrimidine compound or pharmaceutically acceptable salt thereof according to claim 1 to a subject in need of treatment for prostate cancer.

14. A method for treating prostate cancer, comprising administering an effective amount of the fused pyrimidine compound or pharmaceutically acceptable salt thereof according to claim 1 to a subject in need thereof.

* * * * *